US012747267B2

(12) United States Patent
Geng

(10) Patent No.: US 12,747,267 B2
(45) Date of Patent: Sep. 29, 2026

(54) POLYPEPTIDE COMPOUND AND USE THEREOF IN TREATMENT OF ENTERITIS

(71) Applicant: Sichuan Gooddoctor Panxi Pharmaceutical Co., Ltd., Xichang City (CN)

(72) Inventor: Funeng Geng, Sichuan (CN)

(73) Assignee: Sichuan Gooddoctor Panxi Pharmaceutical Co., Ltd., Xichang City (CN)

( * ) Notice: Subject to any disclaimer, the term of this patent is extended or adjusted under 35 U.S.C. 154(b) by 227 days.

(21) Appl. No.: 18/730,237

(22) PCT Filed: Jan. 19, 2023

(86) PCT No.: PCT/CN2023/073068

§ 371 (c)(1),
(2) Date: Jul. 18, 2024

(87) PCT Pub. No.: WO2023/138644

PCT Pub. Date: Jul. 27, 2023

(65) Prior Publication Data

US 2025/0101063 A1 Mar. 27, 2025

(30) Foreign Application Priority Data

Jan. 21, 2022 (CN) ......................... 202210070418.4

(51) Int. Cl.

| | |
|---|---|
| ***C07K 7/00*** | (2006.01) |
| ***A61P 1/04*** | (2006.01) |
| ***C07K 5/10*** | (2006.01) |
| ***C07K 5/103*** | (2006.01) |
| ***C07K 5/11*** | (2006.01) |
| ***C07K 5/113*** | (2006.01) |
| ***C07K 5/117*** | (2006.01) |
| ***C07K 7/06*** | (2006.01) |
| ***C07K 7/08*** | (2006.01) |
| *A61K 38/00* | (2006.01) |

(52) U.S. Cl.

CPC *C07K 7/08* (2013.01); *A61P 1/04* (2018.01); *C07K 5/1002* (2013.01); *C07K 5/1008* (2013.01); *C07K 5/101* (2013.01); *C07K 5/1019* (2013.01); *C07K 5/1021* (2013.01); *C07K 5/1024* (2013.01); *C07K 7/06* (2013.01); *A61K 38/00* (2013.01)

(58) Field of Classification Search

CPC . C07K 7/08; C07K 5/101; C07K 7/06; C07K 5/10; A61P 1/04; A61K 38/00

See application file for complete search history.

(56) References Cited

U.S. PATENT DOCUMENTS

| | | | | |
|---|---|---|---|---|
| 2013/0029400 | A1 | 1/2013 | Lee et al. | |
| 2013/0261066 | A1 | 10/2013 | Nie et al. | |
| 2017/0114356 | A1* | 4/2017 | Li | C07K 14/415 |

FOREIGN PATENT DOCUMENTS

| | | | |
|---|---|---|---|
| CN | 107890563 | A | 4/2018 |
| CN | 108210886 | A | 6/2018 |
| CN | 108478800 | A | 9/2018 |
| CN | 110090295 | A | 8/2019 |
| CN | 111542335 | A | 8/2020 |
| CN | 112679589 | A | 4/2021 |
| CN | 112812158 | A | 5/2021 |
| CN | 112851774 | A | 5/2021 |
| WO | WO2009040088 | A1 | 4/2009 |
| WO | WO2013044499 | A1 | 4/2013 |
| WO | WO2014150566 | A1 | 9/2014 |
| WO | WO2022002186 | A1 | 1/2022 |

OTHER PUBLICATIONS

Ha et al., Anti-Inflammatory Effect of a Peptide Derived from the Synbiotics, Fermented Cudrania tricuspidata with Lactobacillus gasseri, on Inflammatory Bowel Disease, Mediators of Inflammation, 2020:3572809, 2020.

Knowles et al., Effect of Bioavailable Whey Peptides on C2C12 Muscle Cells, Proceedings, 11(35);1-4, 2019.

* cited by examiner

*Primary Examiner* — Jeanette M Lieb

(74) *Attorney, Agent, or Firm* — Travis Young; Bozicevic, Field & Francis LLP

(57) ABSTRACT

Provided is a new polypeptide. The new polypeptide shows a significant effect of relieving intestinal lumen distension in pharmacodynamic tests of a Brachydanio Rerio inflammatory bowel disease model and a rat inflammatory bowel disease model, and can be used for preparing a drug for treating enteritis, especially ulcerative colitis.

7 Claims, 1 Drawing Sheet

Specification includes a Sequence Listing.

POLYPEPTIDE COMPOUND AND USE THEREOF IN TREATMENT OF ENTERITIS

FIELD OF THE INVENTION

The present invention relates to a novel polypeptide and use thereof. The polypeptide of the present invention has a significant therapeutic effect on inflammatory bowel disease, especially has a therapeutic effect on ulcerative colitis.

BACKGROUND OF THE INVENTION

Enteritis is an inflammatory response of the intestine caused by various reasons, such as infection by intestinal bacteria, viruses and other pathogenic microorganisms, or immune damage, radiation damage, dietary stimulation, drug stimulation and other factors. Its main clinical manifestations include fever, nausea, vomiting, abdominal pain, diarrhea, watery stools or mucus, pus and blood in the stools, and some patients may also have a feeling of tenesmus.

Enteritis can be divided into specific enteritis and non-specific enteritis according to the manifestations of inflammation. Specific enteritis includes inflammatory bowel disease, necrotizing enteropathy and dysbacteriosis enteritis. Among them, inflammatory bowel disease, as a more common one, is an idiopathic, non-infectious, intestinal, chronic, persistent, recurrent, and inflammatory disease that involves the intestines. Its clinical manifestations are abdominal pain and diarrhea, pus and blood stool, and even fever, abdominal mass, emaciation and malnutrition. Inflammatory bowel disease is a chronic, long-term disease that requires long-term active treatment.

Generally, specific enteritis has a clear cause, such as bacterial enteritis, pseudomembranous enteritis, viral enteritis, radiation enteritis and the like, which are all enteritis with clear causes, while non-specific enteritis has no clear cause and is considered to be caused by immune system diseases, such as ulcerative colitis, Crohn's disease and the like. Inflammatory bowel disease includes ulcerative colitis and Crohn's disease. Ulcerative colitis is a chronic nonspecific intestinal inflammatory disease with an unclear etiology, which most often occurs in young and middle-aged people. Its clinical manifestations are persistent or recurrent diarrhea, mucus, pus and blood in the stool with abdominal pain, tenesmus and varying degrees of systemic symptoms. There may be manifestations outside the intestines, such as in skin, mucous membranes, joints, eyes, liver, gallbladder and the like. Complications include toxic megacolon, intestinal perforation, massive lower gastrointestinal bleeding, intraepithelial neoplasia, and carcinoma. There is a lack of accurate data on the morbidity of UC in China. Regional epidemiological surveys suggest that the morbidity of UC in China is 0.42-2.22/100,000. Although the morbidity is still low compared with Western countries, it has shown a clear upward trend compared with the last two decades. The lesions mainly affect the colon mucosa and submucosa, starting from the colon distal to the rectum, developing retrogradely to the proximal end, and even affecting the entire colon. In 5% of cases, the lesions may affect the terminal ileum, showing a continuous distribution. The main clinical manifestations of ulcerative colitis are diarrhea, abdominal pain, and mucus, pus and blood in the stool. The cause of the disease is not yet fully understood, but it is currently believed to be related to infection, immune abnormalities, genetics and mental factors. In addition, patients with enteritis usually have symptoms such as intestinal lumen dilatation (also known as intestinal dilatation or intestinal canal dilatation), the cause of which may be that inflammation destroys the nerve and muscle regulation mechanism that controls the normal intestine, and the pressure in the intestinal lumen causes the intestinal wall to expand beyond its normal range of motion. Alternatively, it may be caused by excessive growth of microorganisms and the toxins they produce, mucus exudation, etc. Relieving or inhibiting intestinal lumen dilatation is helpful in the treatment of enteritis.

Although the drugs currently commonly used to treat ulcerative colitis have certain preventive and therapeutic effects, they still have disadvantages such as slow absorption, long treatment cycle, and unclear treatment effect.

SUMMARY OF THE INVENTION

In order to overcome the deficiencies and defects of the prior art, an objective of the present invention is to provide a new polypeptide compound and use thereof. The inventors of the present invention have found that the polypeptide compound of the present invention can effectively or significantly alleviate or inhibit intestinal lumen dilatation, thereby playing a role in treating enteritis.

In a first aspect, the present invention relates to a compound of formula (I) or a physiologically compatible salt thereof, wherein the compound of formula (I) is as follows:

$$H\text{-}X_a\text{-}Z_1\text{-}Z_2\text{-}Z_3\text{-}Z_4\text{-}X_b\text{-}OH \qquad (I)$$

wherein $Z_1$ is Pro, Ala, Gly, D-Pro or is absent;

$Z_2$ is Val, Ala, D-Val, Ile or is absent;

$Z_3$ is Pro, Ala, Gly, D-Pro or is absent; and $Z_4$ is Gln, Ala, Glu, Ile, D-Gln or is absent;

provided that at most 2 of $Z_1$, $Z_2$, $Z_3$ and $Z_4$ are absent.

$X_a$ is a sequence containing 0-10 amino acid residues; and $X_b$ is a sequence containing 0-9 amino acid residues.

In one embodiment, 2 of $Z_1$, $Z_2$, $Z_3$ and $Z_4$ are absent. In one embodiment, $Z_1$ and $Z_2$ are absent.

In one embodiment, $Z_3$ and $Z_4$ are absent. In one embodiment, 1 of $Z_1$, $Z_2$, $Z_3$ and $Z_4$ is absent. In one embodiment, $Z_1$ is absent. In one embodiment, $Z_4$ is absent. In one embodiment, 0 of $Z_1$, $Z_2$, $Z_3$ and $Z_4$ is absent.

In one embodiment, $Z_1$ is Pro; $Z_2$ is Val; $Z_3$ is Pro; and $Z_4$ is Gln. In one embodiment, $Z_1$ is D-Pro; $Z_2$ is Val; $Z_3$ is Pro; and $Z_4$ is Gln. In one embodiment, $Z_1$ is Pro; $Z_2$ is Val; $Z_3$ is Ala; and $Z_4$ is Gln. In one embodiment, $Z_1$ is Pro; $Z_2$ is Ile; $Z_3$ is Pro; and $Z_4$ is Gln. In one embodiment, $Z_1$ is Pro; $Z_2$ is Val; $Z_3$ is Pro; and $Z_4$ is absent. In one embodiment, $Z_1$ is Pro; $Z_2$ is Ala; $Z_3$ is Pro; and $Z_4$ is Gln. In one embodiment, $Z_1$ is Gly; $Z_2$ is Val; $Z_3$ is Pro; and $Z_4$ is Gln. In one embodiment, $Z_1$ is Pro; $Z_2$ is Val; $Z_3$ is Gly; and $Z_4$ is Gln. In one embodiment, $Z_1$ is Ala; $Z_2$ is Val; $Z_3$ is Pro; and $Z_4$ is Gln. In one embodiment, $Z_1$ is Pro; $Z_2$ is Val; $Z_3$ is Pro; and $Z_4$ is Glu. In one embodiment, $Z_1$ is Pro; $Z_2$ is Val; $Z_3$ is D-Pro; and $Z_4$ is Gln. In one embodiment, $Z_1$ is Pro; $Z_2$ is Val; $Z_3$ is Pro; and $Z_4$ is D-Gln.

In one embodiment, $X_a$ is $X_{a10}$-$X_{a9}$-$X_{a8}$-$X_{a7}$-$X_{a6}$-$X_{a5}$-$X_{a4}$-$X_{a3}$-$X_{a2}$-$X_{a1}$-*, wherein * indicates the position linked to $Z_1$-$Z_2$-$Z_3$-$Z_4$, wherein $X_{a10}$ is Gly or is absent, $X_{a9}$ is Gly, Pro, Ser or is absent, $X_{a8}$ is Pro, Glu, Ser or is absent, $X_{a7}$ is Arg, Glu, Thr, Ser or is absent, $X_{a6}$ is Lys, Thr, Ala, Asp, Glu, Arg, Ser or is absent, $X_a$s is Asp, Ala, Val, Arg, Phe, Ile, Pro, Lys, Glu or is absent, $X_{a4}$ is Val, Phe, Pro, Pyro-Glu, Lys, Leu, Ile, Ala, Asp or is absent, $X_{a3}$ is Tyr, Leu, Pro, Asp, Arg, Glu, Lys, Tys, Val, Ile or is absent, $X_{a2}$ is D-Lys, Lys, Ala, Arg, Val, Glu, Tyr or is absent, and $X_{a1}$ is Glu, Ala, D-Glu, Tyr, Gln, Asp, Asn or is absent.

In one embodiment, $X_a$ is $X_{aa}$-$X_{a2}$-$X_{a1}$-*, wherein * indicates the position linked to $Z_1$-$Z_2$-$Z_3$-$Z_4$, $X_{a2}$-$X_{a1}$ is Lys-Glu-*, Arg-Glu-*, Val-Tyr-*, Glu-Glu-*, Lys-Gln-*, Lys-D-Glu-* or Tyr-Glu-*, and $X_{aa}$ is $X_{a10}$-$X_{a9}$-$X_{a8}$-$X_{a7}$-$X_{a6}$-$X_{a8}$-$X_{a4}$-$X_{a3}$-, wherein $X_{a10}$ is Gly or is absent, $X_{a9}$ is Gly, Pro, Ser or is absent, $X_{a8}$ is Pro, Glu, Ser or is absent, $X_{a7}$ is Arg, Glu, Thr, Ser or is absent, $X_{a6}$ is Lys, Thr, Ala, Asp, Glu, Arg, Ser or is absent, $X_{a5}$ is Asp, Ala, Val, Arg, Phe, Ile, Pro, Lys, Glu or is absent, $X_{a4}$ is Val, Phe, Pro, Pyro-Glu, Lys, Leu, Ile, Ala, Asp or is absent, and $X_{a3}$ is Tyr, Leu, Pro, Asp, Arg, Glu, Lys, Tys, Val, Ile or is absent. In one embodiment, $X_{aa}$ is Arg-Lys-Asp-Val-Tyr-, Gly-Pro-Glu-Thr-Ala-Phe-Leu-, Val-Pro-Pro-, Pyro-Glu-Leu-, Arg-Lys-Asp-, Gly-Pro-Glu-Thr-Ala-Phe-Leu-Arg-, Ser-Ser-Glu-Asp-Ile-Lys-Glu-, Ser-Ser-Glu-Asp-Ile-Lys-, Val-Pro-Tys-, Pro-Ala-Tys-, Arg-Lys-Asp-Val-, Ser-Ser-Glu-Asp-Ile-, or is absent, wherein the rightmost connector—indicates linkage to -$X_{a2}$-$X_{a1}$. In one embodiment, $X_a$ is $X_{aa}$-$X_{a2}$-$X_{a1}$-*, wherein * indicates the position linked to $Z_1$-$Z_2$-$Z_3$-$Z_4$, wherein $X_{a2}$-$X_{a1}$ is Lys-Glu-*, and $X_{aa}$ is as defined above.

In one embodiment, $X_a$ is $X_{a1}$-*, wherein * indicates the position linked to $Z_1$-$Z_2$-$Z_3$-$Z_4$, wherein $X_{a1}$ is Glu, Ala, D-Glu, Asp, Asn or is absent.

In one embodiment, $X_a$ is $X_{a2}$-$X_{a1}$-*, wherein * indicates the position linked to $Z_1$-$Z_2$-$Z_3$-$Z_4$, wherein $X_{a2}$ is Lys, and $X_{a1}$ is Glu, D-Glu or Gln.

In one embodiment, $X_a$ is Glu-*, Ala-*, D-Glu-*, Asp-*, Asn-*, Lys-Glu-*, D-Lys-Glu-*, Ala-Glu-*, Lys-Gln-*, Lys-D-Glu-*, Lys-Ala-*, Arg-Lys-Asp-Val-Tyr-Lys-Glu-*, Gly-Pro-Glu-Thr-Ala-Phe-Leu-Arg-Glu-*, Val-Pro-Pro-Lys-Glu-*, Pyro-Glu-Leu-Lys-Glu-*, Arg-Lys-Asp-Val-Tyr-Lys-Glu-*, yr-*, Gly-Pro-Glu-Thr-Ala-Phe-Leu-Arg-Lys-Glu-*, Ser-Ser-Glu-Asp-Ile-Lys-Glu-Lys-Glu-*, Ser-Ser-Glu-Asp-Ile-Lys-Glu-Glu-*, Val-Pro-Tys-Lys-Glu-*, Pro-Ala-Tys-Lys-Glu-*, Arg-Lys-Asp-Val-Tyr-Glu-*, Ser-Ser-Glu-Asp-Ile-Lys-Glu-* or is absent, wherein * indicates the position linked to $Z_1$-$Z_2$-$Z_3$-$Z_4$.

In one embodiment, $X_b$ is -$X_{b1}$-$X_{b2}$-$X_{b3}$-$X_{b4}$-$X_{b5}$-$X_{b6}$-$X_{b7}$-$X_{b8}$-$X_{b9}$, wherein  indicates the position linked to $Z_1$-$Z_2$-$Z_3$-$Z_4$, wherein $X_{b1}$ is Ala, D-Ala or is absent, $X_{b2}$ is Lys, Ala, D-Lys, Arg or is absent, $X_{b3}$ is Pro, Gly, D-Pro, Ser, Val, Ala or is absent, $X_{b4}$ is Arg, Ala, Ser, Pro, D-Arg or is absent, $X_{b8}$ is Lys, Ala, D-Lys, Glu, Tyr or is absent, $X_{b6}$ is Val, Asp, D-Val, Ala or is absent, $X_{b7}$ is Ala, D-Ala, Ile or is absent, $X_{b8}$ is Ala, D-Ala, Lys or is absent, and $X_{b9}$ is Gln, Ala, Glu, Asn, D-Gln or is absent.

In one embodiment, $X_b$ is -$X_{b1}$-$X_{b2}$-$X_{b3}$-$X_{b4}$-$X_{b5}$-$X_{b6}$-$X_{b7}$-$X_{b8}$-$X_{b9}$, wherein  indicates the position linked to $Z_1$-$Z_2$-$Z_3$-$Z_4$, wherein $X_{b1}$ is Ala or D-Ala, $X_{b2}$ is Lys, Ala or D-Lys, $X_{b3}$ is Pro, Gly, or Ala, $X_{b4}$ is Arg or D-Arg, $X_{b5}$ is Lys or is absent, $X_{b6}$ is Val, D-Val, Ala or is absent, $X_{b7}$ is Ala is absent, $X_{b8}$ is Ala or is absent, and $X_{b9}$ is Gln, Asn, D-Gln or is absent.

In one embodiment, $X_b$ is -$X_{b1}$-$X_{b2}$-$X_{bb}$, wherein  indicates the position linked to $Z_1$-$Z_2$-$Z_3$-$Z_4$, $X_{b1}$-$X_{b2}$- is -Ala-Lys-, -Ala-Lys-, -Ala-D-Lys-, -Ala-Ala- or -D-Ala-Lys-, $X_{bb}$ is -$X_{b3}$-$X_{b4}$-$X_{b5}$-$X_{b6}$-$X_{b7}$-$X_{b8}$-$X_{b9}$, wherein $X_{b3}$ is Pro, Gly, D-Pro, Ser, Val, Ala or is absent, $X_{b4}$ is Arg, Ala, Ser, Pro, D-Arg or is absent, $X_{b5}$ is Lys, Ala, D-Lys, Glu, Tyr or is absent, $X_{b6}$ is Val, Asp, D-Val, Ala or is absent, $X_{b7}$ is Ala, D-Ala, Ile or is absent, $X_{b8}$ is Ala, D-Ala, Lys or is absent, and $X_{b9}$ is Gln, Ala, Glu, Asn, D-Gln or is absent; or $X_{b3}$ is Pro, Gly, or Ala, $X_{b4}$ is Arg or D-Arg, $X_{b5}$ is Lys or is absent, $X_{b6}$ is Val, D-Val, Ala or is absent, $X_{b7}$ is Ala or is absent, $X_{b8}$ is Ala or is absent, and $X_{b9}$ is Gln, Asn, D-Gln or is absent. In one embodiment, $X_{bb}$ is -Pro-Arg-Lys-Val, -Pro-Arg-Lys, -Pro-Arg, -Ala-Gln, -Ala-Ala, -Pro, -Lys-Val, -Val-Pro-Tyr, -Arg-Lys, -Val-Ala, -Pro-Arg-Lys-Val-Ala, -Lys-Val-Ala-Ala-Gln, -Pro-Arg-Lys-Val-Ala-Ala-Gln, -Pro-Arg-Lys-Val-Ala-Ala-Gln, -Pro-Ala-Lys-Val-Ala-Ala-Gln, -Pro-Arg-Ala-Val-Ala-Ala-Gln, -Pro-Arg-Lys-Val-Ala-Ala-Ala, -Gly-Arg-Lys-Val-Ala-Ala-Gln, -D-Pro-Arg-Lys-Val-Ala-Ala-Gln, -Pro-Arg-D-Lys-Val-Ala-Ala-Gln, -Pro-Arg-Lys-Val-D-Ala-Ala-Gln, -Pro-Arg-Lys-Val-Ala-D-Ala-Gln, -Ser-Ser-Glu-Asp-Ile-Lys-Glu, -Pro-Arg-Lys-Val-Ala-Ala-Asn, -Pro-Arg-Lys-Val-Ala-Ala-Gln, -Pro-Arg-Lys-D-Val-Ala-Ala-Gln, -Ala-Arg-Lys-Val-Ala-Ala-Gln, -Pro-Arg-Lys-Ala-Ala-Ala-Gln, -Pro-Arg-Lys-Val-Ala-Ala-Gln, -Pro-D-Arg-Lys-Val-Ala-Ala-Gln, -Pro-Arg-Lys-Val-Ala-Ala-D-Gln or is absent, wherein the leftmost connector—indicates linkage to $X_{b1}$-$X_{b2}$. In one embodiment, $X_b$ is -$X_{b1}$-$X_{b2}$-$X_{bb}$, wherein  represents the position linked to $Z_1$-$Z_2$-$Z_3$-$Z_4$, $X_{b1}$-$X_{b2}$- is -Ala-Lys-, and $X_{bb}$ is as defined above.

In one embodiment, $X_b$ is **-Ala-.

In one embodiment, $X_b$ is -Ala-, -Ala-Lys, -Ala-D-Lys-, -Ala-Ala-, -D-Ala-Lys, -Ala-Arg, -Ala-Lys-Pro-Arg-Lys-Val, -Ala-Lys-Pro-Arg-Lys, -Ala-Lys-Pro-Arg, -Val-Ala-Ala-Gln, -Lys-Val-Ala-Ala, -Ala-Lys-Pro, -Pro-Arg-Lys-Val, -Ala-Lys-Val-Pro-Tyr, -Lys-Pro-Arg-Lys, -Arg-Lys-Val-Ala, -Ala-Lys-Pro-Arg-Lys-Val-Ala, -Pro-Arg-Lys-Val-Ala-Ala-Gln, -Ala-Lys-Pro-Arg-Lys-Val-Ala-Ala-Gln, -Ala-Ala-Pro-Arg-Lys-Val-Ala-Ala-Gln, -Ala-Lys-Pro-Ala-Lys-Val-Ala-Ala-Gln, -Ala-Lys-Pro-Arg-Ala-Val-Ala-Ala-Gln, -Ala-Lys-Pro-Arg-Lys-Val-Ala-Ala-Ala, -Ala-Lys-Gly-Arg-Lys-Val-Ala-Ala-Gln, -Ala-Lys-D-Pro-Arg-Lys-Val-Ala-Ala-Gln, -Ala-Lys-Pro-Arg-D-Lys-Val-Ala-Ala-Gln, -Ala-Lys-Pro-Arg-Lys-Val-D-Ala-Ala-Gln, -Ala-Lys-Pro-Arg-Lys-Val-Ala-D-Ala-Gln, -Ala-Lys-Ser-Ser-Glu-Asp-Ile-Lys-Glu, -Ala-Lys-Pro-Arg-Lys-Val-Ala-Ala-Asn, -Ala-D-Lys-Pro-Arg-Lys-Val-Ala-Ala-Gln, -Ala-Lys-Pro-Arg-Lys-D-Val-Ala-Ala-Gln, -Ala-Lys-Ala-Arg-Lys-Val-Ala-Ala-Gln, -Ala-Lys-Pro-Arg-Lys-Ala-Ala-Ala-Gln, -D-Ala-Lys-Pro-Arg-Lys-Val-Ala-Ala-Gln, -Ala-Lys-Pro-D-Arg-Lys-Val-Ala-Ala-Gln, -Ala-Lys-Pro-Arg-Lys-Val-Ala-Ala-D-Gln, or is absent, wherein  indicates the position linked to $Z_1$-$Z_2$-$Z_3$-$Z_4$.

In one embodiment, $Z_1$ is Pro; $Z_2$ is Val; $Z_3$ is Pro; and $Z_4$ is Gln; $X_a$ is $X_{aa}$-$X_{a2}$-$X_{a1}$-*, wherein * indicates the position linked to $Z_1$-$Z_2$-$Z_3$-$Z_4$, wherein $X_{a2}$-$X_{a1}$ is Lys-Glu-*, and $X_b$ is -$X_{b1}$-$X_{b2}$-$X_{bb}$, wherein  indicates the position linked to $Z_1$-$Z_2$-$Z_3$-$Z_4$, $X_{b1}$-$X_{b2}$- is **-Ala-Lys-, wherein $X_{aa}$ and $X_{bb}$ are as defined above.

In one embodiment, the compound is selected from:

Lys-Glu-Pro-Val-Pro-Gln-Ala-Lys-Pro-Arg-Lys-Val-Ala-Ala-Gln (SEQ ID NO: 1);

Lys-Glu-Pro-Val-Pro-Gln-Ala-Lys-Pro-Arg-Lys (SEQ ID NO: 2);

Lys-Glu-Pro-Val-Pro-Gln-Ala-Lys-Pro-Arg (SEQ ID NO: 3);
Lys-Glu-Pro-Val-Pro-Gln-Ala-Lys (SEQ ID NO: 4);
Pro-Arg-Lys-Val-Ala-Ala-Gln (SEQ ID NO: 5);
Glu-Pro-Val-Pro-Gln-Ala-Lys (SEQ ID NO: 6);
Lys-Glu-Pro-Val (SEQ ID NO: 7);
Val-Ala-Ala-Gln (SEQ ID NO: 8);
Glu-Pro-Val-Pro (SEQ ID NO: 9);
Lys-Pro-Arg-Lys (SEQ ID NO: 10);
Ala-Lys-Pro-Arg (SEQ ID NO: 11);
Pro-Val-Pro-Gln (SEQ ID NO: 12);
Val-Pro-Gln-Ala (SEQ ID NO: 13);
Pro-Gln-Ala-Lys (SEQ ID NO: 14);
Arg-Lys-Val-Ala (SEQ ID NO: 15);
Lys-Val-Ala-Ala (SEQ ID NO: 16);
Gln-Ala-Lys-Pro (SEQ ID NO: 17);
Pro-Arg-Lys-Val (SEQ ID NO: 18);
Ala-Glu-Pro-Val-Pro-Gln-Ala-Lys-Pro-Arg-Lys-Val-Ala-Ala-Gln (SEQ ID NO: 19);
Lys-Ala-Pro-Val-Pro-Gln-Ala-Lys-Pro-Arg-Lys-Val-Ala-Ala-Gln (SEQ ID NO: 20);
Lys-Glu-Ala-Val-Pro-Gln-Ala-Lys-Pro-Arg-Lys-Val-Ala-Ala-Gln (SEQ ID NO: 21);
Lys-Glu-Pro-Val-Ala-Gln-Ala-Lys-Pro-Arg-Lys-Val-Ala-Ala-Gln (SEQ ID NO: 22);
Lys-Glu-Pro-Val-Pro-Ala-Ala-Lys-Pro-Arg-Lys-Val-Ala-Ala-Gln (SEQ ID NO: 23);
Lys-Glu-Pro-Val-Pro-Gln-Ala-Ala-Pro-Arg-Lys-Val-Ala-Ala-Gln (SEQ ID NO: 24);
Lys-Glu-Pro-Ala-Pro-Gln-Ala-Lys-Pro-Arg-Lys-Val-Ala-Ala-Gln (SEQ ID NO: 25);
Lys-Glu-Pro-Val-Pro-Gln-Ala-Lys-Ala-Arg-Lys-Val-Ala-Ala-Gln (SEQ ID NO: 26);
Lys-Glu-Pro-Val-Pro-Gln-Ala-Lys-Pro-Ala-Lys-Val-Ala-Ala-Gln (SEQ ID NO: 27);
Lys-Glu-Pro-Val-Pro-Gln-Ala-Lys-Pro-Arg-Ala-Val-Ala-Ala-Gln (SEQ ID NO: 28);
Lys-Glu-Pro-Val-Pro-Gln-Ala-Lys-Pro-Arg-Lys-Ala-Ala-Ala-Gln (SEQ ID NO: 29);
Lys-Glu-Pro-Val-Pro-Gln-Ala-Lys-Pro-Arg-Lys-Val-Ala-Ala-Ala (SEQ ID NO: 30);
Lys-Glu-Gly-Val-Pro-Gln-Ala-Lys-Pro-Arg-Lys-Val-Ala-Ala-Gln (SEQ ID NO: 31);
Lys-Glu-Pro-Val-Gly-Gln-Ala-Lys-Pro-Arg-Lys-Val-Ala-Ala-Gln (SEQ ID NO: 32);
Lys-Glu-Pro-Val-Pro-Gln-Ala-Lys-Gly-Arg-Lys-Val-Ala-Ala-Gln (SEQ ID NO: 33);
Lys-Glu-Pro-Val-Gly-Gln-Ala-Lys-Gly-Arg-Lys-Val-Ala-Ala-Gln (SEQ ID NO: 34);
Lys-Glu-Gly-Val-Gly-Gln-Ala-Lys-Gly-Arg-Lys-Val-Ala-Ala-Gln (SEQ ID NO: 35);
Lys-Glu-Gly-Val-Pro-Gln-Ala-Lys-Gly-Arg-Lys-Val-Ala-Ala-Gln (SEQ ID NO: 36);
Lys-Glu-Gly-Val-Gly-Gln-Ala-Lys-Pro-Arg-Lys-Val-Ala-Ala-Gln (SEQ ID NO: 37);
Glu-Pro-Val-Pro-Gln-Ala-Lys-Pro-Arg-Lys (SEQ ID NO: 38);
Pro-Val-Pro-Gln-Ala (SEQ ID NO: 39);
Pro-Val-Pro-Glu-Ala (SEQ ID NO: 40);
Pro-Val-Pro-Ile-Ala (SEQ ID NO: 41);
Pro-Val-Pro-Ala (SEQ ID NO: 42);
Glu-Pro-Val-Pro-Gln-Ala (SEQ ID NO: 43);
Pro-Val-Pro-Gln-Ala-Lys (SEQ ID NO: 44);
Glu-Pro-Val-Pro-Gln-Ala-Arg (SEQ ID NO: 45);
Ala-Pro-Val-Pro-Gln-Ala-Lys (SEQ ID NO: 46);
Glu-Pro-Val-Pro-Ala-Ala-Lys (SEQ ID NO: 47);
Glu-Pro-Val-Pro-Gln-Ala-Ala (SEQ ID NO: 48);

Asp-Pro-Val-Pro-Gln-Ala-Lys (SEQ ID NO: 49);
Asn-Pro-Val-Pro-Gln-Ala-Lys (SEQ ID NO: 50);
Glu-Pro-Val-Pro-Gln-Ala-Lys-Pro-Arg-Lys-Val-Ala (SEQ ID NO: 51);
Glu-Pro-Ala-Pro-Gln-Ala-Lys (SEQ ID NO: 52);
Glu-Ala-Val-Pro-Gln-Ala-Lys (SEQ ID NO: 53);
Glu-Pro-Val-Ala-Gln-Ala-Lys (SEQ ID NO: 54);
Glu-Pro-Val-Pro-Glu-Ala-Lys (SEQ ID NO: 55);
Glu-Pro-Val-Pro-Gln-Ala-Lys-Pro-Arg-Lys-Val (SEQ ID NO: 56);
Glu-Pro-Val-Pro-Gln-Ala-Lys-Pro-Arg (SEQ ID NO: 57);
Glu-Pro-Val-Pro-Gln-Ala-Lys-Pro (SEQ ID NO: 58);
Pro-Val-Pro-Gln-Ala-Lys-Pro-Arg (SEQ ID NO: 59);
Pro-Val-Pro-Gln-Ala-Lys-Pro (SEQ ID NO: 60);
D-Lys-Glu-Pro-Val-Pro-Gln-Ala-Lys-Pro-Arg-Lys-Val-Ala-Ala-Gln (SEQ ID NO: 61);
Lys-D-Glu-Pro-Val-Pro-Gln-Ala-Lys-Pro-Arg-Lys-Val-Ala-Ala-Gln (SEQ ID NO: 62);
Lys-Glu-D-Pro-Val-Pro-Gln-Ala-Lys-Pro-Arg-Lys-Val-Ala-Ala-Gln (SEQ ID NO: 63);
Lys-Glu-Pro-D-Val-Pro-Gln-Ala-Lys-Pro-Arg-Lys-Val-Ala-Ala-Gln (SEQ ID NO: 64);
Lys-Glu-Pro-Val-D-Pro-Gln-Ala-Lys-Pro-Arg-Lys-Val-Ala-Ala-Gln (SEQ ID NO: 65);
Lys-Glu-Pro-Val-Pro-D-Gln-Ala-Lys-Pro-Arg-Lys-Val-Ala-Ala-Gln (SEQ ID NO: 66);
Lys-Glu-Pro-Val-Pro-Gln-D-Ala-Lys-Pro-Arg-Lys-Val-Ala-Ala-Gln (SEQ ID NO: 67);
Lys-Glu-Pro-Val-Pro-Gln-Ala-D-Lys-Pro-Arg-Lys-Val-Ala-Ala-Gln (SEQ ID NO: 68);
Lys-Glu-Pro-Val-Pro-Gln-Ala-Lys-D-Pro-Arg-Lys-Val-Ala-Ala-Gln (SEQ ID NO: 69);
Lys-Glu-Pro-Val-Pro-Gln-Ala-Lys-Pro-D-Arg-Lys-Val-Ala-Ala-Gln (SEQ ID NO: 70);
Lys-Glu-Pro-Val-Pro-Gln-Ala-Lys-Pro-Arg-D-Lys-Val-Ala-Ala-Gln (SEQ ID NO: 71);
Lys-Glu-Pro-Val-Pro-Gln-Ala-Lys-Pro-Arg-Lys-D-Val-Ala-Ala-Gln (SEQ ID NO: 72);
Lys-Glu-Pro-Val-Pro-Gln-Ala-Lys-Pro-Arg-Lys-Val-D-Ala-Ala-Gln (SEQ ID NO: 73);
Lys-Glu-Pro-Val-Pro-Gln-Ala-Lys-Pro-Arg-Lys-Val-Ala-D-Ala-Gln (SEQ ID NO: 74);
Lys-Glu-Pro-Val-Pro-Gln-Ala-Lys-Pro-Arg-Lys-Val-Ala-Ala-D-Gln (SEQ ID NO: 75);
Glu-Gly-Val-Pro-Gln-Ala-Lys (SEQ ID NO: 76);
Glu-Pro-Val-Gly-Gln-Ala-Lys (SEQ ID NO: 77);
D-Glu-Pro-Val-Pro-Gln-Ala-Lys (SEQ ID NO: 78);
Glu-D-Pro-Val-Pro-Gln-Ala-Lys (SEQ ID NO: 79);
Glu-Pro-D-Val-Pro-Gln-Ala-Lys (SEQ ID NO: 80);
Glu-Pro-Val-D-Pro-Gln-Ala-Lys (SEQ ID NO: 81);
Glu-Pro-Val-Pro-D-Gln-Ala-Lys (SEQ ID NO: 82);
Glu-Pro-Val-Pro-Gln-D-Ala-Lys (SEQ ID NO: 83);
Glu-Pro-Val-Pro-Gln-Ala-D-Lys (SEQ ID NO: 84);
Lys-Glu-Pro-Val-Pro (SEQ ID NO: 85);
Glu-Pro-Val-Pro-Gln (SEQ ID NO: 86);
Lys-Glu-Pro-Val-Pro-Gln (SEQ ID NO: 87);
Val-Pro-Tyr-Lys-Glu-Pro-Val-Pro-Gln-Ala-Lys-Pro-Arg-Lys-Val-Ala-Ala-Gln (SEQ ID NO: 88);
Pyro-Glu-Leu-Lys-Glu-Pro-Val-Pro-Gln-Ala-Lys-Pro-Arg-Lys-Val-Ala-Ala-Gln (SEQ ID NO: 89);
Pro-Ala-Tyr-Lys-Glu-Pro-Val-Pro-Gln-Ala-Lys-Pro-Arg-Lys-Val-Ala-Ala-Gln (SEQ ID NO: 90);
Arg-Lys-Asp-Val-Tyr-Lys-Glu-Pro-Val-Pro-Gln-Ala-Lys-Pro-Arg-Lys-Val-Ala-Ala-Gln (SEQ ID NO: 91);
Arg-Lys-Asp-Val-Tyr-Lys-Glu-Pro-Val-Pro-Gln-Ala-Lys (SEQ ID NO: 92);

Arg-Lys-Asp-Val-Tyr-Glu-Pro-Val-Pro-Gln-Ala-Lys (SEQ ID NO: 93);
Arg-Lys-Asp-Val-Tyr-Pro-Val-Pro-Gln (SEQ ID NO: 94);
Gly-Pro-Glu-Thr-Ala-Phe-Leu-Arg-Lys-Glu-Pro-Val-Pro-Gln-Ala-Lys-Pro-Arg-Lys-Val-Ala-Ala-Gln (SEQ ID NO: 95);
Gly-Pro-Glu-Thr-Ala-Phe-Leu-Arg-Glu-Pro-Val-Pro-Gln-Ala-Lys (SEQ ID NO: 96);
Ser-Ser-Glu-Asp-Ile-Lys-Glu-Lys-Glu-Pro-Val-Pro-Gln-Ala-Lys-Pro-Arg-Lys-Val-Ala-Ala-Gln (SEQ ID NO: 97);
Ser-Ser-Glu-Asp-Ile-Lys-Glu-Glu-Pro-Val-Pro-Gln-Ala-Lys (SEQ ID NO: 98);
Ser-Ser-Glu-Asp-Ile-Lys-Glu-Pro-Val-Pro-Gln (SEQ ID NO: 99);
Val-Pro-Pro-Lys-Glu-Pro-Val-Pro-Gln-Ala-Lys-Pro-Arg-Lys-Val-Ala-Ala-Gln (SEQ ID NO: 100);
Glu-Pro-Val-Pro-Gln-Ala-Lys-Ser-Ser-Glu-Asp-Ile-Lys-Glu (SEQ ID NO: 101);
Glu-Pro-Val-Pro-Gln-Ala-Lys-Val-Pro-Tyr (SEQ ID NO: 102);
Lys-Glu-Pro-Val-Pro-Gln-Ala-Lys-Pro-Arg-Lys-Val-Ala-Ala-Glu (SEQ ID NO: 103);
Lys-Glu-Pro-Val-Pro-Gln-Ala-Lys-Pro-Arg-Lys-Val-Ala-Ala-Asn (SEQ ID NO: 104);
Lys-Gln-Pro-Val-Pro-Gln-Ala-Lys-Pro-Arg-Lys-Val-Ala-Ala-Gln (SEQ ID NO: 105);
Lys-Glu-Pro-Ile-Pro-Gln-Ala-Lys-Pro-Arg-Lys-Val-Ala-Ala-Gln (SEQ ID NO: 106);
Val-Pro-Gln-Ala (SEQ ID NO: 107); or
Val-Pro-Gln-Ala-Lys (SEQ ID NO: 108).

In one embodiment, the compound is selected from:
Lys-Glu-Pro-Val-Pro-Gln-Ala-Lys-Pro-Arg-Lys-Val-Ala-Ala-Gln (SEQ ID NO: 1);
Lys-Glu-D-Pro-Val-Pro-Gln-Ala-Lys-Pro-Arg-Lys-Val-Ala-Ala-Gln (SEQ ID NO: 63);
Gly-Pro-Glu-Thr-Ala-Phe-Leu-Arg-Glu-Pro-Val-Pro-Gln-Ala-Lys (SEQ ID NO: 96);
Val-Pro-Pro-Lys-Glu-Pro-Val-Pro-Gln-Ala-Lys-Pro-Arg-Lys-Val-Ala-Ala-Gln (SEQ ID NO: 100);
Lys-Glu-Pro-Val-Pro-Gln-Ala-Lys-Pro-Arg-Lys-Val-Ala-Ala-Asn (SEQ ID NO: 104);
Glu-Pro-Val-Pro-Gln-Ala-Lys (SEQ ID NO: 6);
Pro-Val-Pro-Gln (SEQ ID NO: 12);
Glu-Pro-Val-Ala-Gln-Ala-Lys (SEQ ID NO: 54);
Glu-Pro-Val-Pro-Gln-Ala-Lys-Pro-Arg (SEQ ID NO: 57);
Lys-Glu-Pro-Val-Pro-Gln-Ala-D-Lys-Pro-Arg-Lys-Val-Ala-Ala-Gln (SEQ ID NO: 68);
Lys-Glu-Pro-Val-Pro-Gln-Ala-Lys-Pro-Arg-Lys-D-Val-Ala-Ala-Gln (SEQ ID NO: 72);
Pyro-Glu-Leu-Lys-Glu-Pro-Val-Pro-Gln-Ala-Lys-Pro-Arg-Lys-Val-Ala-Ala-Gln (SEQ ID NO: 89);
Arg-Lys-Asp-Val-Tyr-Lys-Glu-Pro-Val-Pro-Gln-Ala-Lys (SEQ ID NO: 92);
Arg-Lys-Asp-Val-Tyr-Pro-Val-Pro-Gln (SEQ ID NO: 94);
Gly-Pro-Glu-Thr-Ala-Phe-Leu-Arg-Lys-Glu-Pro-Val-Pro-Gln-Ala-Lys-Pro-Arg-Lys-Val-Ala-Ala-Gln (SEQ ID NO: 95);
Ser-Ser-Glu-Asp-Ile-Lys-Glu-Lys-Glu-Pro-Val-Pro-Gln-Ala-Lys-Pro-Arg-Lys-Val-Ala-Ala-Gln (SEQ ID NO: 97);
Ser-Ser-Glu-Asp-Ile-Lys-Glu-Glu-Pro-Val-Pro-Gln-Ala-Lys (SEQ ID NO: 98);
Lys-Gln-Pro-Val-Pro-Gln-Ala-Lys-Pro-Arg-Lys-Val-Ala-Ala-Gln (SEQ ID NO: 105);
Lys-Glu-Pro-Ile-Pro-Gln-Ala-Lys-Pro-Arg-Lys-Val-Ala-Ala-Gln (SEQ ID NO: 106);
Lys-Glu-Pro-Val-Pro-Gln-Ala-Lys (SEQ ID NO: 4);
Pro-Arg-Lys-Val-Ala-Ala-Gln (SEQ ID NO: 5);
Glu-Pro-Val-Pro (SEQ ID NO: 9);
Lys-Pro-Arg-Lys (SEQ ID NO: 10);
Arg-Lys-Val-Ala (SEQ ID NO: 15);
Lys-Glu-Pro-Ala-Pro-Gln-Ala-Lys-Pro-Arg-Lys-Val-Ala-Ala-Gln (SEQ ID NO: 25);
Lys-Glu-Pro-Val-Pro-Gln-Ala-Lys-Ala-Arg-Lys-Val-Ala-Ala-Gln (SEQ ID NO: 26);
Lys-Glu-Pro-Val-Pro-Gln-Ala-Lys-Pro-Arg-Lys-Ala-Ala-Ala-Gln (SEQ ID NO: 29);
Lys-Glu-Gly-Val-Pro-Gln-Ala-Lys-Pro-Arg-Lys-Val-Ala-Ala-Gln (SEQ ID NO: 31);
Lys-Glu-Pro-Val-Gly-Gln-Ala-Lys-Gly-Arg-Lys-Val-Ala-Ala-Gln (SEQ ID NO: 34);
Glu-Pro-Val-Pro-Gln-Ala-Lys-Pro-Arg-Lys (SEQ ID NO: 38);
Glu-Pro-Val-Pro-Gln-Ala-Ala (SEQ ID NO: 48);
Asp-Pro-Val-Pro-Gln-Ala-Lys (SEQ ID NO: 49);
Asn-Pro-Val-Pro-Gln-Ala-Lys (SEQ ID NO: 50);
Glu-Pro-Val-Pro-Gln-Ala-Lys-Pro-Arg-Lys-Val-Ala (SEQ ID NO: 51);
Glu-Ala-Val-Pro-Gln-Ala-Lys (SEQ ID NO: 53);
Glu-Pro-Val-Pro-Glu-Ala-Lys (SEQ ID NO: 55);
Lys-D-Glu-Pro-Val-Pro-Gln-Ala-Lys-Pro-Arg-Lys-Val-Ala-Ala-Gln (SEQ ID NO: 62);
Lys-Glu-Pro-Val-D-Pro-Gln-Ala-Lys-Pro-Arg-Lys-Val-Ala-Ala-Gln (SEQ ID NO: 65);
Lys-Glu-Pro-Val-Pro-D-Gln-Ala-Lys-Pro-Arg-Lys-Val-Ala-Ala-Gln (SEQ ID NO: 66);
Lys-Glu-Pro-Val-Pro-Gln-D-Ala-Lys-Pro-Arg-Lys-Val-Ala-Ala-Gln (SEQ ID NO: 67);
Lys-Glu-Pro-Val-Pro-Gln-Ala-Lys-Pro-D-Arg-Lys-Val-Ala-Ala-Gln (SEQ ID NO: 70);
Lys-Glu-Pro-Val-Pro-Gln-Ala-Lys-Pro-Arg-Lys-Val-Ala-Ala-D-Gln (SEQ ID NO: 75);
Glu-Pro-Val-Pro-Gln-D-Ala-Lys (SEQ ID NO: 83);
Lys-Glu-Pro-Val-Pro (SEQ ID NO: 85);
Glu-Pro-Val-Pro-Gln (SEQ ID NO: 86);
Val-Pro-Tyr-Lys-Glu-Pro-Val-Pro-Gln-Ala-Lys-Pro-Arg-Lys-Val-Ala-Ala-Gln (SEQ ID NO: 88);
Pro-Ala-Tyr-Lys-Glu-Pro-Val-Pro-Gln-Ala-Lys-Pro-Arg-Lys-Val-Ala-Ala-Gln (SEQ ID NO: 90);
Arg-Lys-Asp-Val-Tyr-Glu-Pro-Val-Pro-Gln-Ala-Lys (SEQ ID NO: 93);
Ser-Ser-Glu-Asp-Ile-Lys-Glu-Pro-Val-Pro-Gln (SEQ ID NO: 99); or
Lys-Glu-Pro-Val-Pro-Gln-Ala-Lys-Pro-Arg-Lys-Val-Ala-Ala-Glu (SEQ ID NO: 103).

In a second aspect, the present invention provides the use of the polypeptide compound or a physiologically compatible salt thereof in the preparation of a drug for treating enteritis; or a method for treating enteritis, the method comprising administering a therapeutically effective amount of the polypeptide compound or a physiologically compatible salt thereof to a subject; or the polypeptide compound or a physiologically compatible salt thereof for treating enteritis.

Furthermore, enteritis includes specific enteritis and non-specific enteritis. Furthermore, specific enteritis includes inflammatory bowel disease, necrotizing enteropathy and flora imbalance enteritis.

Furthermore, inflammatory bowel disease includes ulcerative colitis.

Furthermore, the present invention provides a pharmaceutical composition comprising the polypeptide compound of the present invention or a physiologically compatible salt thereof, and a pharmaceutically acceptable excipient.

Furthermore, the dosage forms of the drug include tablets, capsules, solutions, powders and pills.

The beneficial effects of the novel polypeptide provided by the present invention and use thereof:

The polypeptide of the present invention has a short peptide chain, so it is absorbed faster and better. The experimental results show that the polypeptide provided in the present application showed a significant effect of alleviating intestinal lumen dilatation in the test of a rat model of acute inflammatory bowel disease; and had a significant therapeutic effect in the test of the rat model of acute inflammatory bowel disease. The polypeptide of the present invention has a significant effect of alleviating colitis and can be used to prepare drugs for treating enteritis, especially drugs for ulcerative colitis.

DETAILED DESCRIPTION OF THE INVENTION

Figure 1:
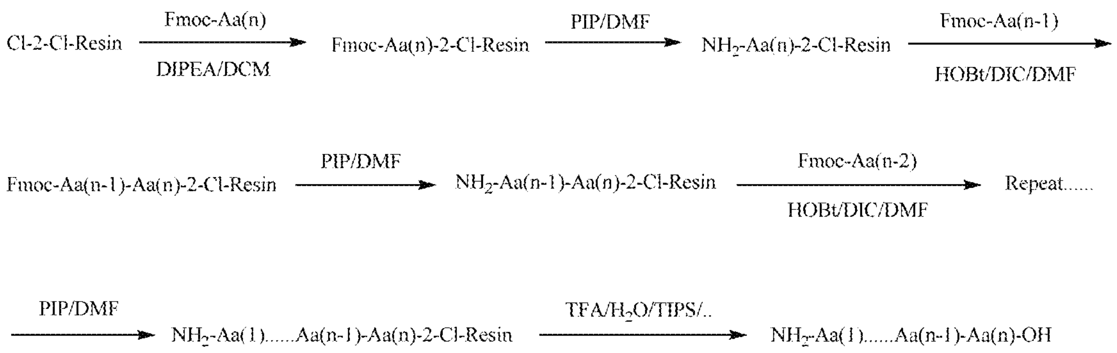
FIG. 1 shows a schematic diagram of the steps of solid phase synthesis of polypeptides.
Figure 2:
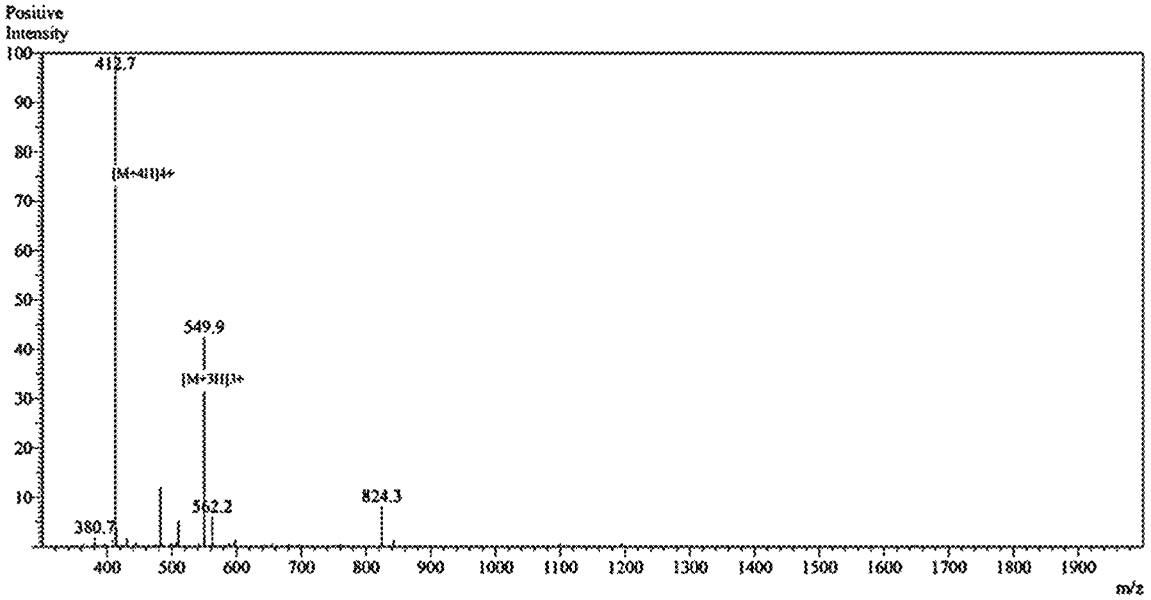
FIG. 2 shows the mass spectrum of the polypeptide.

The following is an explanation of the present invention in combination with specific experiments, which is not intended to limit the scope of protection of the present invention.

As used in the present application (including the attached claims), unless the context otherwise clearly indicates, singular forms of words such as "one/a, an" and "the" include their corresponding plural referents.

Unless otherwise clearly indicated by the context, the term "or" is used to refer to the term "and/or" and may be used interchangeably with the term "and/or".

The term "effective amount" or "therapeutically effective amount" refers to the amount of an active ingredient (such as a compound) which when administered to a subject to treat a disease, or at least one clinical symptom of a disease or disorder, is sufficient to influence the treatment of the disease, disorder or symptom. The "therapeutically effective amount" may vary depending on the compound, the disease, disorder and/or symptoms of the disease or disorder, the severity of the disease, disorder and/or symptoms of the disease or disorder, the age of the subject to be treated and/or the weight of the subject to be treated. In any given case, the appropriate amount will be apparent to those skilled in the art, or can be determined by routine experimentation. In some embodiments, a "therapeutically effective amount" is an amount of at least one compound and/or at least one stereoisomer thereof, and/or at least one pharmaceutically acceptable salt thereof, disclosed in the present application, that is effective for the "treatment" (as defined above) of a disease or disorder in a subject. In the case of a combination therapy, "therapeutically effective amount" is the total amount of the combined objects used to effectively treat a disease, disorder or condition.

The term "physiologically compatible salt" refers to a salt form which is physiologically compatible (i.e., pharmacologically acceptable), and is substantially non-toxic to the individual to which the compounds of the invention will be administered. Physiologically compatible salts of the compounds of this invention include conventional and stoichiometric acid addition salts or base addition salts formed from suitable non-toxic organic or inorganic acids or inorganic bases.

The term "intestinal lumen dilatation" refers to intestinal dilatation or intestinal canal dilatation. In patients with enteritis, due to various factors such as intestinal damage, mucus exudation, intestinal gas or fluid accumulation, microbial overgrowth and the like, the intestinal lumen is dilated and the intestinal canal is thicker than normal. Recurrent enteritis such as inflammatory bowel disease leading to intestinal canal dilatation, or tumors causing intestinal canal dilatation and intestinal obstruction are common in clinic.

The abbreviations for amino acid used in the present application are as follows.

TABLE 1

English names and abbreviations of solvents and reagents, and their corresponding Chinese names

| Chinese name | English name | Abbreviation |
|---|---|---|
| 丙氨酸 | Alanine | Ala |
| 精氨酸 | Arginine | Arg |
| 天冬酰胺 | Asparagine | Asn |
| 天冬氨酸 | Aspartic acid | Asp |
| 半胱氨酸 | Cysteine | Cys |
| 谷氨酰胺 | Glutamine | Gln |
| 谷氨酸 | Glutamic acid | Glu |
| 甘氨酸 | Glycine | Gly |
| 组氨酸 | Histidine | His |
| 异亮氨酸 | Isoleucine | Ile |
| 亮氨酸 | Leucine | Leu |
| 赖氨酸 | Lysine | Lys |
| 蛋氨酸 | Methionine | Met |
| 苯丙氨酸 | Phenylalanine | Phe |
| 脯氨酸 | Proline | Pro |
| 丝氨酸 | Serine | Ser |
| 苏氨酸 | Threonine | Thr |
| 色氨酸 | Tryptophan | Trp |
| 酪氨酸 | Tyrosine | Tyr |
| 缬氨酸 | Valine | Val |

| English name and abbreviation | Chinese name |
|---|---|
| 2-Chlorotrityl Chloride Resin | 2-chlorotrityl chloride Resin |
| DMF | N, N-dimethyl formamide |
| DCM | Dichloromethane |
| PIP | Piperidine |
| HOBt | 1-hydroxybenzotriazole |
| DIPEA | N,N-diisopropylethylamine |
| Methanol | Methyl alcohol |
| tert-Butyl methyl ether | Methyl tertiary butyl ether |
| TFA | Trifluoroacetic acid |
| TIPS | Triisopropylsilane |
| DIC | N,N'-diisopropyl carbodiimide |
| Ethanol | Ethyl alcohol |
| Aa | Amino acid |

Example 1: Chemical Synthesis of Polypeptides

The synthesis of polypeptide compounds adopts the conventional solid phase synthesis method using a fully automatic polypeptide synthesizer, and the chemical synthesis of the polypeptide is carried out through the processes of resin swelling, deprotection, washing, amino acid activation and condensation.

Taking Lys-Glu-Pro-Val-Pro-Gln-Ala-Lys-Pro-Arg-Lys-Val-Ala-Ala-Gln (SEQ ID NO: 1) as an example, the schematic diagram of the solid phase synthesis steps of the polypeptide is shown in FIG. 1.

Step 1: Preparation of Fully Protected Peptide Resin for Polypeptide (1) Resin swelling: 7.71 g (SD=0.73 mmol/g) of 2-Chlorotrityl Chloride Resin was weighed, added into a synthesis tube with a sieve plate, and swollen with 100 ml of dichloromethane (DCM).

(2) Preparation of Fmoc-Gln (Trt)-resin: Fmoc-Gln(Trt)-OH and DIPEA were weighed in a molar ratio of 1:1.78:4.31 of resin, Fmoc-Gln(Trt)-OH and DIPEA respectively and added into the synthesis tube. Nitrogen ($N_2$) bubbling and shaking were performed at room temperature for 1-3 h, and then the mixture was pumped dry; then the mixture was washed with dimethylformamide (DMF) 5 times, 100 ml each time, and the resin was pumped dry.

(3) Removal of Fmoc protecting group: 100 ml of a 20% piperidine-DMF (v/v) solution was added into the reactor, nitrogen was bubbled, and the system was allowed to react for 20 min, pumped dry, then washed with DMF 5 times, at 100 ml/time, 3 min/time, pumped dry, and detected for the Fmoc removal result by the ninhydrin method.

(4) Amino acid pre-activation: 15 mmol of Fmoc-protected amino acid, 15 mmol of HOBt, and 15 mmol of DIC was added into a 250 ml beaker, dissolved in 100 ml of DMF, and stirred at room temperature for later use.

(5) Amino acid linkage: The activated protected amino acid solution was poured into the reactor, and an appropriate amount of DCM was additionally added to clean the apparatus. Nitrogen was bubbled at room temperature and the system was allowed to react for 1-3 h, and whether the amino acid linkage is complete was detected using the ninhydrin method. If so, the system was pumped dry. The resin was washed with DMF 5 times, at 100 ml/time, 3 min/time, and then pumped dry. The amount of each of the amino acids and condensing agents used is shown in Table 2.

(6) After the condensation of the first amino acid was completed, steps (4) and (5) were repeated to extend the peptide chain in the order of amino acids until the coupling of last amino acid was completed.

(7) The resin peptide was washed with DMF 4 times, at 150 ml/time, 3 min/time; then washed with DCM 5 times, at 150 ml/time, 3 min/time, and pumped dry.

TABLE 2

Usages of amino acids and condensing agents

| Amino acid name | Aa/eq | Amino acid usage/g | HOBt/g | DIPEA/g | DIC/g |
|---|---|---|---|---|---|
| Fmoc-L-Gln(Trt)-OH | 10 | 6.107 | 1 | 3.128 | / |
| Fmoc-L-Ala-OH•$H_2O$ | 15 | 4.941 | 2.027 | / | 2.379 |
| Fmoc-L-Ala-OH•$H_2O$ | 15 | 4.941 | 2.027 | / | 2.379 |
| Fmoc-L-Val-OH | 15 | 5.091 | 2.027 | / | 2.379 |
| Fmoc-L-Lys(Boc)-OH | 15 | 7.029 | 2.027 | / | 2.379 |
| Fmoc-L-Arg(Pbf)-OH | 15 | 9.732 | 2.027 | / | 2.379 |
| Fmoc-L-Pro-OH•$H_2O$ | 15 | 5.061 | 2.027 | / | 2.379 |
| Fmoc-L-Lys(Boc)-OH | 15 | 7.029 | 2.027 | / | 2.379 |
| Fmoc-L-Ala-OH•$H_2O$ | 15 | 4.941 | 2.027 | / | 2.379 |
| Fmoc-L-Gln(Trt)-OH | 15 | 9.161 | 2.027 | / | 2.379 |
| Fmoc-L-Pro-OH•$H_2O$ | 15 | 5.061 | 2.027 | / | 2.379 |
| Fmoc-L-Val-OH | 15 | 5.091 | 2.027 | / | 2.379 |
| Fmoc-L-Pro-OH•$H_2O$ | 15 | 5.061 | 2.027 | / | 2.379 |
| Fmoc-L-Glu(OtBu)-OH•$H_2O$ | 15 | 6.653 | 2.027 | / | 2.379 |
| Fmoc-L-Lys(Boc)-OH | 15 | 7.029 | 2.027 | / | 2.379 |

Step 2: Cleaving (1) 100 ml of a cleavage agent (TFA:TIPS:$H_2O$=95:2.5:2.5, v/v) was added into the synthesis tube, nitrogen was bubbled, the system was allowed to react for 1.5-3 h.

(2) After the cleavage reaction was completed, the cleavage agent was suction-filtered into a 250 ml round-bottom flask. After vacuum concentration to one-fourth of the original volume of the cleavage agent, 10 times the existing volume of methyl tert-butyl ether was added to precipitate a white solid. The obtained mixture was filtered and washed three times with 50 ml of methyl tert-butyl ether, and then the obtained crude peptide product was placed in a sand core funnel and blowed dry with nitrogen in a fume hood to evaporate the solvent until the crude peptide was in powder form. 9.04 g of crude peptide was obtained with a crude yield of 74.7%.

Step 3: Purification, Salt Exchange and Freeze-Drying

Polypeptide HPLC Direct Salt Exchange (Acetate Salt)

A. Chromatographic parameters

Chromatographic column: dynamic axial compression column 80*250 mm, filler: Daisogel C18 (SP-100-8-ODS-P)

Eluent A1: 0.1 M acetic acid

Eluent A2: 0.025 M acetic acid-0.1 M ammonium acetate

Eluent B: acetonitrile

Flow rate: 180 ml/min

UV detection wavelength: 220 nm

B. Operating steps a) Dissolving the crude peptide in water and/or acetonitrile and filtering through a 0.45 μm filter membrane b) Equilibrating the chromatographic column with 95% A1+5% B c) Sample injection d) Equilibrating the chromatographic column with 95% A2+5% B e) Gradient elution with A1 and B f) Collecting the target peptide eluate g) Rotary evaporation for concentration h) Freeze drying 8.26 g of crude peptide was purified to obtain 4.92 g of pure peptide, with a purification yield of 59.5%.

In a similar manner to the synthesis of SEQ ID NO: 1, other compounds were synthesized. The results are shown in Table 3 and other parts of the specification.

TABLE 3

Synthesized polypeptide compounds

| SEQ ID NO. | Compound sequence | Crude product (g) | Purification yield | Acetate purity | MS |
|---|---|---|---|---|---|
| 1 | Lys-Glu-Pro-Val-Pro-Gln-Ala-Lys-Pro-Arg-Lys-Val-Ala-Ala-Gln | 9.04 | 59.5% | 99.44% | 412.70 (quadruply charged) 549.9 (triply charged) |
| 2 | Lys-Glu-Pro-Val-Pro-Gln-Ala-Lys-Pro-Arg-Lys | 2.04 | 14.7% | 97.05% | 426.60 (triply charged) 639.30 (doubly charged) |
| 3 | Lys-Glu-Pro-Val-Pro-Gln-Ala-Lys-Pro-Arg | 2.11 | 25.7% | 97.47% | 383.90 (triply charged) 575.20 (doubly charged) |
| 4 | Lys-Glu-Pro-Val-Pro-Gln-Ala-Lys | 1.55 | 26.1% | 98.22% | 448.70 (doubly charged) 896.20 $[M + H]^+$ |
| 5 | Pro-Arg-Lys-Val-Ala-Ala-Gln | 1.06 | 30.6% | 96.82% | 385.60 (doubly charged) 769.20 $[M + H]^+$ |
| 6 | Glu-Pro-Val-Pro-Gln-Ala-Lys | 1.64 | 20.8% | 98.32% | 384.70 (doubly charged) 768.20 $[M + H]^+$ |
| 7 | Lys-Glu-Pro-Val | 4.30 | 52.0% | 97.22% | 472.20 $[M + H]^+$ |
| 8 | Val-Ala-Ala-Gln | 3.60 | 53.0% | 100% | 388.10 $[M + H]^+$ |
| 9 | Glu-Pro-Val-Pro | N/A | 57.0% | 99.01% | 441.30 $[M + H]^+$ |
| 10 | Lys-Pro-Arg-Lys | 0.50 | 13.5% | 98.39% | 264.70 doubly charged 528.20 $[M + H]^+$ |
| 11 | Ala-Lys-Pro-Arg | 3.79 | 17.3% | 98.79% | 471.20 $[M + H]^+$ |
| 12 | Pro-Val-Pro-Gln | 0.20 | 48.7% | 100% | 440.30 $[M + H]^+$ |
| 13 | Val-Pro-Gln-Ala | 0.35 | 57.5% | 99.42% | 414.30 $[M + H]^+$ |
| 14 | Pro-Gln-Ala-Lys | 3.81 | 22.0% | 98.20% | 443.10 $[M + H]^+$ |
| 15 | Arg-Lys-Val-Ala | 4.23 | 32.5% | 97.48% | 237.10 (doubly charged) 473.20 $[M + H]^+$ |
| 16 | Lys-Val-Ala-Ala | 3.81 | 27.0% | 98.17% | 388.10 $[M + H]^+$ |
| 17 | Gln-Ala-Lys-Pro | N/A | 22.9% | 96.01% | 443.20 $[M + H]^+$ |
| 18 | Pro-Arg-Lys-Val | N/A | 17.7% | 97.47% | 250.20 (doubly charged) 499.30 $[M + H]^+$ |
| 19 | Ala-Glu-Pro-Val-Pro-Gln-Ala-Lys-Pro-Arg-Lys-Val-Ala-Ala-Gln | 1.73 | 43.7% | 100% | 795.60 (doubly charged) 530.80 (triply charged) |
| 20 | Lys-Ala-Pro-Val-Pro-Gln-Ala-Lys-Pro-Arg-Lys-Val-Ala-Ala-Gln | 1.96 | 45.8% | 99.36% | 795.10 (doubly charged) 530.50 (triply charged) |
| 21 | Lys-Glu-Ala-Val-Pro-Gln-Ala-Lys-Pro-Arg-Lys-Val-Ala-Ala-Gln | 1.24 | 54.9% | 99.59% | 811.10 (doubly charged) 541.20 (triply charged) |
| 22 | Lys-Glu-Pro-Val-Ala-Gln-Ala-Lys-Pro-Arg-Lys-Val-Ala-Ala-Gln | 1.5 | 46.5% | 99.54% | 811.10 (doubly charged) 541.20 (triply charged) |
| 23 | Lys-Glu-Pro-Val-Pro-Ala-Ala-Lys-Pro-Arg-Lys-Val-Ala-Ala-Gln | 1.67 | 51.3% | 99.42% | 795.50 (doubly charged) 530.70 (triply charged) |
| 24 | Lys-Glu-Pro-Val-Pro-Gln-Ala-Ala-Pro-Arg-Lys-Val-Ala-Ala-Gln | 2.65 | 52.6% | 99.72% | 795.50 (doubly charged) 530.70 (triply charged) |

TABLE 3-continued

Synthesized polypeptide compounds

| SEQ ID NO. | Compound sequence | Crude product (g) | Purification yield | Acetate purity | MS |
|---|---|---|---|---|---|
| 25 | Lys-Glu-Pro-Ala-Pro-Gln-Ala-Lys-Pro-Arg-Lys-Val-Ala-Ala-Gln | 3.21 | 51.8% | 99.90% | 810.20 (doubly charged) 540.50 (triply charged) |
| 26 | Lys-Glu-Pro-Val-Pro-Gln-Ala-Lys-Ala-Arg-Lys-Val-Ala-Ala-Gln | 3.09 | 53.6% | 99.82% | 811.00 (doubly charged) 541.00 (triply charged) |
| 27 | Lys-Glu-Pro-Val-Pro-Gln-Ala-Lys-Pro-Ala-Lys-Val-Ala-Ala-Gln | 3.07 | 42.0% | 98.06% | 781.50 (doubly charged) 521.40 (triply charged) |
| 28 | Lys-Glu-Pro-Val-Pro-Gln-Ala-Lys-Pro-Arg-Ala-Val-Ala-Ala-Gln | 2.74 | 42.3% | 99.73% | 795.50 (doubly charged) 530.70 (triply charged) |
| 29 | Lys-Glu-Pro-Val-Pro-Gln-Ala-Lys-Pro-Arg-Lys-Ala-Ala-Ala-Gln | 2.61 | 39.2% | 99.10% | 810.00 (doubly charged) 540.40 (triply charged) |
| 30 | Lys-Glu-Pro-Val-Pro-Gln-Ala-Lys-Pro-Arg-Lys-Val-Ala-Ala-Ala | 1.82 | 53.5% | 99.68% | 795.60 (doubly charged) 530.80 (triply charged) |
| 31 | Lys-Glu-Gly-Val-Pro-Gln-Ala-Lys-Pro-Arg-Lys-Val-Ala-Ala-Gln | 2.38 | 50.3% | 100% | 804.10 (doubly charged) 536.50 (triply charged) |
| 32 | Lys-Glu-Pro-Val-Gly-Gln-Ala-Lys-Pro-Arg-Lys-Val-Ala-Ala-Gln | 1.93 | 38.5% | 99.12% | 804.10 (doubly charged) 536.40 (triply charged) |
| 33 | Lys-Glu-Pro-Val-Pro-Gln-Ala-Lys-Gly-Arg-Lys-Val-Ala-Ala-Gln | 2.95 | 55.5% | 100% | 536.50 (triply charged) 804.00 (doubly charged) |
| 34 | Lys-Glu-Pro-Val-Gly-Gln-Ala-Lys-Gly-Arg-Lys-Val-Ala-Ala-Gln | 3.37 | 53.2% | 100% | 523.10 (triply charged) 784.10 (doubly charged) |
| 35 | Lys-Glu-Gly-Val-Gly-Gln-Ala-Lys-Gly-Arg-Lys-Val-Ala-Ala-Gln | 2.51 | 59.1% | 100% | 509.7 (triply charged) 764.10 (doubly charged) |
| 36 | Lys-Glu-Gly-Val-Pro-Gln-Ala-Lys-Gly-Arg-Lys-Val-Ala-Ala-Gln | 2.93 | 53.4% | 100% | 523.10 (triply charged) 784.10 (doubly charged) |
| 37 | Lys-Glu-Gly-Val-Gly-Gln-Ala-Lys-Pro-Arg-Lys-Val-Ala-Ala-Gln | 2.65 | 59.4% | 100% | 523.10 (triply charged) 784.10 (doubly charged) |
| 38 | Glu-Pro-Val-Pro-Gln-Ala-Lys-Pro-Arg-Lys | 1.85 | 51.1% | 99.00% | 575.50 (doubly charged) 384.00 (triply charged) |
| 39 | Pro-Val-Pro-Gln-Ala | | N/A | 99.93% | 511.20 $[M + H]^+$ |
| 40 | Pro-Val-Pro-Glu-Ala | 4.50 | 47.9% | 100% | 512.40 $[M + H]^+$ |
| 41 | Pro-Val-Pro-Ile-Ala | 4.77 | 60.8% | 99.87% | 496.50 $[M + H]^+$ |
| 42 | Pro-Val-Pro-Ala | 3.48 | 60.7% | 100% | 383.30 $[M + H]^+$ |
| 43 | Glu-Pro-Val-Pro-Gln-Ala | 0.66 | 60.1% | 97.77% | 640.20 $[M + H]^+$ |
| 44 | Pro-Val-Pro-Gln-Ala-Lys | 0.61 | 45.2% | 99.87% | 639.30 $[M + H]^+$ |
| 45 | Glu-Pro-Val-Pro-Gln-Ala-Arg | 0.73 | 42.3% | 98.98% | 796.30 $[M + H]^+$ |
| 46 | Ala-Pro-Val-Pro-Gln-Ala-Lys | 0.70 | 52.8% | 99.78% | 710.30 $[M + H]^+$ |
| 47 | Glu-Pro-Val-Pro-Ala-Ala-Lys | 1.02 | 39.7% | 98.55% | 711.40 $[M + H]^+$ |

TABLE 3-continued

| Synthesized polypeptide compounds | | | | | |
|---|---|---|---|---|---|
| SEQ ID NO. | Compound sequence | Crude product (g) | Purification yield | Acetate purity | MS |
| 48 | Glu-Pro-Val-Pro-Gln-Ala-Ala | 1.03 | 63.3% | 97.75% | 711.40 $[M + H]^+$ |
| 49 | Asp-Pro-Val-Pro-Gln-Ala-Lys | N/A | N/A | 99.69% | 754.30 $[M + H]^+$ |
| 50 | Asn-Pro-Val-Pro-Gln-Ala-Lys | 1.03 | 58.3% | 99.53% | 753.30 $[M + H]^+$ |
| 51 | Glu-Pro-Val-Pro-Gln-Ala-Lys-Pro-Arg-Lys-Val-Ala | N/A | N/A | 97.89% | 660.50 (doubly charged) |
| 52 | Glu-Pro-Ala-Pro-Gln-Ala-Lys | 1.04 | 56.9% | 99.14% | 740.30 $[M + H]^+$ |
| 53 | Glu-Ala-Val-Pro-Gln-Ala-Lys | N/A | N/A | 98.45% | 371.80 doubly charged 742.40 $[M + H]^+$ |
| 54 | Glu-Pro-Val-Ala-Gln-Ala-Lys | 0.66 | 63.2% | 98.35% | 742.40 $[M + H]^+$ |
| 55 | Glu-Pro-Val-Pro-Glu-Ala-Lys | N/A | N/A | 97.91% | 385.30 (doubly charged) 769.30 $[M + H]^+$ |
| 56 | Glu-Pro-Val-Pro-Gln-Ala-Lys-Pro-Arg-Lys-Val | N/A | N/A | 98.46% | 417.10 (triply charged) 625.10 $[M + H]^+$ |
| 57 | Glu-Pro-Val-Pro-Gln-Ala-Lys-Pro-Arg | N/A | N/A | 98.76% | 511.40 (doubly charged) |
| 58 | Glu-Pro-Val-Pro-Gln-Ala-Lys-Pro | N/A | N/A | 98.17% | 433.30 (doubly charged) 865.50 $[M + H]^+$ |
| 59 | Pro-Val-Pro-Gln-Ala-Lys-Pro-Arg | N/A | N/A | 99.47% | 298.20 (triply charged) 446.90 (doubly charged) 892.50 $[M + H]^+$ |
| 60 | Pro-Val-Pro-Gln-Ala-Lys-Pro | N/A | N/A | 99.42% | 368.90 (doubly charged) 736.40 $[M + H]^+$ |
| 61 | D-Lys-Glu-Pro-Val-Pro-Gln-Ala-Lys-Pro-Arg-Lys-Val-Ala-Ala-Gln | 2.35 | 52.4% | 100% | 824.2 doubly charged 549.8 triply charged |
| 62 | Lys-D-Glu-Pro-Val-Pro-Gln-Ala-Lys-Pro-Arg-Lys-Val-Ala-Ala-Gln | 2.21 | 53.8% | 100% | 824.2 doubly charged 549.8 triply charged |
| 63 | Lys-Glu-D-Pro-Val-Pro-Gln-Ala-Lys-Pro-Arg-Lys-Val-Ala-Ala-Gln | 2.1 | 54.3% | 100% | 824.2 doubly charged 549.9 triply charged |
| 64 | Lys-Glu-Pro-D-Val-Pro-Gln-Ala-Lys-Pro-Arg-Lys-Val-Ala-Ala-Gln | 2.1 | 54.8% | 99.74% | 824.2 doubly charged 549.7 triply charged |
| 65 | Lys-Glu-Pro-Val-D-Pro-Gln-Ala-Lys-Pro-Arg-Lys-Val-Ala-Ala-Gln | 1.97 | 48.6% | 100% | 824.1 doubly charged 549.8 triply charged |
| 66 | Lys-Glu-Pro-Val-Pro-D-Gln-Ala-Lys-Pro-Arg-Lys-Val-Ala-Ala-Gln | 1.99 | 59.8% | 100% | 824.1 doubly charged 549.8 triply charged |
| 67 | Lys-Glu-Pro-Val-Pro-Gln-D-Ala-Lys-Pro-Arg-Lys-Val-Ala-Ala-Gln | 1.71 | 86.5% | 100% | 824.2 doubly charged 549.8 triply charged |
| 68 | Lys-Glu-Pro-Val-Pro-Gln-Ala-D-Lys-Pro-Arg-Lys-Val-Ala-Ala-Gln | 2.21 | 71.5% | 100% | 824.2 doubly charged 549.9 triply charged |
| 69 | Lys-Glu-Pro-Val-Pro-Gln-Ala-Lys-D-Pro-Arg-Lys-Val-Ala-Ala-Gln | 1.87 | 74.3% | 99.59% | 824.3 doubly charged 549.8 triply charged |

TABLE 3-continued

Synthesized polypeptide compounds

| SEQ ID NO. | Compound sequence | Crude product (g) | Purification yield | Acetate purity | MS |
|---|---|---|---|---|---|
| 70 | Lys-Glu-Pro-Val-Pro-Gln-Ala-Lys-Pro-D-Arg-Lys-Val-Ala-Ala-Gln | 1.99 | 63.4% | 100% | 824.3 doubly charged 549.9 triply charged |
| 71 | Lys-Glu-Pro-Val-Pro-Gln-Ala-Lys-Pro-Arg-D-Lys-Val-Ala-Ala-Gln | 2.15 | 67.1% | 100% | 824.2 doubly charged 549.9 triply charged |
| 72 | Lys-Glu-Pro-Val-Pro-Gln-Ala-Lys-Pro-Arg-Lys-D-Val-Ala-Ala-Gln | 1.95 | 73.3% | 100% | 824.2 doubly charged 550.0 triply charged |
| 73 | Lys-Glu-Pro-Val-Pro-Gln-Ala-Lys-Pro-Arg-Lys-Val-D-Ala-Ala-Gln | 2.94 | 46.3% | 97.94% | 824.0 doubly charged 549.7 triply charged |
| 74 | Lys-Glu-Pro-Val-Pro-Gln-Ala-Lys-Pro-Arg-Lys-Val-Ala-D-Ala-Gln | 3.32 | 37.3% | 99.12% | 824.1 doubly charged 549.8 triply charged |
| 75 | Lys-Glu-Pro-Val-Pro-Gln-Ala-Lys-Pro-Arg-Lys-Val-Ala-Ala-D-Gln | 3.73 | 44.2% | 99.03% | 824.1 doubly charged 549.7 triply charged |
| 76 | Glu-Gly-Val-Pro-Gln-Ala-Lys | N/A | N/A | 97.45% | 364.80 doubly charged 728.50 $[M + H]^+$ |
| 77 | Glu-Pro-Val-Gly-Gln-Ala-Lys | N/A | N/A | 97.89% | 364.80 doubly charged 728.50 $[M + H]^+$ |
| 78 | D-Glu-Pro-Val-Pro-Gln-Ala-Lys | N/A | N/A | 96.92% | 768.50 $[M + H]^+$ 384.90 doubly charged |
| 79 | Glu-D-Pro-Val-Pro-Gln-Ala-Lys | N/A | N/A | 96.65% | 768.60 $[M + H]^+$ 384.70 doubly charged |
| 80 | Glu-Pro-D-Val-Pro-Gln-Ala-Lys | 3.86 | 48.5% | 98.51% | 768.5 $[M + H]^+$ 384.9 doubly charged |
| 81 | Glu-Pro-Val-D-Pro-Gln-Ala-Lys | 3.39 | 45.6% | 98.06% | 768.6 $[M + H]^+$ 384.8 doubly charged |
| 82 | Glu-Pro-Val-Pro-D-Gln-Ala-Lys | 3.76 | 41.2% | 98.34% | 768.6 $[M + H]^+$ 384.9 doubly charged |
| 83 | Glu-Pro-Val-Pro-Gln-D-Ala-Lys | 3.83 | 45.2% | 97.85% | 768.3 $[M + H]^+$ 384.7 doubly charged |
| 84 | Glu-Pro-Val-Pro-Gln-Ala-D-Lys | N/A | 55.0% | 97.06% | 768.2 $[M + H]^+$ |
| 85 | Lys-Glu-Pro-Val-Pro | 3.38 | 42.8% | 99.94% | 569.1 $[M + H]^+$ |
| 86 | Glu-Pro-Val-Pro-Gln | 330 m | 38.4% | 97.14% | 569.2 $[M + H]^+$ |
| 87 | Lys-Glu-Pro-Val-Pro-Gln | 560 m | 91.8% | 98.83% | 697.3 $[M + H]^+$ 349.1 doubly charged |
| 88 | Val-Pro-Tyr-Lys-Glu-Pro-Val-Pro-Gln-Ala-Lys-Pro-Arg-Lys-Val-Ala-Ala-Gln | 3.57 | 39.7% | 99.40% | 669.6 triply charged 1003.7 doubly charged |
| 89 | Pyro-Glu-Leu-Lys-Glu-Pro-Val-Pro-Gln-Ala-Lys-Pro-Arg-Lys-Val-Ala-Ala-Gln | 2.66 | 48.6% | 99.86% | 624.5 triply charged 936.1 doubly charged |
| 90 | Pro-Ala-Tyr-Lys-Glu-Pro-Val-Pro-Gln-Ala-Lys-Pro-Arg-Lys-Val-Ala-Ala-Gln | 3.15 | 49.3% | 98.66% | 660.2 triply charged 990.2 doubly charged |

TABLE 3-continued

| Synthesized polypeptide compounds | | | | | |
|---|---|---|---|---|---|
| SEQ ID NO. | Compound sequence | Crude product (g) | Purification yield | Acetate purity | MS |
| 91 | Arg-Lys-Asp-Val-Tyr-Lys-Glu-Pro-Val-Pro-Gln-Ala-Lys-Pro-Arg-Lys-Val-Ala-Ala-Gln | 3.37 | 27.4% | 100% | 770.2 triply charged 1154.8 doubly charged |
| 92 | Arg-Lys-Asp-Val-Tyr-Lys-Glu-Pro-Val-Pro-Gln-Ala-Lys | 1.82 | 44.1% | 98.42% | 779.4 doubly charged 520.0 triply charged |
| 93 | Arg-Lys-Asp-Val-Tyr-Glu-Pro-Val-Pro-Gln-Ala-Lys | 1.3 | 48.5% | 98.83% | 715.3 doubly charged 477.3 triply charged |
| 94 | Arg-Lys-Asp-Val-Tyr-Pro-Val-Pro-Gln | 0.77 | 57.1% | 98.08% | 551.3 doubly charged 1101.5 $[M + H]^+$ |
| 95 | Gly-Pro-Glu-Thr-Ala-Phe-Leu-Arg-Lys-Glu-Pro-Val-Pro-Gln-Ala-Lys-Pro-Arg-Lys-Val-Ala-Ala-Gln | 1.58 | 52.7% | 94.96% | 840.2 triply charged 1260.2 doubly charged |
| 96 | Gly-Pro-Glu-Thr-Ala-Phe-Leu-Arg-Glu-Pro-Val-Pro-Gln-Ala-Lys | 0.98 | 55.1% | 96.59% | 820.4 doubly charged 547.2 triply charged |
| 97 | Ser-Ser-Glu-Asp-Ile-Lys-Glu-Lys-Glu-Pro-Val-Pro-Gln-Ala-Lys-Pro-Arg-Lys-Val-Ala-Ala-Gln | 4.04 | 39.1% | 94.51% | 812.7 triply charged 1218.4 doubly charged |
| 98 | Ser-Ser-Glu-Asp-Ile-Lys-Glu-Glu-Pro-Val-Pro-Gln-Ala-Lys | 2.42 | 43.6% | 99.27% | 779.0 doubly charged 519.7 triply charged |
| 99 | Ser-Ser-Glu-Asp-Ile-Lys-Glu-Pro-Val-Pro-Gln | 1.58 | 49.9% | 98.08% | 614.9 doubly charged 1228.6 $[M + H]^+$ |
| 100 | Val-Pro-Pro-Lys-Glu-Pro-Val-Pro-Gln-Ala-Lys-Pro-Arg-Lys-Val-Ala-Ala-Gln | 2.81 | 37.9% | 100% | 647.5 triply charged 970.8 doubly charged |
| 101 | Glu-Pro-Val-Pro-Gln-Ala-Lys-Ser-Ser-Glu-Asp-Ile-Lys-Glu | 4.65 | 11.0% | 98.63% | 778.9 doubly charged 519.6 triply charged |
| 102 | Glu-Pro-Val-Pro-Gln-Ala-Lys-Val-Pro-Tyr | 4.3 | 49.8% | 97.73% | 564.1 doubly charged 1127.5 $[M + H]^+$ |
| 103 | Lys-Glu-Pro-Val-Pro-Gln-Ala-Lys-Pro-Arg-Lys-Val-Ala-Ala-Glu | 5.9 | 26.3% | 99.84% | 824.4 doubly charged 550.0 triply charged |
| 104 | Lys-Glu-Pro-Val-Pro-Gln-Ala-Lys-Pro-Arg-Lys-Val-Ala-Ala-Asn | 6.04 | 42.8% | 98.79% | 817.0 doubly charged 545.1 triply charged |
| 105 | Lys-Gln-Pro-Val-Pro-Gln-Ala-Lys-Pro-Arg-Lys-Val-Ala-Ala-Gln | 6.4 | 39.3% | 98.66% | 823.6 doubly charged 549.5 triply charged |
| 106 | Lys-Glu-Pro-Ile-Pro-Gln-Ala-Lys-Pro-Arg-Lys-Val-Ala-Ala-Gln | 5.98 | 39.7% | 99.54% | 831.1 doubly charged 554.5 triply charged |

TABLE 3-continued

| Synthesized polypeptide compounds | | | | | |
|---|---|---|---|---|---|
| SEQ ID NO. | Compound sequence | Crude product (g) | Purification yield | Acetate purity | MS |
| 107 | Val-Pro-Gln-Ala | 0.47 | 47.2% | 100% | 414.2 $[M + H]^+$ |
| 108 | Val-Pro-Gln-Ala-Lys | 0.50 | 51.3% | 99.63% | 542.3 $[M + H]^+$ |

Note:
A doubly charged peak indicates that the target molecule is bound to 2 protons, and a triply charged peak indicates that the target molecule is bound to 3 protons; and N/A means that the weighing is difficult and the actual weight is not considered.

SEQ ID NO: 1: Lys-Glu-Pro-Val-Pro-Gln-Ala-Lys-Pro-Arg-Lys-Val-Ala-Ala-Gln (Acetate Salt)

High resolution mass spectrometry (TOF-HRMS), molecular formula: $C_{73}H_{127}N_{23}O_{20}$; m/z:m/z: 549.65904 ($[M+3H]^{3+}$), 823.98493 ($[M+2H]^{2+}$), 1646.96346 ([M+H]+).

$^1$H NMR (600 MHz, $D_2O$+$CD_3CN$) δ 4.48 (dd, J=9.5, 4.1 Hz, 1H), 4.42 (dd, J=9.2, 4.5 Hz, 1H), 4.32-4.27 (m, 1H), 4.27-4.21 (m, 3H), 4.20-4.07 (m, 6H), 4.00 (dd, J=8.3, 4.8 Hz, 1H), 3.95 (d, J=7.5 Hz, 1H), 3.86 (t, J=6.7 Hz, 1H), 3.77-3.62 (m, 3H), 3.59-3.43 (m, 3H), 3.04 (t, J=6.7 Hz, 2H), 2.87-2.78 (m, 6H), 2.28-2.08 (m, 9H), 2.00-1.80 (m, 31H, AcOH), 1.80-1.41 (m, 23H), 1.40-1.24 (m, 6H), 1.24-1.18 (m, 9H), 0.87-0.73 (m, 12H).

SEQ ID NO: 2: Lys-Glu-Pro-Val-Pro-Gln-Ala-Lys-Pro-Arg-Lys (Acetate Salt)

High resolution mass spectrometry (TOF-HRMS), molecular formula: $C_{57}H_{100}N_{18}O_{15}$; m/z: 426.59680 ($[M+3H]^{3+}$), 639.39021 ($[M+2H]^{2+}$), 1277.77023 ($[M+H]^+$).

1H NMR (600 MHz, DMSO-d6) δ 4.57 (dd, J=8.7, 4.9 Hz, 1H), 4.41-4.11 (m, 10H), 3.83 (s, 1H), 3.78 (t, J=6.5 Hz, 1H), 3.54 (d, J=73.5 Hz, 7H), 3.08 (d, J=7.0 Hz, 2H), 2.74-2.68 (m, 7H), 2.32 (d, J=9.1 Hz, 2H), 2.23-2.17 (m, 2H), 2.05-1.46 (m, AcOH, 56H), 1.43-1.22 (m, 7H), 1.17 (d, J=7.0 Hz, 3H), 0.82 (dd, J=19.6, 6.7 Hz, 6H).

SEQ ID NO: 3: Lys-Glu-Pro-Val-Pro-Gln-Ala-Lys-Pro-Arg (Acetate Salt)

High resolution mass spectrometry (TOF-HRMS), molecular formula: $C_{51}H_{88}N_{16}O_{14}$; m/z: 383.89927 ($[M+3H]^{3+}$), 575.34276 ($[M+2H]^{2+}$), 1149.67551 ($[M+H]^+$).

$^1$H NMR (600 MHz, DMSO-$d_6$) δ 4.58-4.55 (m, 1H), 4.44-4.37 (m, 2H), 4.33 (dd, J=8.4, 4.2 Hz, 1H), 4.30-4.22 (m, 3H), 4.16-4.12 (m, 2H), 3.79 (d, J=6.1 Hz, 1H), 3.64-3.48 (m, 6H), 3.08 (t, J=7.0 Hz, 2H), 2.71 (d, J=8.2 Hz, 5H), 2.36-2.30 (m, 2H), 2.15 (t, J=7.6 Hz, 2H), 2.09-1.41 (m, AcOH, 46H), 1.37-1.29 (m, 4H), 1.16 (d, J=7.1 Hz, 3H), 0.85 (dd, J=20.7, 6.7 Hz, 6H).

SEQ ID NO: 4: Lys-Glu-Pro-Val-Pro-Gln-Ala-Lys (Acetate Salt)

High resolution mass spectrometry (TOF-HRMS), molecular formula: $C_{40}H_{69}N_{11}O_{12}$; m/z: 448.76653 ($[M+2H]^{2+}$), 896.52058 ($[M+H]^+$).

$^1$H NMR (600 MHz, DMSO-$d_6$) δ 4.56 (dd, J=9.0, 4.9 Hz, 1H), 4.39 (dd, J=8.3, 4.4 Hz, 1H), 4.31-4.24 (m, 3H), 4.13 (dd, J=9.1, 5.1 Hz, 2H), 3.78 (dd, J=7.9, 4.3 Hz, 1H), 3.67-3.51 (m, 4H), 2.75-2.70 (m, 4H), 2.38-2.29 (m, 2H), 2.14 (t, J=7.8 Hz, 2H), 2.04-1.47 (m, AcOH, 33H), 1.35-1.28 (m, 4H), 1.19 (d, J=7.2 Hz, 3H), 0.85 (dd, J=22.1, 6.8 Hz, 6H).

SEQ ID NO: 5: Pro-Arg-Lys-Val-Ala-Ala-Gln (Acetate Salt)

High resolution mass spectrometry (TOF-HRMS), molecular formula: $C_{33}H_{60}N_{12}O_9$; m/z: 385.24021 ($[M+2H]^{2+}$), 769.46971 ($[M+H]^+$).

$^1$H NMR (600 MHz, $D_2O$) δ 4.23-4.17 (m, 1H), 4.15-4.07 (m, 4H), 3.95 (dd, J=8.5, 4.8 Hz, 1H), 3.89 (d, J=7.7 Hz, 1H), 3.25-3.15 (m, 2H), 3.00 (t, J=7.0 Hz, 2H), 2.78 (t, J=7.7 Hz, 2H), 2.30-2.22 (m, 1H), 2.12-2.05 (m, 2H), 1.93-1.80 (m, 5H), 1.75 (s, AcOH, 10H), 1.62-1.40 (m, 8H), 1.19 (d, J=7.2 Hz, 8H), 0.73 (dd, J=6.7, 4.0 Hz, 6H).

SEQ ID NO: 6: Glu-Pro-Val-Pro-Gln-Ala-Lys (Acetate Salt)

High resolution mass spectrometry (TOF-HRMS), molecular formula: $C_{34}H_{57}N_9O_{11}$; m/z: 768.42641 ($[M+H]^+$).

$^1$H NMR (600 MHz, $D_2O$) δ 4.46 (dd, J=8.4, 6.4 Hz, 1H), 4.35-4.27 (m, 3H), 4.26-4.18 (m, 2H), 4.09 (dd, J=8.2, 5.1 Hz, 1H), 3.84-3.77 (m, 1H), 3.68-3.52 (m, 3H), 2.91 (t, J=7.5 Hz, 2H), 2.39 (t, J=7.2 Hz, 2H), 2.33 (t, J=7.6 Hz, 2H), 2.27-2.17 (m, 2H), 2.12-1.87 (m, AcOH, 13H), 1.83-1.72 (m, 3H), 1.66-1.57 (m, 3H), 1.32 (dd, J=11.8, 7.5 Hz, 5H), 0.92 (dd, J=12.6, 6.7 Hz, 6H).

SEQ ID NO: 7: Lys-Glu-Pro-Val (Acetate Salt)

High resolution mass spectrometry (TOF-HRMS), molecular formula: $C_{21}H_{37}N_5O_7$; m/z: 472.27768 ($[M+H]^+$).

$^1$H NMR (600 MHz, $D_2O$) δ 4.43 (dd, J=10.2, 4.0 Hz, 1H), 4.27 (dd, J=8.3, 5.3 Hz, 1H), 3.85-3.80 (m, 2H), 3.68-3.60 (m, 1H), 3.59-3.46 (m, 1H), 2.80 (t, J=7.6 Hz, 2H), 2.22-2.14 (m, 2H), 2.10-2.06 (m, 1H), 1.96-1.64 (m, AcOH, 11H), 1.52-1.47 (m, 2H), 1.29-1.22 (m, 2H), 0.71 (dd, J=15.3, 6.9 Hz, 6H).

SEQ ID NO: 8: Val-Ala-Ala-Gln (Acetate Salt)

High resolution mass spectrometry (Orbitrap-HRMS), molecular formula: $C_{16}H_{29}N_5O_6$; m/z: 388.2187 ($[M+H]^+$).

$^1$H NMR (600 MHz, $D_2O$) δ 4.25 (q, J=7.2 Hz, 1H), 4.17 (q, J=7.2 Hz, 1H), 4.05 (dd, J=8.5, 4.8 Hz, 1H), 3.67 (d, J=6.0 Hz, 1H), 2.23-2.14 (m, 2H), 2.13-2.05 (m, 1H), 2.04-1.95 (m, 1H), 1.85-1.76 (m, 1H), 1.28 (dd, J=7.2, 5.0 Hz, 6H), 0.90 (dd, J=10.3, 6.9 Hz, 6H).

SEQ ID NO: 9: Glu-Pro-Val-Pro (Acetate Salt)

High resolution mass spectrometry (TOF-HRMS), molecular formula: $C_{20}H_{32}N_4O_7$; 441.23562 ($[M+H]^+$).

$^1$H NMR (600 MHz, DMSO-$d_6$) δ 4.42 (dd, J=8.4, 4.6 Hz, 1H), 4.28 (t, J=8.3 Hz, 1H), 4.17 (dd, J=8.5, 4.7 Hz, 1H), 3.78 (dd, J=8.3, 4.2 Hz, 1H), 3.64-3.45 (m, 4H), 2.37-2.27 (m, 2H), 2.08-1.58 (m, AcOH, 16H), 0.87 (dd, J=25.7, 6.7 Hz, 6H).

SEQ ID NO: 10: Lys-Pro-Arg-Lys(Acetate Salt)

High resolution mass spectrometry (TOF-HRMS), molecular formula: $C_{23}H_{45}N_9O_5$; 264.68527 ($[M+2H]^{2+}$), 528.36210 ($[M+H]^+$).

$^1$H NMR (600 MHz, DMSO-$d_6$) δ 4.42 (dd, J=8.2, 5.2 Hz, 1H), 4.23 (t, J=6.7 Hz, 1H), 4.14 (dd, J=8.9, 5.2 Hz, 1H), 4.09 (d, J=7.9 Hz, 1H), 3.64 (dd, J=9.9, 6.6 Hz, 1H), 3.45-3.40 (m, 1H), 3.07 (s, 2H), 2.72 (t, J=6.3 Hz, 4H), 2.11-2.04 (m, 1H), 1.92-1.66 (m, AcOH, 18H), 1.56-1.48 (m, 8H), 1.45-1.38 (m, 2H), 1.33-1.29 (m, 2H).

SEQ ID NO: 11: Ala-Lys-Pro-Arg (Acetate Salt)

High resolution mass spectrometry (TOF-HRMS), molecular formula: $C_{20}H_{38}N_8O_5$; 236.15638 ($[M+2H]^{2+}$), 471.30462 ($[M+H]^+$).

$^1$H NMR (600 MHz, $D_2O$)) δ 4.55 (dd, J=8.3, 5.6 Hz, 1H), 4.34 (dd, J=8.4, 5.9 Hz, 1H), 4.09-3.96 (m, 2H), 3.82-3.74 (m, 1H), 3.64-3.55 (m, 1H), 3.12 (t, J=6.9 Hz, 2H), 2.93 (t, J=7.6 Hz, 2H), 2.28-2.20 (m, 1H), 2.04-1.83 (m, 3H), 1.82 (s, AcOH, 6H), 1.79-1.60 (m, 6H), 1.58-1.51 (m, 2H), 1.42 (d, J=7.1 Hz, 5H).

SEQ ID NO: 12: Pro-Val-Pro-Gln (Acetate Salt)

High resolution mass spectrometry (TOF-HRMS), molecular formula: $C_{20}H_{33}N_5O_6$; m/z: 440.25122 ($[M+H]^+$).

$^1$H NMR (600 MHz, $D_2O$) δ 4.33-4.18 (m, 3H), 3.97 (dd, J=8.9, 4.8 Hz, 1H), 3.74-3.65 (m, 1H), 3.53-3.46 (m, 1H), 3.25-3.16 (m, 2H), 2.29-2.22 (m, 1H), 2.17-2.10 (m, 3H), 1.99-1.66 (m, AcOH, 12H), 0.82 (d, J=6.8 Hz, 3H), 0.76 (d, J=6.7 Hz, 3H).

SEQ ID NO: 13: Val-Pro-Gln-Ala (Acetate Salt)

High resolution mass spectrometry (TOF-HRMS), molecular formula: $C_{18}H_{31}N_5O_6$; m/z: 414.23575 ($[M+H]^+$).

$^1$H NMR (600 MHz, $D_2O$) δ 4.37 (t, J=7.5 Hz, 1H), 4.15 (dd, J=8.6, 6.0 Hz, 1H), 4.07 (d, J=5.5 Hz, 1H), 4.03 (t, J=7.2 Hz, 1H), 3.68-3.61 (m, 1H), 3.55-3.48 (m, 1H), 2.35-2.26 (m, 2H), 2.26-2.15 (m, 2H), 2.04-1.74 (m, AcOH, 7H), 1.22 (d, J=7.2 Hz, 3H), 0.98 (d, J=7.0 Hz, 3H), 0.87 (d, J=6.8 Hz, 3H).

SEQ ID NO: 14: Pro-Gln-Ala-Lys (Acetate Salt)

High resolution mass spectrometry (TOF-HRMS), molecular formula: $C_{19}H_{34}N_6O_6$; m/z: 222.13480 ($[M+2H]^{2+}$), 443.26183 ($[M+H]^+$).

$^1$H NMR (600 MHz, $D_2O$) δ 4.28 (dd, J=8.7, 6.1 Hz, 1H), 4.25-4.15 (m, 2H), 4.01 (dd, J=8.1, 5.2 Hz, 1H), 3.34-3.22 (m, 2H), 2.86 (t, J=7.5 Hz, 2H), 2.37-2.29 (m, 1H), 2.26 (t, J=7.6 Hz, 2H), 2.00-1.84 (m, 5H), 1.73-1.64 (m, 1H), 1.62-1.50 (m, 3H), 1.30-1.24 (m, 5H).

SEQ ID NO: 15: Arg-Lys-Val-Ala (Acetate Salt)

High resolution mass spectrometry (TOF-HRMS), molecular formula: $C_{20}H_{40}N_8O_5$; m/z: 237.16465 ($[M+2H]^{2+}$), 473.32087 ($[M+H]^+$).

$^1$H NMR (600 MHz, $D_2O$) δ 4.28 (t, J=7.3 Hz, 1H), 4.00-3.94 (m, 2H), 3.90 (t, J=6.4 Hz, 1H), 3.07 (t, J=7.0 Hz, 2H), 2.85 (t, J=7.6 Hz, 2H), 2.01-1.92 (m, 1H), 1.80-1.75 (m, AcOH, 8H), 1.73-1.59 (m, 2H), 1.59-1.40 (m, 4H), 1.35-1.22 (m, 2H), 1.19 (d, J=7.2 Hz, 3H), 0.81 (t, J=6.9 Hz, 6H).

SEQ ID NO: 16: Lys-Val-Ala-Ala (Acetate Salt)

High resolution mass spectrometry (TOF-HRMS), molecular formula: $C_{17}H_{33}N_5O_5$; m/z: 388.25660 ($[M+H]^+$).

$^1$H NMR (600 MHz, $D_2O$) δ 4.18 (q, J=7.1 Hz, 1H), 4.03-3.91 (m, 3H), 2.87 (t, J=7.7 Hz, 2H), 1.98-1.89 (m, 1H), 1.83-1.74 (m, AcOH, 6H), 1.60-1.53 (m, 2H), 1.36-1.27 (m, 2H), 1.26 (d, J=7.2 Hz, 3H), 1.19 (d, J=7.2 Hz, 3H), 0.83 (d, J=6.8 Hz, 6H).

SEQ ID NO: 17: Gln-Ala-Lys-Pro (Acetate Salt)

High resolution mass spectrometry (TOF-HRMS), molecular formula: $C_{19}H_{34}N_6O_6$; m/z: 443.26161 ($[M+H]^+$).

$^1$H NMR (600 MHz, $D_2O$) δ 4.48 (dd, J=8.2, 5.6 Hz, 1H), 4.26-4.20 (m, 1H), 4.10 (dd, J=8.5, 5.4 Hz, 1H), 3.91 (t, J=6.6 Hz, 1H), 3.68-3.61 (m, 1H), 3.55-3.43 (m, 1H), 2.88 (t, J=7.5 Hz, 2H), 2.39-2.27 (m, 2H), 2.15-1.96 (m, 3H), 1.92-1.69 (m, 8H), 1.66-1.49 (m, 3H), 1.43-1.29 (m, 2H), 1.28-1.22 (m, 3H).

SEQ ID NO: 18: Pro-Arg-Lys-Val (Acetate Salt)

High resolution mass spectrometry (TOF-HRMS), molecular formula: $C_{22}H_{42}N_8O_5$; m/z: 250.17158 ($[M+2H]^{2+}$), 499.33464 ($[M+H]^+$).

$^1$H NMR (600 MHz, $D_2O$) δ 4.27 (dd, J=8.7, 6.0 Hz, 1H), 4.24-4.17 (m, 2H), 3.88 (d, J=6.2 Hz, 1H), 3.33-3.20 (m, 2H), 3.09-3.02 (m, 2H), 2.85 (t, J=7.5 Hz, 2H), 2.37-2.28 (m, 1H), 1.98-1.86 (m, 4H), 1.78 (s, AcOH, 6H), 1.72-1.42 (m, 8H), 1.38-1.23 (m, 2H), 0.75 (dd, J=11.2, 6.8 Hz, 6H).

SEQ ID NO: 19: Ala-Glu-Pro-Val-Pro-Gln-Ala-Lys-Pro-Arg-Lys-Val-Ala-Ala-Gln (Acetate Salt)

High resolution mass spectrometry (TOF-HRMS), molecular formula: $C_{70}H_{120}N_{22}O_{20}$; m/z: 530.64499 ($[M+3H]^{3+}$), 795.46224 ($[M+2H]^{2+}$), 1589.91350 ($[M+H]^+$).

$^1$H NMR (600 MHz, $D_2O$) δ 4.53-4.43 (m, 2H), 4.33 (dd, J=8.3, 6.0 Hz, 1H), 4.27 (t, J=7.7 Hz, 3H), 4.24-4.12 (m, 6H), 4.06-3.94 (m, 3H), 3.77 (q, J=7.6 Hz, 1H), 3.73-3.67 (m, 2H), 3.63-3.53 (m, 2H), 3.51 (q, J=7.6 Hz, 1H), 3.08 (t, J=6.9 Hz, 2H), 2.91-2.83 (m, 4H), 2.29 (t, J=7.6 Hz, 2H), 2.26-2.12 (m, 7H), 2.03-1.46 (m, AcOH, 38H), 1.39 (d, J=7.1 Hz, 4H), 1.36-1.30 (m, 2H), 1.30-1.22 (m, 10H), 0.92-0.77 (m, 12H).

SEQ ID NO: 20: Lys-Ala-Pro-Val-Pro-Gln-Ala-Lys-Pro-Arg-Lys-Val-Ala-Ala-Gln (Acetate Salt)

High resolution mass spectrometry (TOF-HRMS), molecular formula: $C_{71}H_{125}N_{23}O_{18}$; m/z: 530.32804 ($[M+3H]^{3+}$), 794.98683 ($[M+2H]^{2+}$), 1588.96546 ($[M+H]^+$).

$^1$H NMR (600 MHz, $D_2O$) δ 4.51 (q, J=7.1 Hz, 1H), 4.48-4.43 (m, 1H), 4.31-4.25 (m, 3H), 4.24-4.11 (m, 6H), 4.03 (dd, J=8.4, 4.9 Hz, 1H), 3.98 (d, J=7.6 Hz, 1H), 3.87 (t, J=6.7 Hz, 1H), 3.79-3.67 (m, 3H), 3.60-3.47 (m, 3H), 3.08 (t, J=6.9 Hz, 2H), 2.91-2.83 (m, 6H), 2.28 (t, J=7.6 Hz, 2H), 2.21-2.13 (m, 5H), 2.03-1.64 (m, AcOH, 33H), 1.64-1.47 (m, 11H), 1.44-1.28 (m, 6H), 1.28-1.21 (m, 12H), 0.89-0.76 (m, 12H).

SEQ ID NO: 21: Lys-Glu-Ala-Val-Pro-Gln-Ala-Lys-Pro-Arg-Lys-Val-Ala-Ala-Gln (Acetate Salt)

High resolution mass spectrometry (TOF-HRMS), molecular formula: $C_{71}H_{125}N_{23}O_{20}$; m/z: 540.99125 ($[M+3H]^{3+}$), 810.98235 ($[M+2H]^{2+}$), 1620.94722 ($[M+H]^+$).

$^1$H NMR (600 MHz, $D_2O$) δ 4.45 (dd, J=9.4, 4.9 Hz, 1H), 4.30-4.24 (m, 3H), 4.24-4.11 (m, 8H), 4.02 (dd, J=8.4, 4.9 Hz, 1H), 3.97 (d, J=7.6 Hz, 1H), 3.89 (t, J=6.7 Hz, 1H), 3.79-3.66 (m, 2H), 3.60-3.47 (m, 2H), 3.08 (t, J=6.9 Hz, 2H), 2.91-2.83 (m, 6H), 2.28 (t, J=7.6 Hz, 2H), 2.22-2.12 (m, 6H), 2.02-1.46 (m, AcOH, 41H), 1.43-1.28 (m, 6H), 1.28-1.20 (m, 12H), 0.88-0.75 (m, 12H).

SEQ ID NO: 22: Lys-Glu-Pro-Val-Ala-Gln-Ala-Lys-Pro-Arg-Lys-Val-Ala-Ala-Gln (Acetate Salt)

High resolution mass spectrometry (TOF-HRMS), molecular formula: $C_{71}H_{125}N_{23}O_{20}$; m/z: 540.99088 ($[M+3H]^{3+}$), 810.98168 ($[M+2H]^{2+}$), 1620.95237 ($[M+H]^+$).

$^1$H NMR (600 MHz, $D_2O$) δ 4.51 (dd, J=9.6, 4.4 Hz, 1H), 4.46 (dd, J=9.4, 4.8 Hz, 1H), 4.35 (dd, J=8.4, 5.8 Hz, 1H), 4.28 (dd, J=8.3, 6.1 Hz, 1H), 4.25-4.13 (m, 7H), 4.03 (dd, J=8.3, 4.9 Hz, 1H), 3.98 (d, J=7.6 Hz, 1H), 3.94-3.88 (m, 2H), 3.75-3.67 (m, 2H), 3.63-3.56 (m, 1H), 3.51 (q, J=7.3 Hz, 1H), 3.09 (t, J=6.9 Hz, 2H), 2.91-2.83 (m, 6H), 2.29-2.21 (m, 4H), 2.21-2.13 (m, 4H), 2.03-1.65 (m, AcOH, 31H), 1.64-1.46 (m, 11H), 1.45-1.28 (m, 6H), 1.28-1.22 (m, 12H), 0.89-0.78 (m, 12H).

SEQ ID NO: 23: Lys-Glu-Pro-Val-Pro-Ala-Ala-Lys-Pro-Arg-Lys-Val-Ala-Ala-Gln (Acetate Salt)

High resolution mass spectrometry (Orbitrap-HRMS), molecular formula: $C_{71}H_{124}N_{22}O_{19}$; m/z: 398.24191 ($[M+4H]^{4+}$), 530.65344 ($[M+3H]^{3+}$), 795.97791 ($[M+2H]^{2+}$).

$^{1}$H NMR (600 MHz, $D_2O$) δ 4.51 (dd, J=9.6, 4.4 Hz, 1H), 4.44 (dd, J=9.4, 4.9 Hz, 1H), 4.33 (dd, J=8.4, 5.8 Hz, 1H), 4.31-4.08 (m, 9H), 4.03 (dd, J=8.4, 4.9 Hz, 1H), 3.97 (d, J=7.6 Hz, 1H), 3.92-3.87 (m, 1H), 3.79-3.73 (m, 1H), 3.73-3.66 (m, 2H), 3.62-3.52 (m, 2H), 3.51-3.46 (m, 1H), 3.07 (t, J=6.9 Hz, 2H), 2.90-2.81 (m, 6H), 2.29-2.21 (m, 2H), 2.21-2.10 (m, 5H), 2.02-1.64 (m, AcOH, 37H), 1.64-1.45 (m, 11H), 1.44-1.27 (m, 6H), 1.27-1.20 (m, 12H), 0.91-0.74 (m, 12H).

SEQ ID NO: 24: Lys-Glu-Pro-Val-Pro-Gln-Ala-Ala-Pro-Arg-Lys-Val-Ala-Ala-Gln (Acetate Salt)

High resolution mass spectrometry (Orbitrap-HRMS), molecular formula: $C_{70}H_{120}N_{22}O_{20}$; m/z: 398.23245 ([M+4H]$^{4+}$), 530.64075 ([M+3H]$^{3+}$), 795.45752 ([M+2H]$^{2+}$).

$^{1}$H NMR (600 MHz, $D_2O$) δ 4.51 (dd, J=9.7, 4.4 Hz, 1H), 4.45 (q, J=7.1 Hz, 1H), 4.33 (dd, J=8.4, 5.8 Hz, 1H), 4.31-4.24 (m, 3H), 4.23-4.12 (m, 6H), 4.03 (dd, J=8.4, 4.8 Hz, 1H), 3.97 (d, J=7.6 Hz, 1H), 3.92-3.87 (m, 1H), 3.79-3.73 (m, 1H), 3.73-3.64 (m, 2H), 3.62-3.48 (m, 3H), 3.08 (t, J=6.9 Hz, 2H), 2.91-2.83 (m, 4H), 2.32-2.21 (m, 4H), 2.20-2.11 (m, 5H), 2.03-1.71 (m, AcOH, 32H), 1.71-1.45 (m, 10H), 1.37-1.27 (m, 4H), 1.27-1.17 (m, 12H), 0.90-0.76 (m, 12H).

SEQ ID NO: 25: Lys-Glu-Pro-Ala-Pro-Gln-Ala-Lys-Pro-Arg-Lys-Val-Ala-Ala-Gln (Acetate Salt)

High resolution mass spectrometry (Orbitrap-HRMS), molecular formula: $C_{71}H_{123}N_{23}O_{20}$; m/z: 405.48935 ([M+4H]$^{4+}$), 540.31677 ([M+3H]$^{3+}$), 809.97144 ([M+2H]$^{2+}$).

$^{1}$H NMR (600 MHz, $D_2O$) δ 4.51 (dd, J=9.5, 4.4 Hz, 1H), 4.48-4.41 (m, 2H), 4.32-4.25 (m, 3H), 4.21 (dd, J=8.1, 6.7 Hz, 1H), 4.19-4.12 (m, 5H), 4.02 (dd, J=8.4, 4.9 Hz, 1H), 3.97 (d, J=7.6 Hz, 1H), 3.92-3.85 (m, 1H), 3.74-3.64 (m, 3H), 3.60-3.46 (m, 3H), 3.07 (t, J=6.9 Hz, 2H), 2.90-2.83 (m, 6H), 2.30-2.20 (m, 4H), 2.20-2.12 (m, 5H), 2.02-1.45 (m, AcOH, 48H), 1.43-1.27 (m, 6H), 1.27-1.21 (m, 12H), 0.80 (dd, J=6.8, 4.4 Hz, 6H).

SEQ ID NO: 26: Lys-Glu-Pro-Val-Pro-Gln-Ala-Lys-Ala-Arg-Lys-Val-Ala-Ala-Gln (Acetate Salt)

High resolution mass spectrometry (Orbitrap-HRMS), molecular formula: $C_{71}H_{125}N_{23}O_{20}$; m/z: 405.99350 ([M+4H]$^{4+}$), 540.98883 ([M+3H]$^{3+}$), 810.97961 ([M+2H]$^{2+}$).

$^{1}$H NMR (600 MHz, $D_2O$) δ 4.51 (dd, J=9.6, 4.4 Hz, 1H), 4.33 (dd, J=8.4, 5.8 Hz, 1H), 4.31-4.23 (m, 2H), 4.23-4.09 (m, 8H), 4.03 (dd, J=8.4, 4.9 Hz, 1H), 3.97 (d, J=7.6 Hz, 1H), 3.93-3.86 (m, 1H), 3.81-3.66 (m, 2H), 3.62-3.52 (m, 2H), 3.07 (t, J=6.9 Hz, 2H), 2.86 (m, 6H), 2.31-2.11 (m, 8H), 2.03-1.41 (m, AcOH, 48H), 1.40-1.27 (m, 6H), 1.25 (dd, J=13.7, 7.3 Hz, 12H), 0.90-0.76 (m, 12H).

SEQ ID NO: 27: Lys-Glu-Pro-Val-Pro-Gln-Ala-Lys-Pro-Ala-Lys-Val-Ala-Ala-Gln (Acetate Salt)

High resolution mass spectrometry (Orbitrap-HRMS), molecular formula: $C_{70}H_{120}N_{20}O_{20}$; m/z: 391.23177 ([M+4H]$^{4+}$), 781.45496 ([M+2H]$^{2+}$).

$^{1}$H NMR (600 MHz, $D_2O$) δ 4.52-4.43 (m, 2H), 4.33 (dd, J=8.4, 5.8 Hz, 1H), 4.31-4.22 (m, 3H), 4.21-4.10 (m, 6H), 4.02 (dd, J=8.5, 4.8 Hz, 1H), 3.96 (d, J=7.7 Hz, 1H), 3.92-3.84 (m, 1H), 3.81-3.73 (m, 1H), 3.73-3.65 (m, 2H), 3.61-3.52 (m, 2H), 3.52-3.45 (m, 1H), 2.91-2.81 (m, 6H), 2.30-2.10 (m, 9H), 2.02-1.62 (m, AcOH, 31H), 1.62-1.51 (m, 8H), 1.41-1.27 (m, 6H), 1.27-1.20 (m, 12H), 0.90-0.75 (m, 12H).

SEQ ID NO: 28: Lys-Glu-Pro-Val-Pro-Gln-Ala-Lys-Pro-Arg-Ala-Val-Ala-Ala-Gln (Acetate Salt)

High resolution mass spectrometry (Orbitrap-HRMS), molecular formula: $C_{70}H_{120}N_{22}O_{20}$; m/z: 398.23303 ([M+4H]$^{4+}$), 530.64142 ([M+3H]$^{3+}$), 795.45850 ([M+2H]$^{2+}$).

$^{1}$H NMR (600 MHz, $D_2O$) δ 4.52-4.42 (m, 2H), 4.33 (dd, J=8.4, 5.8 Hz, 1H), 4.30-4.24 (m, 3H), 4.23-4.09 (m, 6H), 4.02 (dd, J=8.5, 4.8 Hz, 1H), 3.95 (d, J=7.5 Hz, 1H), 3.92-3.85 (m, 1H), 3.79-3.73 (m, 1H), 3.72-3.67 (m, 2H), 3.62-3.42 (m, 3H), 3.08 (t, J=6.9 Hz, 2H), 2.87 (t, J=7.6 Hz, 4H), 2.30-2.25 (m, 2H), 2.24-2.10 (m, 7H), 2.02-1.65 (m, AcOH, 29H), 1.64-1.48 (m, 8H), 1.42-1.29 (m, 4H), 1.28-1.19 (m, 12H), 0.90-0.75 (m, 12H).

SEQ ID NO: 29: Lys-Glu-Pro-Val-Pro-Gln-Ala-Lys-Pro-Arg-Lys-Ala-Ala-Ala-Gln (Acetate Salt)

High resolution mass spectrometry (Orbitrap-HRMS), molecular formula: $C_{71}H_{123}N_{23}O_{20}$; m/z: 405.48969 ([M+4H]$^{4+}$), 540.31714 ([M+3H]$^{3+}$), 809.97205 ([M+2H]$^{2+}$).

$^{1}$H NMR (600 MHz, $D_2O$) δ 4.49 (dd, J=9.6, 4.3 Hz, 1H), 4.45 (dd, J=9.3, 4.9 Hz, 1H), 4.33 (dd, J=8.4, 5.8 Hz, 1H), 4.29-4.24 (m, 3H), 4.19-4.13 (m, 7H), 4.02 (dd, J=8.4, 4.8 Hz, 1H), 3.89 (t, J=6.8 Hz, 1H), 3.79-3.66 (m, 3H), 3.61-3.47 (m, 3H), 3.08 (t, J=6.9 Hz, 2H), 2.86 (q, J=8.0 Hz, 6H), 2.28 (t, J=7.6 Hz, 2H), 2.23-2.13 (m, 7H), 2.02-1.46 (m, AcOH, 47H), 1.42-1.18 (m, 20H), 0.85 (dd, J=14.2, 6.7 Hz, 6H).

SEQ ID NO: 30: Lys-Glu-Pro-Val-Pro-Gln-Ala-Lys-Pro-Arg-Lys-Val-Ala-Ala-Ala (Acetate Salt)

High resolution mass spectrometry (TOF-HRMS), molecular formula: $C_{71}H_{124}N_{22019}$; m/z: 398.24493 ([M+4H]$^{4+}$), 530.65551 ([M+3H]$^{3+}$), 795.47815 ([M+2H]$^{2+}$), 1589.94194 ([M+H]$^{+}$).

$^{1}$H NMR (600 MHz, $D_2O$) δ 4.51 (dd, J=9.6, 4.4 Hz, 1H), 4.46 (dd, J=9.4, 4.9 Hz, 1H), 4.34 (dd, J=8.4, 5.8 Hz, 1H), 4.31-4.24 (m, 3H), 4.24-4.20 (m, 1H), 4.20-4.09 (m, 5H), 4.02-3.96 (m, 2H), 3.93-3.86 (m, 1H), 3.80-3.74 (m, 1H), 3.74-3.67 (m, 2H), 3.63-3.43 (m, 3H), 3.08 (t, J=6.9 Hz, 2H), 2.91-2.82 (m, 6H), 2.31-2.12 (m, 7H), 2.01-1.65 (m, AcOH, 34H), 1.64-1.46 (m, 11H), 1.35 (dd, J=16.0, 8.1 Hz, 6H), 1.27-1.20 (m, 12H), 0.92-0.77 (m, 12H).

SEQ ID NO: 31: Lys-Glu-Gly-Val-Pro-Gln-Ala-Lys-Pro-Arg-Lys-Val-Ala-Ala-Gln (Acetate Salt)

High resolution mass spectrometry (TOF-HRMS), molecular formula: $C_{70}H_{123}N_{23}O_{20}$; m/z: 402.49240 ([M+4H]$^{4+}$), 536.31955 ([M+3H]$^{3+}$), 803.97442 ([M+2H]$^{2+}$), 1606.91471 ([M+H]$^{+}$).

$^{1}$H NMR (600 MHz, $D_2O$) δ 4.45 (dd, J=9.4, 4.9 Hz, 1H), 4.32 (d, J=8.1 Hz, 1H), 4.30-4.25 (m, 2H), 4.24-4.19 (m, 2H), 4.19-4.11 (m, 5H), 4.02 (dd, J=8.4, 4.9 Hz, 1H), 3.97 (d, J=7.6 Hz, 1H), 3.91-3.84 (m, 2H), 3.82-3.73 (m, 2H), 3.69 (q, J=7.7, 7.0 Hz, 1H), 3.59-3.52 (m, 1H), 3.52-3.46 (m, 1H), 3.07 (t, J=6.9 Hz, 2H), 2.90-2.82 (m, 6H), 2.28 (t, J=7.6 Hz, 2H), 2.23-2.12 (m, 6H), 2.02-1.64 (m, AcOH, 35H), 1.63-1.45 (m, 11H), 1.44-1.27 (m, 6H), 1.27-1.21 (m, 9H), 0.88-0.73 (m, 12H).

SEQ ID NO: 32: Lys-Glu-Pro-Val-Gly-Gln-Ala-Lys-Pro-Arg-Lys-Val-Ala-Ala-Gln (Acetate Salt)

High resolution mass spectrometry (TOF-HRMS), molecular formula: $C_{70}H_{123}N_{23}O_{20}$; m/z: 402.49278 ([M+4H]$^{4+}$), 536.31975 ([M+3H]$^{3+}$), 803.97422 ([M+2H]$^{2+}$), 1606.92969 ([M+H]$^{+}$).

$^{1}$H NMR (600 MHz, $D_2O$) δ 4.51 (dd, J=9.7, 4.4 Hz, 1H), 4.46 (dd, J=9.4, 4.9 Hz, 1H), 4.36 (dd, J=8.3, 5.9 Hz, 1H), 4.28 (dd, J=8.3, 6.1 Hz, 1H), 4.24-4.14 (m, 6H), 4.03 (dd, J=8.3, 4.9 Hz, 1H), 3.97 (dd, J=10.0, 7.5 Hz, 2H), 3.90 (t, J=6.8 Hz, 1H), 3.87-3.78 (m, 2H), 3.76-3.67 (m, 2H), 3.61-3.54 (m, 1H), 3.54-3.47 (m, 1H), 3.08 (t, J=6.9 Hz, 2H), 2.91-2.83 (m, 6H), 2.26-2.13 (m, 8H), 2.03-1.87 (m, 9H), 1.87-1.45 (m, AcOH, 33H), 1.44-1.28 (m, 6H), 1.26 (dd, J=18.4, 7.2 Hz, 9H), 0.89-0.79 (m, 12H).

SEQ ID NO: 33: Lys-Glu-Pro-Val-Pro-Gln-Ala-Lys-Gly-Arg-Lys-Val-Ala-Ala-Gln (Acetate Salt)

High resolution mass spectrometry (Orbitrap-HRMS), molecular formula: $C_{70}H_{123}N_{23}O_{20}$; m/z: 402.48917 ([M+4H]$^{4+}$), 536.31647 ([M+3H]$^{3+}$), 803.97101 ([M+2H]$^{2+}$).

$^{1}$H NMR (600 MHz, $D_2O$) δ 4.51 (dd, J=9.6, 4.4 Hz, 1H), 4.34 (dd, J=8.4, 5.8 Hz, 1H), 4.31-4.11 (m, 9H), 4.03 (dd, J=8.4, 4.9 Hz, 1H), 3.97 (d, J=7.6 Hz, 1H), 3.92-3.86 (m, 1H), 3.85-3.74 (m, 3H), 3.74-3.66 (m, 1H), 3.62-3.52 (m, 2H), 3.06 (t, J=7.0 Hz, 2H), 2.91-2.83 (m, 6H), 2.31-2.11 (m, 8H), 2.03-1.43 (m, AcOH, 45H), 1.40-1.27 (m, 6H), 1.27-1.23 (m, 9H), 0.91-0.77 (m, 12H).

SEQ ID NO: 34: Lys-Glu-Pro-Val-Gly-Gln-Ala-Lys-Gly-Arg-Lys-Val-Ala-Ala-Gln (Acetate Salt)

High resolution mass spectrometry (Orbitrap-HRMS), molecular formula: $C_{67}H_{119}N_{23}O_{20}$; m/z: 392.48178 ([M+4H]$^{4+}$), 522.97314 ([M+3H]$^{3+}$), 784.45752 ([M+2H]$^{2+}$).

$^{1}$H NMR (600 MHz, $D_2O$) δ 4.51 (dd, J=9.6, 4.4 Hz, 1H), 4.35 (dd, J=8.3, 5.9 Hz, 1H), 4.25-4.12 (m, 7H), 4.03 (dd, J=8.4, 4.8 Hz, 1H), 3.96 (dd, J=10.6, 7.5 Hz, 2H), 3.92-3.86 (m, 1H), 3.85-3.77 (m, 4H), 3.75-3.68 (m, 1H), 3.60-3.53 (m, 1H), 3.06 (t, J=7.0 Hz, 2H), 2.92-2.83 (m, 6H), 2.28-2.12 (m, 7H), 2.05-1.41 (m, AcOH, 42H), 1.40-1.27 (m, 6H), 1.27-1.24 (m, 9H), 0.85 (dd, J=11.0, 6.7 Hz, 6H), 0.80 (dd, J=6.8, 5.1 Hz, 6H).

SEQ ID NO: 35: Lys-Glu-Gly-Val-Gly-Gln-Ala-Lys-Gly-Arg-Lys-Val-Ala-Ala-Gln (Acetate Salt)

High resolution mass spectrometry (Orbitrap-HRMS), molecular formula: $C_{64}H_{115}N_{23}O_{20}$; m/z: 382.47363 ([M+4H]$^{4+}$), 509.62903 ([M+3H]$^{3+}$), 763.93982 ([M+2H]$^{2+}$).

$^{1}$H NMR (600 MHz, $D_2O$) δ 4.27-4.13 (m, 8H), 4.05-4.00 (m, 2H), 3.97 (d, J=7.6 Hz, 1H), 3.93-3.87 (m, 2H), 3.85-3.76 (m, 5H), 3.06 (t, J=7.0 Hz, 2H), 2.90-2.83 (m, 6H), 2.24-2.12 (m, 6H), 2.02-1.41 (m, AcOH, 40H), 1.39-1.27 (m, 6H), 1.27-1.22 (m, 9H), 0.85-0.76 (m, 12H).

SEQ ID NO: 36: Lys-Glu-Gly-Val-Pro-Gln-Ala-Lys-Gly-Arg-Lys-Val-Ala-Ala-Gln (Acetate Salt)

High resolution mass spectrometry (Orbitrap-HRMS), molecular formula: $C_{67}H_{119}N_{23}O_{20}$; m/z: 392.48172 ([M+4H]$^{4+}$), 522.97314 ([M+3H]$^{3+}$), 783.95605 ([M+2H]$^{2+}$).

$^{1}$H NMR (600 MHz, $D_2O$) δ 4.32 (d, J=8.0 Hz, 1H), 4.28 (dd, J=8.2, 6.7 Hz, 1H), 4.25-4.12 (m, 8H), 4.03 (dd, J=8.4, 4.8 Hz, 1H), 3.97 (d, J=7.6 Hz, 1H), 3.92-3.83 (m, 2H), 3.83-3.73 (m, 4H), 3.60-3.53 (m, 1H), 3.06 (t, J=7.0 Hz, 2H), 2.91-2.83 (m, 6H), 2.28 (t, J=7.5 Hz, 2H), 2.24-2.12 (m, 5H), 2.02-1.42 (m, AcOH, 43H), 1.41-1.27 (m, 6H), 1.27-1.22 (m, 9H), 0.91-0.72 (m, 12H).

SEQ ID NO: 37: Lys-Glu-Gly-Val-Gly-Gln-Ala-Lys-Pro-Arg-Lys-Val-Ala-Ala-Gln (Acetate Salt)

High resolution mass spectrometry (Orbitrap-HRMS), molecular formula: $C_{67}H_{11}N_{23}O_{20}$; m/z: 392.48172 ([M+4H]$^{4+}$), 522.97314 ([M+3H]$^{3+}$), 783.95605 ([M+2H]$^{2+}$).

$^{1}$H NMR (600 MHz, $D_2O$) δ 4.44 (dd, J=9.4, 4.9 Hz, 1H), 4.29-4.12 (m, 8H), 4.04-3.99 (m, 2H), 3.96 (d, J=7.6 Hz, 1H), 3.91-3.82 (m, 3H), 3.81 (s, 2H), 3.72-3.65 (m, 1H), 3.52-3.44 (m, 1H), 3.06 (t, J=6.9 Hz, 2H), 2.89-2.81 (m, 6H), 2.23-2.12 (m, 7H), 2.01-1.45 (m, AcOH, 43H), 1.42-1.26 (m, 6H), 1.26-1.20 (m, 9H), 0.83-0.77 (m, 12H).

SEQ ID NO: 38: Glu-Pro-Val-Pro-Gln-Ala-Lys-Pro-Arg-Lys (Acetate Salt)

High resolution mass spectrometry (Orbitrap-HRMS), molecular formula: $C_{51}H_{88}N_{16}O_{14}$; m/z: 383.89569 ([M+3H]$^{3+}$), 575.33978 ([M+2H]$^{2+}$).

$^{1}$H NMR (600 MHz, $D_2O$) δ 4.45 (dd, J=9.2, 5.0 Hz, 1H), 4.39 (dd, J=8.3, 6.4 Hz, 1H), 4.29-4.21 (m, 4H), 4.19-4.12 (m, 3H), 4.01 (dd, J=7.8, 5.5 Hz, 1H), 3.78-3.73 (m, 1H), 3.72-3.67 (m, 1H), 3.61-3.48 (m, 4H), 3.08 (t, J=6.8 Hz, 2H), 2.88-2.83 (m, 4H), 2.30-2.26 (m, 4H), 2.20-2.13 (m, 3H), 2.08-1.46 (m, AcOH, 38H), 1.39-1.22 (m, 7H), 0.86 (dd, J=10.3, 6.7 Hz, 6H).

SEQ ID NO: 39: Pro-Val-Pro-Gln-Ala (Acetate Salt)

High resolution mass spectrometry (Orbitrap-HRMS), molecular formula: $C_{23}H_{38}N_6O_7$; m/z: 511.2871 ([M+H]$^{+}$).

$^{1}$H NMR (600 MHz, $D_2O$) δ 4.41 (d, J=7.3 Hz, 1H), 4.38-4.32 (m, 2H), 4.20 (dd, J=8.7, 5.9 Hz, 1H), 4.11-4.04 (m, 1H), 3.85-3.77 (m, 1H), 3.62 (dt, J=10.3, 7.2 Hz, 1H), 3.39-3.29 (m, 2H), 2.39-2.31 (m, 3H), 2.28-2.20 (m, 1H), 2.08-1.90 (m, AcOH, 10H), 1.86-1.80 (m, 1H), 1.26 (d, J=7.3 Hz, 3H), 0.94 (d, J=6.8 Hz, 3H), 0.88 (d, J=6.8 Hz, 3H).

SEQ ID NO: 40: Pro-Val-Pro-Glu-Ala (Acetate Salt)

High resolution mass spectrometry (Orbitrap-HRMS), molecular formula: $C_{23}H_{37}N_5O_8$; m/z: 512.27081 ([M+H]$^{+}$).

$^{1}$H NMR (600 MHz, $D_2O$) δ 4.41 (d, J=7.3 Hz, 1H), 4.38-4.32 (m, 2H), 4.23 (dd, J=8.9, 5.6 Hz, 1H), 4.13-4.09 (m, 1H), 3.86-3.76 (m, 1H), 3.62 (dt, J=10.2, 7.2 Hz, 1H), 3.38-3.28 (m, 2H), 2.43-2.35 (m, 3H), 2.26-2.16 (m, 1H), 2.12-1.72 (m, AcOH, 12H), 1.28 (d, J=7.2 Hz, 3H), 0.94 (d, J=6.8 Hz, 3H), 0.87 (d, J=6.8 Hz, 3H).

SEQ ID NO: 41: Pro-Val-Pro-Ile-Ala (Acetate Salt)

High resolution mass spectrometry (Orbitrap-HRMS), molecular formula: $C_{24}H_{41}N_5O_6$; m/z: 496.31158 ([M+H]$^{+}$).

$^{1}$H NMR (600 MHz, $D_2O$) δ 4.36-4.27 (m, 3H), 4.03 (q, J=7.2 Hz, 1H), 3.98 (d, J=7.8 Hz, 1H), 3.79-3.72 (m, 1H), 3.60-3.53 (m, 1H), 3.34-3.21 (m, 2H), 2.36-2.25 (m, 1H), 2.21-2.12 (m, 1H), 2.03-1.96 (m, 1H), 1.96-1.81 (m, AcOH, 7H), 1.80-1.69 (m, 2H), 1.43-1.33 (m, 1H), 1.20 (d, J=7.2 Hz, 3H), 1.13-1.02 (m, 1H), 0.88 (d, J=6.8 Hz, 3H), 0.85-0.80 (m, 6H), 0.80-0.77 (m, 1H), 0.74 (t, J=7.4 Hz, 3H).

SEQ ID NO: 42: Pro-Val-Pro-Ala

High resolution mass spectrometry (Orbitrap-HRMS), molecular formula: $C_{18}H_{30}N_4O_5$; m/z: 383.22791 ([M+H]$^{+}$).

$^{1}$H NMR (600 MHz, $D_2O$) δ 4.36 (d, J=7.2 Hz, 1H), 4.30 (dd, J=8.5, 6.3 Hz, 1H), 4.24 (dd, J=8.1, 6.5 Hz, 1H), 4.00 (q, J=7.2 Hz, 1H), 3.79-3.72 (m, 1H), 3.60-3.52 (m, 1H), 3.31-3.23 (m, 2H), 2.33-2.26 (m, 1H), 2.20-2.13 (m, 1H), 2.09-1.69 (m, AcOH, 10H), 1.21 (d, J=7.3 Hz, 3H), 0.88 (d, J=6.9 Hz, 3H), 0.81 (d, J=6.8 Hz, 3H).

SEQ ID NO: 43: Glu-Pro-Val-Pro-Gln-Ala (Acetate Salt)

High resolution mass spectrometry (Orbitrap-HRMS), molecular formula: $C_{28}H_{45}N_7O_{10}$; m/z: 640.32892 ([M+H]$^{+}$).

$^{1}$H NMR (600 MHz, $D_2O$) δ 4.34 (dd, J=8.3, 6.5 Hz, 1H), 4.25-4.15 (m, 3H), 4.08 (dd, J=8.8, 5.9 Hz, 1H), 4.04-4.00 (m, 1H), 3.73-3.65 (m, 1H), 3.57-3.41 (m, 3H), 2.35 (t, J=7.3 Hz, 2H), 2.24-2.20 (m, 2H), 2.16-2.07 (m, 2H), 2.04-1.75 (m, AcOH, 11H), 1.73-1.63 (m, 2H), 1.17 (d, J=7.2 Hz, 3H), 0.80 (dd, J=12.9, 6.8 Hz, 6H).

SEQ ID NO: 44: Pro-Val-Pro-Gln-Ala-Lys (Acetate Salt)

High resolution mass spectrometry (Orbitrap-HRMS), molecular formula: $C_{29}H_{50}N_8O_8$; m/z: 320.19421 ([M+2H]$^{2+}$).

$^{1}$H NMR (600 MHz, $D_2O$) δ 4.29-4.19 (m, 3H), 4.13-4.06 (m, 2H), 3.95 (dd, J=8.2, 5.1 Hz, 1H), 3.73-3.68 (m, 1H), 3.52-3.47 (m, 1H), 3.24-3.16 (m, 2H), 2.79 (t, J=7.5 Hz, 2H), 2.25-2.19 (m, 3H), 2.14-2.08 (m, 1H), 1.97-1.57 (m, AcOH, 17H), 1.53-1.45 (m, 3H), 1.21-1.17 (m, 5H), 0.82 (d, J=6.8 Hz, 3H), 0.75 (d, J=6.7 Hz, 3H).

SEQ ID NO: 45: Glu-Pro-Val-Pro-Gln-Ala-Arg (Acetate Salt)

High resolution mass spectrometry (Orbitrap-HRMS), molecular formula: $C_{34}H_{57}N_{11}O_{11}$; m/z: 398.71835 ([M+2H]$^{2+}$), 796.42944 ([M+H]$^{+}$).

$^{1}$H NMR (600 MHz, $D_2O$) δ 4.38 (dd, J=8.3, 6.4 Hz, 1H), 4.27-4.19 (m, 3H), 4.19-4.10 (m, 2H), 4.03 (dd, J=8.3, 4.9 Hz, 1H), 3.78-3.70 (m, 1H), 3.60-3.46 (m, 3H), 3.07-3.02 (m, 2H), 2.30 (t, J=7.2 Hz, 2H), 2.25 (t, J=7.6 Hz, 2H), 2.19-2.11 (m, 2H), 2.06-1.78 (m, AcOH, 12H), 1.76-1.67 (m, 3H), 1.60-1.53 (m, 1H), 1.48-1.42 (m, 2H), 1.24 (d, J=7.1 Hz, 3H), 0.85 (dd, J=12.8, 6.7 Hz, 6H).

SEQ ID NO: 46: Ala-Pro-Val-Pro-Gln-Ala-Lys (Acetate Salt)

High resolution mass spectrometry (Orbitrap-HRMS), molecular formula: $C_{32}H_{55}N_9O_9$; m/z: 355.71259 ([M+2H]$^{2+}$), 710.41809 ([M+H]$^{+}$).

$^{1}$H NMR (600 MHz, DMSO-$d_6$) δ 8.23 (d, J=7.7 Hz, 1H), 8.08 (d, J=8.1 Hz, 1H), 7.87 (d, J=8.4 Hz, 1H), 7.68 (s, 1H), 7.38 (d, J=6.4 Hz, 1H), 6.75 (s, 1H), 4.40-4.37 (m, 1H), 4.33-4.25 (m, 3H), 4.15 (t, J=7.2 Hz, 3H), 3.78 (d, J=6.4 Hz, 1H), 3.66 (dd, J=32.4, 8.0 Hz, 2H), 3.58-3.51 (m, 2H), 3.43 (d, J=7.0 Hz, 1H), 3.36-3.27 (m, 1H), 2.67 (t, J=7.7 Hz, 3H), 2.19-2.07 (m, 4H), 2.01-1.69 (m, AcOH, 24H), 1.63-1.60 (m, 1H), 1.55-1.41 (m, 5H), 1.26 (d, 1H), 1.18 (d, J=7.2 Hz, 6H), 1.11 (d, J=6.7 Hz, 3H), 1.04 (d, J=6.6 Hz, 1H), 0.87 (d, J=6.7 Hz, 3H), 0.83 (d, J=6.9 Hz, 3H).

SEQ ID NO: 47: Glu-Pro-Val-Pro-Ala-Ala-Lys (Acetate Salt)

High resolution mass spectrometry (Orbitrap-HRMS), molecular formula: $C_{32}H_{54}N_8O_{10}$; m/z: 356.20514 ([M+2H]$^{2+}$), 711.40198 ([M+H]$^{+}$).

$^{1}$H NMR (600 MHz, $D_2O$) δ 4.45 (dd, J=8.4, 6.4 Hz, 1H), 4.33-4.27 (m, 3H), 4.21 (dd, J=15.1, 7.2 Hz, 2H), 4.07 (dd, J=8.1, 5.1 Hz, 1H), 3.86-3.75 (m, 1H), 3.67-3.54 (m, 3H), 2.91 (t, J=7.5 Hz, 2H), 2.37 (t, J=6.9 Hz, 2H), 2.26-2.18 (m, 2H), 2.14-1.69 (m, AcOH, 13H), 1.65-1.58 (m, 3H), 1.35-1.29 (m, 9H), 0.92 (dd, J=13.6, 6.8 Hz, 6H).

SEQ ID NO: 48: Glu-Pro-Val-Pro-Gln-Ala-Ala (Acetate Salt)

High resolution mass spectrometry (Orbitrap-HRMS), molecular formula: $C_{31}H_{50}N_8O_{11}$; m/z: 356.18692 ([M+2H]$^{2+}$), 711.36597 ([M+H]$^{+}$).

$^{1}$H NMR (600 MHz, $D_2O$) δ 4.34 (dd, J=8.3, 6.5 Hz, 1H), 4.24-4.16 (m, 3H), 4.12-4.06 (m, 2H), 4.03-3.99 (m, 1H), 3.73-3.65 (m, 1H), 3.56-3.41 (m, 3H), 2.35 (t, J=7.3 Hz, 2H), 2.22-2.18 (m, 2H), 2.15-2.07 (m, 2H), 2.04-1.73 (m, AcOH, 11H), 1.71-1.63 (m, 2H), 1.18 (dd, J=11.2, 7.2 Hz, 6H), 0.80 (dd, J=13.0, 6.8 Hz, 6H).

SEQ ID NO: 49: Asp-Pro-Val-Pro-Gln-Ala-Lys (Acetate Salt)

High resolution mass spectrometry (Orbitrap-HRMS), molecular formula: $C_{33}H_{55}N_9O_{11}$; m/z: 377.70767 ([M+2H]$^{2+}$), 754.40814 ([M+H]$^{+}$).

$^{1}$H NMR (600 MHz, $D_2O$) δ 4.36-4.29 (m, 2H), 4.23-4.14 (m, 2H), 4.13-4.06 (m, 2H), 3.97 (dd, J=8.3, 5.0 Hz, 1H), 3.74-3.65 (m, 1H), 3.56-3.46 (m, 2H), 3.44-3.39 (m, 1H), 2.79 (t, J=7.5 Hz, 2H), 2.65 (dd, J=17.5, 3.3 Hz, 1H), 2.38 (dd, J=17.5, 10.7 Hz, 1H), 2.21 (t, J=7.6 Hz, 2H), 2.15-2.06 (m, 2H), 1.93-1.75 (m, AcOH, 9H), 1.72-1.61 (m, 3H), 1.54-1.45 (m, 3H), 1.21 (dd, J=13.1, 7.5 Hz, 5H), 0.80 (dd, J=11.0, 6.7 Hz, 6H).

SEQ ID NO: 50: Asn-Pro-Val-Pro-Gln-Ala-Lys (Acetate Salt)

High resolution mass spectrometry (Orbitrap-HRMS), molecular formula: $C_{33}H_{56}N_{10}O_{10}$; m/z: 377.21542 ([M+2H]$^{2+}$), 753.42365 ([M+H]$^{+}$).

$^{1}$H NMR (600 MHz, $D_2O$) δ 4.55 (dd, J=9.3, 4.0 Hz, 1H), 4.47 (dd, J=8.4, 6.1 Hz, 1H), 4.34-4.29 (m, 2H), 4.26-4.19 (m, 2H), 4.07 (dd, J=8.1, 5.1 Hz, 1H), 3.83-3.77 (m, 1H), 3.69-3.53 (m, 3H), 2.94-2.90 (m, 3H), 2.72 (dd, J=17.0, 9.3 Hz, 1H), 2.33 (t, J=7.6 Hz, 2H), 2.27-2.19 (m, 2H), 2.05-1.71 (m, AcOH, 15H), 1.65-1.57 (m, 3H), 1.34-1.30 (m, 5H), 0.91 (dd, J=13.4, 6.7 Hz, 6H).

SEQ ID NO: 51: Glu-Pro-Val-Pro-Gln-Ala-Lys-Pro-Arg-Lys-Val-Ala (Acetate Salt)

High resolution mass spectrometry (Orbitrap-HRMS), molecular formula: $C_{59}H_{102}N_{18}O_{16}$; m/z: 440.59735 ([M+3H]$^{3+}$), 660.39252 ([M+2H]$^{2+}$).

$^{1}$H NMR (600 MHz, $D_2O$) δ 4.38 (dd, J=9.3, 4.8 Hz, 1H), 4.33 (dd, J=8.3, 6.5 Hz, 1H), 4.22-4.12 (m, 5H), 4.10-4.04 (m, 3H), 3.93-3.88 (m, 2H), 3.75-3.67 (m, 1H), 3.66-3.58 (m, 1H), 3.56-3.41 (m, 4H), 3.00 (t, J=6.9 Hz, 2H), 2.82-2.76 (m, 4H), 2.24-2.19 (m, 4H), 2.14-2.06 (m, 3H), 1.97-1.41 (m, AcOH, 37H), 1.33-1.12 (m, 10H), 0.80 (dd, J=9.7, 6.7 Hz, 6H), 0.74 (dd, J=11.0, 6.8 Hz, 6H).

SEQ ID NO: 52: Glu-Pro-Ala-Pro-Gln-Ala-Lys (Acetate Salt)

High resolution mass spectrometry (Orbitrap-HRMS), molecular formula: $C_{32}H_{53}N_9O_{11}$; m/z: 370.6998 ([M+2H]$^{2+}$), 740.39221 ([M+H]$^{+}$).

$^{1}$H NMR (600 MHz, $D_2O$) δ 4.43 (q, J=7.1 Hz, 1H), 4.33 (dd, J=8.4, 6.5 Hz, 1H), 4.26 (dd, J=8.4, 5.8 Hz, 1H), 4.22 (dd, J=7.6, 4.6 Hz, 1H), 4.18-4.11 (m, 2H), 4.01 (dd, J=8.3, 5.0 Hz, 1H), 3.67 (dt, J=10.0, 6.7 Hz, 1H), 3.61-3.54 (m, 1H), 3.53-3.44 (m, 2H), 2.84 (t, J=7.5 Hz, 2H), 2.30 (t, J=7.2 Hz, 2H), 2.25 (t, J=7.6 Hz, 2H), 2.21-2.12 (m, 2H), 2.08-1.77 (m, AcOH, 11H), 1.77-1.63 (m, 3H), 1.60-1.49 (m, 3H), 1.24 (dd, J=10.4, 7.1 Hz, 6H).

SEQ ID NO: 53: Glu-Ala-Val-Pro-Gln-Ala-Lys (Acetate Salt)

High resolution mass spectrometry (Orbitrap-HRMS), molecular formula: $C_{32}H_{55}N_9O_{11}$; m/z: 371.7081 ([M+2H]$^{2+}$), 742.4089 ([M+H]$^{+}$).

$^{1}$H NMR (600 MHz, $D_2O$) δ 4.23-4.18 (m, 3H), 4.13-4.06 (m, 2H), 3.95 (dd, J=8.3, 5.0 Hz, 1H), 3.85-3.82 (m, 1H), 3.73-3.66 (m, 1H), 3.53-3.47 (m, 1H), 2.79 (t, J=7.5 Hz, 2H), 2.22-2.17 (m, 4H), 2.13-2.07 (m, 1H), 1.99-1.70 (m, AcOH, 9H), 1.69-1.59 (m, 2H), 1.53-1.45 (m, 3H), 1.26-1.12 (m, 9H), 0.79 (d, J=6.7 Hz, 3H), 0.76 (d, J=6.7 Hz, 3H).

SEQ ID NO: 54: Glu-Pro-Val-Ala-Gln-Ala-Lys (Acetate Salt)

High resolution mass spectrometry (Orbitrap-HRMS), molecular formula: $C_{32}H_{55}N_9O_{11}$; m/z: 371.70767 ([M+2H]$^{2+}$), 742.40802 ([M+H]$^{+}$).

$^{1}$H NMR (600 MHz, DMSO-$d_6$+$D_2O$) δ 4.34 (dd, J=8.3, 6.0 Hz, 1H), 4.15-4.05 (m, 4H), 3.97-3.87 (m, 2H), 3.51 (d, J=9.8 Hz, 1H), 3.46-3.38 (m, 1H), 2.74 (t, J=7.5 Hz, 2H), 2.23 (t, J=7.1 Hz, 2H), 2.17-2.06 (m, 3H), 1.95-1.67 (m, AcOH, 10H), 1.65-1.59 (m, 1H), 1.53-1.42 (m, 3H), 1.22-1.13 (m, 8H), 0.78 (d, J=6.8 Hz, 6H).

SEQ ID NO: 55: Glu-Pro-Val-Pro-Glu-Ala-Lys (Acetate Salt)

High resolution mass spectrometry (Orbitrap-HRMS), molecular formula: $C_{34}H_{56}N_8O_{12}$; m/z: 385.2083 ([M+2H]$^{2+}$), 769.4092 ([M+H]$^{+}$).

$^{1}$H NMR (600 MHz, $D_2O$) δ 4.33 (dd, J=8.3, 6.5 Hz, 1H), 4.21-4.16 (m, 3H), 4.11 (t, J=7.1 Hz, 1H), 4.07 (dd, J=8.8, 5.7 Hz, 1H), 3.98 (dd, J=8.5, 4.8 Hz, 1H), 3.71-3.66 (m, 1H), 3.55-3.41 (m, 3H), 2.78 (t, J=7.5 Hz, 2H), 2.36-2.14 (m, 5H), 2.13-2.05 (m, 2H), 1.99-1.74 (m, AcOH, 11H), 1.70-1.61 (m, 3H), 1.53-1.45 (m, 3H), 1.20 (dd, J=15.4, 7.5 Hz, 5H), 0.80 (dd, J=12.5, 6.7 Hz, 6H).

SEQ ID NO: 56: Glu-Pro-Val-Pro-Gln-Ala-Lys-Pro-Arg-Lys-Val (Acetate Salt)

High resolution mass spectrometry (Orbitrap-HRMS), molecular formula: $C_{56}H_{97}N_{17}O_{15}$; m/z: 416.91827 ($[M+3H]^{3+}$), 624.87354 ($[M+2H]^{2+}$).

$^{1}$H NMR (600 MHz, $D_2O$) δ 4.43 (dd, J=9.3, 4.9 Hz, 1H), 4.38 (dd, J=8.4, 6.4 Hz, 1H), 4.27-4.19 (m, 5H), 4.16-4.10 (m, 3H), 3.88 (d, J=6.2 Hz, 1H), 3.74 (dt, J=10.1, 6.9 Hz, 1H), 3.71-3.63 (m, 1H), 3.60-3.46 (m, 4H), 3.07-3.02 (m, 2H), 2.87-2.82 (m, 4H), 2.29-2.24 (m, 4H), 2.19-2.11 (m, 3H), 2.04-1.43 (m, AcOH, 37H), 1.37-1.20 (m, 7H), 0.85 (dd, J=10.1, 6.8 Hz, 6H), 0.74 (dd, J=11.8, 6.9 Hz, 6H).

SEQ ID NO: 57: Glu-Pro-Val-Pro-Gln-Ala-Lys-Pro-Arg (Acetate Salt)

High resolution mass spectrometry (Orbitrap-HRMS), molecular formula: $C_{45}H_{76}N_{14}O_{13}$; m/z: 511.29254 ($[M+2H]^{2+}$).

$^{1}$H NMR (600 MHz, $D_2O$) δ 4.39 (dd, J=8.6, 5.5 Hz, 1H), 4.32 (dd, J=8.3, 6.5 Hz, 1H), 4.22-4.13 (m, 4H), 4.10-4.03 (m, 2H), 3.93 (dd, J=7.9, 5.2 Hz, 1H), 3.72-3.60 (m, 2H), 3.54-3.40 (m, 4H), 3.00 (t, J=6.9 Hz, 2H), 2.80 (t, J=7.5 Hz, 2H), 2.24-2.18 (m, 4H), 2.14-2.06 (m, 3H), 1.98-1.70 (m, AcOH, 19H), 1.69-1.60 (m, 4H), 1.55-1.47 (m, 4H), 1.45-1.39 (m, 2H), 1.34-1.24 (m, 2H), 1.16 (d, J=7.1 Hz, 3H), 0.80 (dd, J=10.4, 6.7 Hz, 6H).

SEQ ID NO: 58: Glu-Pro-Val-Pro-Gln-Ala-Lys-Pro (Acetate Salt)

High resolution mass spectrometry (Orbitrap-HRMS), molecular formula: $C_{39}H_{64}N_{10}O_{12}$; m/z: 433.24188 ($[M+2H]^{2+}$), 865.47662 ($[M+H]^{+}$).

$^{1}$H NMR (600 MHz, $D_2O$) δ 4.41 (dd, J=8.5, 5.5 Hz, 1H), 4.33 (dd, J=8.3, 6.5 Hz, 1H), 4.22-4.14 (m, 3H), 4.11-4.02 (m, 3H), 3.75-3.67 (m, 1H), 3.59-3.41 (m, 5H), 2.81 (t, J=7.4 Hz, 2H), 2.25-2.19 (m, 4H), 2.15-1.61 (m, AcOH, 26H), 1.57-1.48 (m, 3H), 1.37-1.23 (m, 2H), 1.16 (d, J=7.0 Hz, 3H), 0.80 (dd, J=11.5, 6.7 Hz, 6H).

SEQ ID NO: 59: Pro-Val-Pro-Gln-Ala-Lys-Pro-Arg (Acetate Salt)

High resolution mass spectrometry (Orbitrap-HRMS), molecular formula: $C_{40}H_{69}N_{13}O_{10}$; m/z: 298.18314 ($[M+3H]^{3+}$), 446.77118 ($[M+2H]^{2+}$), 892.53497 ($[M+H]^{+}$).

$^{1}$H NMR (600 MHz, $D_2O$) δ 4.40 (dd, J=8.6, 5.5 Hz, 1H), 4.30-4.19 (m, 4H), 4.11-4.05 (m, 2H), 3.93 (dd, J=7.9, 5.2 Hz, 1H), 3.73-3.63 (m, 2H), 3.52-3.45 (m, 2H), 3.26-3.17 (m, 2H), 3.01 (t, J=6.9 Hz, 2H), 2.81 (t, J=7.5 Hz, 2H), 2.26-2.19 (m, 3H), 2.14-2.09 (m, 2H), 1.94-1.62 (m, AcOH, 24H), 1.57-1.40 (m, 7H), 1.34-1.26 (m, 2H), 1.16 (d, J=7.3 Hz, 3H), 0.82 (d, J=6.8 Hz, 3H), 0.76 (d, J=6.7 Hz, 3H).

SEQ ID NO: 60: Pro-Val-Pro-Gln-Ala-Lys-Pro (Acetate Salt)

High resolution mass spectrometry (Orbitrap-HRMS), molecular formula: $C_{34}H_{57}N_{9}O_{9}$; m/z: 368.7207 ($[M+2H]^{2+}$), 736.4343 ($[M+H]^{+}$).

$^{1}$H NMR (600 MHz, $D_2O$) δ 4.46 (dd, J=8.4, 5.6 Hz, 1H), 4.34 (d, J=7.4 Hz, 1H), 4.29 (dd, J=8.5, 6.2 Hz, 1H), 4.27-4.24 (m, 1H), 4.16-4.07 (m, 3H), 3.78-3.70 (m, 1H), 3.66-3.60 (m, 1H), 3.58-3.45 (m, 2H), 3.30-3.22 (m, 2H), 2.86 (t, J=7.5 Hz, 2H), 2.32-2.24 (m, 3H), 2.19-2.13 (m, 1H), 2.12-2.03 (m, 1H), 2.02-1.69 (m, AcOH, 19H), 1.61-1.52 (m, 3H), 1.42-1.27 (m, 2H), 1.23-1.20 (m, 3H), 0.87 (d, J=6.8 Hz, 3H), 0.81 (d, J=6.7 Hz, 3H).

SEQ ID NO: 61: D-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4978 ($[M+4H]^{4+}$), 549.6611 ($[M+3H]^{3+}$), 823.9882 ($[M+2H]^{2+}$).

$^{1}$H NMR (600 MHz, $D_2O$) δ 4.46-4.35 (m, 2H), 4.27 (dd, J=8.3, 6.1 Hz, 1H), 4.22-4.04 (m, 9H), 3.96 (dd, J=8.4, 4.8 Hz, 1H), 3.90 (d, J=7.7 Hz, 1H), 3.84 (t, J=6.6 Hz, 1H), 3.74-3.59 (m, 3H), 3.56-3.38 (m, 3H), 3.01 (t, J=6.9 Hz, 2H), 2.83-2.76 (m, 6H), 2.23-2.06 (m, 9H), 1.96-1.39 (m, AcOH, 48H), 1.18 (dd, J=22.0, 7.2 Hz, 15H), 0.83-0.67 (m, 12H).

SEQ ID NO: 62: Lys-D-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4976 ($[M+4H]^{4+}$), 549.6608 ($[M+3H]^{3+}$).

$^{1}$H NMR (600 MHz, $D_2O$) δ 4.50 (dd, J=9.8, 4.4 Hz, 1H), 4.37 (dd, J=9.4, 4.9 Hz, 1H), 4.25-4.03 (m, 10H), 3.95 (dd, J=8.5, 4.8 Hz, 1H), 3.89 (d, J=7.7 Hz, 1H), 3.83 (t, J=6.6 Hz, 1H), 3.74-3.68 (m, 1H), 3.64-3.55 (m, 2H), 3.52-3.38 (m, 2H), 3.00 (t, J=6.9 Hz, 2H), 2.83-2.75 (m, 6H), 2.20 (t, J=7.6 Hz, 2H), 2.12-2.06 (m, 6H), 1.92-1.41 (m, AcOH, 47H), 1.32-1.13 (m, 15H), 0.78 (dd, J=9.7, 6.7 Hz, 6H), 0.73 (dd, J=6.8, 4.1 Hz, 6H).

SEQ ID NO: 63: Lys-Glu-D-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4976 ($[M+4H]^{4+}$), 549.6609 ($[M+3H]^{3+}$), 823.9878 ($[M+2H]^{2+}$).

$^{1}$H NMR (600 MHz, $D_2O$) δ 4.45 (dd, J=9.4, 4.4 Hz, 1H), 4.37 (dd, J=9.4, 4.9 Hz, 1H), 4.29-4.25 (m, 1H), 4.21-4.04 (m, 8H), 3.96-3.94 (m, 1H), 3.89 (d, J=7.7 Hz, 1H), 3.79 (d, J=6.9 Hz, 1H), 3.68-3.59 (m, 2H), 3.54-3.35 (m, 3H), 3.00 (t, J=6.9 Hz, 2H), 2.82-2.74 (m, 6H), 2.23-2.19 (m, 2H), 2.15-2.02 (m, 6H), 1.95-1.41 (m, AcOH, 48H), 1.17 (dd, J=21.6, 7.2 Hz, 15H), 0.83-0.64 (m, 12H).

SEQ ID NO: 64: Lys-Glu-Pro-D-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4978 ($[M+4H]^{4+}$), 549.6609 ($[M+3H]^{3+}$), 823.9878 ($[M+2H]^{2+}$).

$^{1}$H NMR (600 MHz, $D_2O$) δ 4.46 (dd, J=10.2, 3.9 Hz, 1H), 4.41-4.31 (m, 2H), 4.27-4.18 (m, 3H), 4.15-4.02 (m, 7H), 3.95-3.92 (m, 1H), 3.89 (d, J=7.7 Hz, 1H), 3.83 (t, J=6.6 Hz, 1H), 3.67-3.50 (m, 5H), 3.47-3.25 (m, 2H), 3.00 (t, J=6.9 Hz, 2H), 2.81-2.76 (m, 6H), 2.23-2.06 (m, 10H), 1.94-1.41 (m, AcOH, 50H), 1.17 (dd, J=19.9, 7.1 Hz, 17H), 0.76-0.68 (m, 12H).

SEQ ID NO: 65: Lys-Glu-Pro-Val-D-Pro-Gln-Ala-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4979 ($[M+4H]^{4+}$), 549.6612 ($[M+3H]^{3+}$), 823.9883 ($[M+2H]^{2+}$).

$^{1}$H NMR (600 MHz, $D_2O$) δ 4.42 (dd, J=9.9, 4.2 Hz, 1H), 4.34 (dd, J=9.2, 5.2 Hz, 1H), 4.31-4.23 (m, 2H), 4.22-4.18 (m, 2H), 4.15-4.05 (m, 6H), 3.94 (dd, J=8.4, 4.8 Hz, 1H), 3.89 (d, J=7.7 Hz, 1H), 3.82 (t, J=6.7 Hz, 1H), 3.65 (d, J=6.8 Hz, 3H), 3.57-3.36 (m, 3H), 3.00 (t, J=6.9 Hz, 2H), 2.82-2.75 (m, 6H), 2.18-2.03 (m, 9H), 1.95-1.40 (m, AcOH, 46H), 1.37-1.08 (m, 16H), 0.80-0.68 (m, 12H).

SEQ ID NO: 66: Lys-Glu-Pro-Val-Pro-D-Gln-Ala-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4978 ($[M+4H]^{4+}$), 549.6611 ($[M+3H]^{3+}$), 823.9881 ($[M+2H]^{2+}$).

$^{1}$H NMR (600 MHz, $D_2O$) δ 4.44-4.35 (m, 2H), 4.26-4.04 (m, 10H), 3.94 (dd, J=8.5, 4.8 Hz, 1H), 3.89 (d, J=7.7 Hz, 1H), 3.82 (t, J=6.8 Hz, 1H), 3.76-3.68 (m, 1H), 3.64 (d, J=8.7 Hz, 2H), 3.55-3.37 (m, 3H), 3.00 (t, J=6.9 Hz, 2H), 2.83-2.75 (m, 6H), 2.19-2.05 (m, 9H), 2.02-1.38 (m, AcOH, 47H), 1.34-1.15 (m, 15H), 0.78 (dd, J=11.2, 6.7 Hz, 6H), 0.73 (dd, J=6.7, 3.9 Hz, 6H).

SEQ ID NO: 67: Lys-Glu-Pro-Val-Pro-Gln-D-Ala-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4961 ([M+4H]$^{4+}$), 549.6615 ([M+3H]$^{3+}$), 823.9886 ([M+2H]$^{2+}$).

$^{1}$H NMR (600 MHz, $D_2O$) δ 4.47-4.38 (m, 2H), 4.26 (dd, J=8.4, 5.8 Hz, 1H), 4.22-4.04 (m, 9H), 3.95 (dd, J=8.5, 4.8 Hz, 1H), 3.89 (d, J=7.7 Hz, 1H), 3.82 (t, J=6.8 Hz, 1H), 3.74-3.56 (m, 3H), 3.54-3.35 (m, 3H), 3.00 (t, J=6.9 Hz, 2H), 2.86-2.74 (m, 6H), 2.23-2.05 (m, 9H), 1.94-1.38 (m, AcOH, 46H), 1.29-1.14 (m, 15H), 0.78 (dd, J=10.5, 6.7 Hz, 6H), 0.73 (dd, J=6.8, 3.9 Hz, 6H).

SEQ ID NO: 68: Lys-Glu-Pro-Val-Pro-Gln-Ala-D-Lys-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4977 ([M+4H]$^{4+}$), 549.6615 ([M+3H]$^{3+}$), 823.9879 ([M+2H]$^{2+}$).

$^{1}$H NMR (600 MHz, $D_2O$) δ 4.47-4.40 (m, 2H), 4.26 (dd, J=8.4, 5.9 Hz, 1H), 4.23-4.15 (m, 3H), 4.14-4.01 (m, 6H), 3.95 (dd, J=8.5, 4.8 Hz, 1H), 3.89 (d, J=7.7 Hz, 1H), 3.82 (t, J=6.8 Hz, 1H), 3.71-3.44 (m, 5H), 3.01 (t, J=6.9 Hz, 2H), 2.82-2.73 (m, 6H), 2.23-2.05 (m, 9H), 1.93-1.40 (m, AcOH, 46H), 1.30-1.14 (m, 15H), 0.79 (dd, J=12.5, 6.7 Hz, 6H), 0.73 (dd, J=6.8, 4.6 Hz, 6H).

SEQ ID NO: 69: Lys-Glu-Pro-Val-Pro-Gln-Ala-Lys-D-Pro-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4976 ([M+4H]$^{4+}$), 549.6608 ([M+3H]$^{3+}$).

$^{1}$H NMR (600 MHz, $D_2O$) δ 4.42 (dt, J=8.2, 4.3 Hz, 2H), 4.26 (dd, J=8.4, 5.9 Hz, 1H), 4.23-4.14 (m, 3H), 4.14-4.05 (m, 6H), 3.94 (dd, J=8.5, 4.8 Hz, 1H), 3.89 (d, J=7.7 Hz, 1H), 3.81 (q, J=7.7, 7.2 Hz, 1H), 3.74-3.58 (m, 3H), 3.55-3.38 (m, 3H), 2.98 (t, J=7.0 Hz, 2H), 2.82-2.75 (m, 6H), 2.23-2.05 (m, 9H), 1.93-1.13 (m, AcOH, 62H), 0.79 (dd, J=13.2, 6.7 Hz, 6H), 0.73 (dd, J=6.8, 4.7 Hz, 6H).

SEQ ID NO: 70: Lys-Glu-Pro-Val-Pro-Gln-Ala-Lys-Pro-D-Arg-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4978 ([M+4H]$^{4+}$), 549.6611 ([M+3H]$^{3+}$), 823.9883 ([M+2H]$^{2+}$).

$^{1}$H NMR (600 MHz, $D_2O$) δ 4.45-4.36 (m, 2H), 4.27-4.14 (m, 6H), 4.12-4.05 (m, 4H), 3.95 (dd, J=8.4, 4.8 Hz, 1H), 3.90 (d, J=7.7 Hz, 1H), 3.82 (t, J=6.8 Hz, 1H), 3.66 (dd, J=35.9, 8.3 Hz, 3H), 3.55-3.39 (m, 3H), 2.99 (t, J=7.0 Hz, 2H), 2.82-2.75 (m, 6H), 2.23-2.07 (m, 9H), 1.93-1.15 (m, AcOH, 63H), 0.79 (dd, J=13.9, 6.7 Hz, 6H), 0.74 (dd, J=6.8, 2.0 Hz, 6H).

SEQ ID NO: 71: Lys-Glu-Pro-Val-Pro-Gln-Ala-Lys-Pro-Arg-D-Lys-Val-Ala-Ala-Gln (Acetate Salt)

High resolution mass spectrometry (Orbitrap-HRMS), molecular formula: $C_{73}H_{127}N_{23}O_{20}$; m/z: 412.4976 ([M+4H]$^{4+}$), 549.6609 ([M+3H]$^{3+}$), 823.9878 ([M+2H]$^{2+}$).

$^{1}$H NMR (600 MHz, $D_2O$) δ 4.45-4.36 (m, 2H), 4.26 (dd, J=8.4, 5.8 Hz, 1H), 4.22-4.16 (m, 3H), 4.12-4.05 (m, 6H), 3.96-3.91 (m, 2H), 3.82 (t, J=6.8 Hz, 1H), 3.73-3.58 (m, 3H), 3.54-3.36 (m, 3H), 3.00 (t, J=7.0 Hz, 2H), 2.82-2.75 (m, 6H), 2.22-2.06 (m, 9H), 1.93-1.41 (m, AcOH, 45H), 1.32-1.14 (m, 15H), 0.79 (dd, J=13.8, 6.7 Hz, 6H), 0.74 (d, J=6.8 Hz, 3H), 0.70 (d, J=6.8 Hz, 3H).

SEQ ID NO: 72: Lys-Glu-Pro-Val-Pro-Gln-Ala-Lys-Pro-Arg-Lys-D-Val-Ala-Ala-Gln (Acetate Salt)

High resolution mass spectrometry (Orbitrap-HRMS), molecular formula: $C_{73}H_{127}N_{23}O_{20}$; m/z: 412.4976 ([M+4H]$^{4+}$), 549.6609 ([M+3H]$^{3+}$), 823.9876 ([M+2H]$^{2+}$).

$^{1}$H NMR (600 MHz, $D_2O$ δ 4.45-4.35 (m, 2H), 4.26 (dd, J=8.4, 5.9 Hz, 1H), 4.21-4.05 (m, 9H), 3.94-3.88 (m, 2H), 3.82 (t, J=6.8 Hz, 1H), 3.73-3.57 (m, 3H), 3.55-3.37 (m, 3H), 2.99 (t, J=6.8 Hz, 2H), 2.82-2.75 (m, 6H), 2.23-2.06 (m, 9H), 1.96-1.36 (m, AcOH, 50H), 1.32-1.14 (m, 15H), 0.78 (dd, J=13.9, 6.7 Hz, 6H), 0.73 (d, J=6.7 Hz, 6H).

SEQ ID NO: 73: Lys-Glu-Pro-Val-Pro-Gln-Ala-Lys-Pro-Arg-Lys-Val-D-Ala-Ala-Gln (Acetate Salt)

High resolution mass spectrometry (Orbitrap-HRMS), molecular formula: $C_{73}H_{127}N_{23}O_{20}$; m/z: 412.4977 ([M+4H]$^{4+}$), 549.6609 ([M+3H]$^{3+}$), 823.9879 ([M+2H]$^{2+}$).

$^{1}$H NMR (600 MHz, $D_2O$) δ 4.48 (dd, J=9.7, 4.3 Hz, 1H), 4.43 (dd, J=9.3, 4.9 Hz, 1H), 4.32 (dd, J=8.4, 5.8 Hz, 1H), 4.27-4.23 (m, 3H), 4.21-4.17 (m, 3H), 4.15-4.10 (m, 3H), 3.97 (dd, J=9.2, 4.6 Hz, 1H), 3.89-3.85 (m, 2H), 3.76-3.66 (m, 3H), 3.59-3.45 (m, 3H), 3.05 (t, J=6.9 Hz, 2H), 2.87-2.81 (m, 6H), 2.26 (t, J=7.7 Hz, 2H), 2.22-2.12 (m, 7H), 2.00-1.48 (m, AcOH, 47H), 1.37-1.20 (m, 16H), 0.86-0.77 (m, 12H).

SEQ ID NO: 74: Lys-Glu-Pro-Val-Pro-Gln-Ala-Lys-Pro-Arg-Lys-Val-Ala-D-Ala-Gln (Acetate Salt)

High resolution mass spectrometry (Orbitrap-HRMS), molecular formula: $C_{73}H_{127}N_{23}O_{20}$; m/z: 412.4977 ([M+4H]$^{4+}$), 549.6610 ([M+3H]$^{3+}$), 823.9879 ([M+2H]$^{2+}$).

$^{1}$H NMR (600 MHz, $D_2O$) δ 4.48 (dd, J=9.6, 4.3 Hz, 1H), 4.44 (dd, J=9.3, 4.9 Hz, 1H), 4.32 (dd, J=8.4, 5.8 Hz, 1H), 4.28-4.17 (m, 5H), 4.17-4.09 (m, 4H), 4.05 (dd, J=9.1, 4.7 Hz, 1H), 3.95 (d, J=7.7 Hz, 1H), 3.88 (t, J=6.8 Hz, 1H), 3.78-3.63 (m, 3H), 3.60-3.37 (m, 3H), 3.06 (t, J=6.9 Hz, 2H), 2.89-2.81 (m, 6H), 2.29-2.09 (m, 9H), 2.02-1.46 (m, AcOH, 45H), 1.39-1.19 (m, 15H), 0.84 (dd, J=14.0, 6.7 Hz, 6H), 0.78 (dd, J=14.3, 6.8 Hz, 6H).

SEQ ID NO: 75: Lys-Glu-Pro-Val-Pro-Gln-Ala-Lys-Pro-Arg-Lys-Val-Ala-Ala-D-Gln (Acetate Salt)

High resolution mass spectrometry (Orbitrap-HRMS), molecular formula: $C_{73}H_{127}N_{23}O_{20}$; m/z: 412.4978 ([M+4H]$^{4+}$), 549.6611 ([M+3H]$^{3+}$), 823.9881 ([M+2H]$^{2+}$).

$^{1}$H NMR (600 MHz, $D_2O$) δ 4.49-4.42 (m, 2H), 4.32 (dd, J=8.4, 5.8 Hz, 1H), 4.27-4.10 (m, 9H), 4.04 (dd, J=8.4, 4.6 Hz, 1H), 3.96 (d, J=7.4 Hz, 1H), 3.90-3.84 (m, 1H), 3.73 (d, J=7.7 Hz, 1H), 3.71-3.64 (m, 2H), 3.60-3.32 (m, 3H), 3.06 (t, J=6.9 Hz, 2H), 2.89-2.79 (m, 6H), 2.28-2.06 (m, 9H), 1.99-1.47 (m, AcOH, 44H), 1.39-1.18 (m, 15H), 0.84 (dd, J=13.9, 6.7 Hz, 6H), 0.78 (dd, J=6.8, 3.3 Hz, 6H).

SEQ ID NO: 76: Glu-Gly-Val-Pro-Gln-Ala-Lys (Acetate Salt)

High resolution mass spectrometry (Orbitrap-HRMS), molecular formula: $C_{31}H_{53}N_9O_{11}$; m/z: 364.7022 ([M+2H]$^{2+}$), 728.3929 ([M+H]$^{+}$).

$^{1}$H NMR (600 MHz, $D_2O$) δ 4.30 (d, J=7.8 Hz, 1H), 4.26 (dd, J=8.2, 6.7 Hz, 1H), 4.19-4.11 (m, 2H), 4.02 (dd, J=8.3, 5.0 Hz, 1H), 3.95 (t, J=6.5 Hz, 1H), 3.91-3.82 (m, 2H), 3.78-3.72 (m, 1H), 3.58-3.51 (m, 1H), 2.84 (t, J=7.5 Hz, 2H), 2.29-2.24 (m, 4H), 2.20-2.11 (m, 1H), 2.01-1.82 (m, AcOH, 10H), 1.77-1.65 (m, 2H), 1.60-1.50 (m, 3H), 1.25 (dd, J=7.5, 4.7 Hz, 5H), 0.84 (d, J=6.8 Hz, 3H), 0.80 (d, J=6.7 Hz, 3H).

SEQ ID NO: 77: Glu-Pro-Val-Gly-Gln-Ala-Lys (Acetate Salt)

High resolution mass spectrometry (Orbitrap-HRMS), molecular formula: $C_{31}H_{53}N_9O_{11}$; m/z: 364.7004 ([M+2H]$^{2+}$), 728.3932 ([M+H]$^{+}$).

$^1$H NMR (600 MHz, $D_2O$) δ 4.40 (dd, J=8.3, 6.5 Hz, 1H), 4.23 (dd, J=7.7, 4.4 Hz, 1H), 4.20-4.15 (m, 2H), 4.01 (dd, J=8.3, 5.1 Hz, 1H), 3.95 (d, J=7.4 Hz, 1H), 3.83-3.76 (m, 2H), 3.63-3.55 (m, 1H), 3.50-3.45 (m, 1H), 2.85 (t, J=7.5 Hz, 2H), 2.32 (t, J=7.2 Hz, 2H), 2.23-2.15 (m, 3H), 2.05-1.67 (m, AcOH, 12H), 1.59-1.50 (m, 3H), 1.26 (dd, J=9.7, 7.5 Hz, 5H), 0.84 (dd, J=14.3, 6.8 Hz, 6H).

SEQ ID NO: 78: D-Glu-Pro-Val-Pro-Gln-Ala-Lys (Acetate Salt)

High resolution mass spectrometry (Orbitrap-HRMS), molecular formula: $C_{34}H_{57}N_9O_{11}$; m/z: 384.716 ($[M+2H]^{2+}$), 768.4245 ($[M+H]^+$).

$^1$H NMR (600 MHz, $D_2O$) δ 4.36 (dd, J=8.8, 4.3 Hz, 1H), 4.29-4.21 (m, 3H), 4.18-4.11 (m, 2H), 4.01 (dd, J=8.2, 5.1 Hz, 1H), 3.78-3.72 (m, 1H), 3.63-3.49 (m, 3H), 2.84 (t, J=7.5 Hz, 2H), 2.28-2.23 (m, 4H), 2.19-2.12 (m, 2H), 1.98-1.66 (m, AcOH, 15H), 1.59-1.50 (m, 3H), 1.25 (dd, J=11.6, 7.4 Hz, 5H), 0.85 (dd, J=15.5, 6.8 Hz, 6H).

SEQ ID NO: 79: Glu-D-Pro-Val-Pro-Gln-Ala-Lys (Acetate Salt)

High resolution mass spectrometry (Orbitrap-HRMS), molecular formula: $C_{34}H_{57}N_9O_{11}$; m/z: 384.7159 ($[M+2H]^{2+}$), 768.4244 ($[M+H]^+$).

$^1$H NMR (600 MHz, $D_2O$) δ 4.36 (dd, J=8.8, 3.9 Hz, 1H), 4.33 (d, J=8.1 Hz, 1H), 4.28 (dd, J=8.3, 6.6 Hz, 1H), 4.23 (dd, J=7.1, 5.1 Hz, 1H), 4.19-4.13 (m, 2H), 4.02 (dd, J=8.2, 5.1 Hz, 1H), 3.76-3.68 (m, 1H), 3.61-3.51 (m, 3H), 2.84 (t, J=7.5 Hz, 2H), 2.31-2.06 (m, 7H), 2.00-1.66 (m, AcOH, 16H), 1.58-1.50 (m, 3H), 1.27-1.23 (m, 5H), 0.81 (dd, J=22.8, 6.7 Hz, 6H).

SEQ ID NO: 80: Glu-Pro-D-Val-Pro-Gln-Ala-Lys (Acetate Salt)

High resolution mass spectrometry (Orbitrap-HRMS), molecular formula: $C_{34}H_{57}N_9O_{11}$; m/z: 384.7158 ($[M+2H]^{2+}$), 768.4241 ($[M+H]^+$).

$^1$H NMR (600 MHz, $D_2O$) δ 4.46 (d, J=7.3 Hz, 1H), 4.36 (dd, J=8.3, 6.6 Hz, 1H), 4.30-4.20 (m, 3H), 4.17 (dd, J=8.1, 6.1 Hz, 1H), 4.03-4.00 (m, 1H), 3.72-3.66 (m, 1H), 3.63-3.57 (m, 2H), 3.53-3.49 (m, 1H), 2.85 (t, J=7.5 Hz, 2H), 2.36-2.21 (m, 6H), 2.18-2.13 (m, 1H), 2.05-1.78 (m, AcOH, 17H), 1.70-1.66 (m, 1H), 1.58-1.51 (m, 3H), 1.28-1.23 (m, 6H), 0.78 (dd, J=15.0, 6.7 Hz, 6H).

SEQ ID NO: 81: Glu-Pro-Val-D-Pro-Gln-Ala-Lys (Acetate Salt)

High resolution mass spectrometry (Orbitrap-HRMS), molecular formula: $C_{34}H_{57}N_9O_{11}$; m/z: 384.7157 ($[M+2H]^{2+}$), 768.4240 ($[M+H]^+$).

$^1$H NMR (600 MHz, $D_2O$) δ 4.43-4.30 (m, 2H), 4.28-4.21 (m, 2H), 4.21-4.13 (m, 2H), 4.03-3.98 (m, 1H), 3.72-3.53 (m, 3H), 3.50-3.44 (m, 1H), 2.85 (t, J=7.5 Hz, 2H), 2.33 (t, J=7.2 Hz, 2H), 2.23-2.11 (m, 4H), 2.07-1.74 (m, AcOH, 14H), 1.73-1.64 (m, 2H), 1.58-1.50 (m, 3H), 1.29-1.23 (m, 5H), 0.81 (dd, J=15.1, 6.7 Hz, 6H).

SEQ ID NO: 82: Glu-Pro-Val-Pro-D-Gln-Ala-Lys (Acetate Salt)

High resolution mass spectrometry (Orbitrap-HRMS), molecular formula: $C_{31}H_{53}N_9O_{11}$; m/z: 384.7158 ($[M+2H]^{2+}$), 768.4242 ($[M+H]^+$).

$^1$H NMR (600 MHz, $D_2O$) δ 4.38 (dd, J=8.3, 6.4 Hz, 1H), 4.27-4.14 (m, 5H), 4.03 (dd, J=8.4, 5.0 Hz, 1H), 3.80-3.75 (m, 1H), 3.62-3.45 (m, 3H), 2.85 (t, J=7.5 Hz, 2H), 2.32 (t, J=7.3 Hz, 2H), 2.24-2.12 (m, 4H), 2.09-1.67 (m, AcOH, 15H), 1.60-1.50 (m, 3H), 1.28 (d, J=7.3 Hz, 5H), 0.88-0.80 (m, 6H).

SEQ ID NO: 83: Glu-Pro-Val-Pro-Gln-D-Ala-Lys (Acetate Salt)

High resolution mass spectrometry (Orbitrap-HRMS), molecular formula: $C_{31}H_{53}N_9O_{11}$; m/z: 384.7159 ($[M+2H]^{2+}$), 768.4243 ($[M+H]^+$).

$^1$H NMR (600 MHz, $D_2O$) δ 4.38 (dd, J=8.3, 6.4 Hz, 1H), 4.28-4.20 (m, 3H), 4.19-4.12 (m, 2H), 4.05 (dd, J=8.6, 5.0 Hz, 1H), 3.77-3.72 (m, 1H), 3.60-3.45 (m, 3H), 2.85-2.80 (m, 2H), 2.32 (t, J=7.2 Hz, 2H), 2.26 (t, J=8.0 Hz, 2H), 2.20-2.12 (m, 2H), 2.08-1.77 (m, AcOH, 13H), 1.75-1.66 (m, 3H), 1.57-1.47 (m, 3H), 1.26-1.18 (m, 5H), 0.85 (dd, J=13.0, 6.7 Hz, 6H).

SEQ ID NO: 84: Glu-Pro-Val-Pro-Gln-Ala-D-Lys (Acetate Salt)

High resolution mass spectrometry (Orbitrap-HRMS), molecular formula: $C_{31}H_{53}N_9O_{11}$; m/z: 384.7160 ($[M+2H]^{2+}$), 768.4246 ($[M+H]^+$).

$^1$H NMR (600 MHz, $D_2O$) δ 4.39 (dd, J=8.3, 6.4 Hz, 1H), 4.30-4.20 (m, 3H), 4.19-4.11 (m, 2H), 4.05 (dd, J=8.3, 4.8 Hz, 1H), 3.79-3.71 (m, 1H), 3.61-3.47 (m, 3H), 2.86-2.81 (m, 2H), 2.32 (t, J=7.2 Hz, 2H), 2.27 (t, J=7.5 Hz, 2H), 2.21-2.12 (m, 2H), 2.05-1.78 (m, AcOH, 12H), 1.78-1.68 (m, 3H), 1.60-1.50 (m, 3H), 1.27-1.20 (m, 5H), 0.86 (dd, J=12.5, 6.7 Hz, 6H).

SEQ ID NO: 85: Lys-Glu-Pro-Val-Pro (Acetate Salt)

High resolution mass spectrometry (Orbitrap-HRMS), molecular formula: $C_{26}H_{44}N_6O_8$; m/z: 454.2655 ($[M+2H]^{2+}$), 569.3287 ($[M+H]^+$).

$^1$H NMR (600 MHz, $D_2O$) δ 4.50 (dd, J=9.9, 4.2 Hz, 1H), 4.36-4.22 (m, 3H), 4.09 (dd, J=8.5, 5.8 Hz, 1H), 3.89 (t, J=6.7 Hz, 1H), 3.70-3.65 (m, 2H), 3.60-3.53 (m, 2H), 3.51-3.26 (m, 1H), 2.87 (d, J=7.5 Hz, 2H), 2.28-2.09 (m, 5H), 2.00-1.68 (m, AcOH, 18H), 1.58-1.55 (m, 2H), 1.35-1.29 (m, 2H), 0.88 (d, J=6.8 Hz, 3H), 0.82 (d, J=6.7 Hz, 3H).

SEQ ID NO: 86: Glu-Pro-Val-Pro-Gln (Acetate Salt)

High resolution mass spectrometry (Orbitrap-HRMS), molecular formula: $C_{25}H_{40}N_6O_9$; m/z: 569.2919 ($[M+H]^+$).

$^1$H NMR (600 MHz, $D_2O$) δ 4.40 (dd, J=8.3, 6.4 Hz, 1H), 4.31-4.23 (m, 3H), 4.09 (dd, J=9.0, 4.8 Hz, 1H), 3.78-3.72 (m, 1H), 3.61-3.48 (m, 3H), 2.41 (t, J=7.3 Hz, 2H), 2.25-2.14 (m, 4H), 2.09-1.70 (m, AcOH, 13H), 0.86 (dd, J=15.3, 6.7 Hz, 6H).

SEQ ID NO: 87: Lys-Glu-Pro-Val-Pro-Gln (Acetate Salt)

High resolution mass spectrometry (Orbitrap-HRMS), molecular formula: $C_{31}H_{52}N_8O_{10}$; m/z: 349.1971 ($[M+2H]^{2+}$), 697.3868 ($[M+H]^+$).

$^1$H NMR (600 MHz, $D_2O$) δ 4.51 (dd, J=9.8, 4.3 Hz, 1H), 4.34-4.25 (m, 3H), 4.03 (dd, J=8.8, 4.7 Hz, 1H), 3.89 (t, J=6.7 Hz, 1H), 3.79-3.65 (m, 2H), 3.63-3.52 (m, 2H), 2.86 (t, J=7.5 Hz, 2H), 2.28-2.13 (m, 6H), 2.00-1.73 (m, AcOH, 17H), 1.60-1.54 (m, 2H), 1.36-1.28 (m, 2H), 0.86 (d, J=6.8 Hz, 3H), 0.83 (d, J=6.6 Hz, 3H).

SEQ ID NO: 88: Val-Pro-Tyr-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{92}H_{152}N_{26}O_{24}$; m/z: 502.2934 ($[M+4H]^{4+}$), 669.3699 ($[M+3H]^{3+}$).

$^1$H NMR (600 MHz, $D_2O$) δ 6.97-6.94 (m, 2H), 6.70-6.66 (m, 2H), 4.44 (dd, J=9.4, 4.8 Hz, 1H), 4.35-4.08 (m, 17H), 4.05-4.00 (m, 2H), 3.96 (d, J=7.6 Hz, 1H), 3.76-3.67 (m, 3H), 3.64-3.53 (m, 3H), 3.48 (dd, J=10.2, 6.3 Hz, 3H), 3.07 (t, J=6.9 Hz, 2H), 2.94 (dd, J=13.6, 6.6 Hz, 1H), 2.88-2.79 (m, 7H), 2.76 (dd, J=13.6, 9.2 Hz, 1H), 2.27 (t, J=7.6 Hz, 2H), 2.21 (t, J=7.6 Hz, 2H), 2.18-2.08 (m, 8H), 2.01-1.45 (m, AcOH, 59H), 1.30-1.10 (m, 16H), 0.95 (d, J=6.9 Hz, 3H), 0.87-0.77 (m, 18H).

SEQ ID NO: 89: pyro-Glu-Leu-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{84}H_{145}N_{25}O_{24}$; m/z: 468.7766 ($[M+4H]^{4+}$), 624.6998 ($[M+3H]^{3+}$), 936.5460 ($[M+2H]^{2+}$).

$^1$H NMR (600 MHz, $D_2O$) δ 4.47-4.42 (m, 2H), 4.32-4.10 (m, 13H), 4.02 (dd, J=8.4, 4.8 Hz, 1H), 3.96 (d, J=7.6 Hz, 1H), 3.82-3.60 (m, 3H), 3.58-3.45 (m, 3H), 3.07 (t, J=6.9 Hz, 2H), 2.90-2.80 (m, 6H), 2.45-2.36 (m, 1H), 2.31-2.24 (m, 4H), 2.23-2.03 (m, 7H), 1.99-1.44 (m, AcOH, 47H), 1.39-1.19 (m, 15H), 0.85 (dd, J=12.5, 6.8 Hz, 6H), 0.81-0.77 (m, 9H), 0.75 (d, J=6.0 Hz, 3H).

SEQ ID NO: 90: Pro-Ala-Tyr-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{90}H_{148}N_{26}O_{24}$; m/z: 495.2855 ($[M+4H]^{4+}$), 660.0449 ($[M+3H]^{3+}$), 989.5637 ($[M+2H]^{2+}$).

$^1$H NMR (600 MHz, $D_2O$) δ 6.99-6.92 (m, 2H), 6.71-6.64 (m, 2H), 4.47-4.42 (m, 1H), 4.36 (t, J=7.8 Hz, 1H), 4.32-4.06 (m, 15H), 4.04-3.99 (m, 1H), 3.96 (d, J=7.6 Hz, 1H), 3.79-3.65 (m, 3H), 3.60-3.46 (m, 3H), 3.30-3.22 (m, 2H), 3.07 (t, J=6.9 Hz, 2H), 2.89-2.79 (m, 8H), 2.33-2.06 (m, 11H), 1.99-1.45 (m, AcOH, 51H), 1.39-1.14 (m, 19H), 0.87-0.77 (m, 12H).

SEQ ID NO: 91: Arg-Lys-Asp-Val-Tyr-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{103}H_{174}N_{32}O_{28}$; m/z: 578.0856 ($[M+4H]^{4+}$), 770.4463 ($[M+3H]^{3+}$), 1155.1642 ($[M+2H]^{2+}$).

$^1$H NMR (600 MHz, $D_2O$) δ 6.96 (d, J=8.5 Hz, 2H), 6.70-6.64 (m, 2H), 4.50-4.43 (m, 2H), 4.38 (t, J=8.0 Hz, 1H), 4.30-4.11 (m, 13H), 4.02 (dd, J=8.4, 4.9 Hz, 1H), 3.96 (d, J=7.6 Hz, 1H), 3.94-3.90 (m, 2H), 3.79-3.65 (m, 3H), 3.62-3.46 (m, 3H), 3.11-3.05 (m, 4H), 2.88-2.79 (m, 10H), 2.51 (dd, J=15.9, 5.3 Hz, 1H), 2.42 (dd, J=16.0, 8.5 Hz, 1H), 2.29-2.11 (m, 9H), 1.99-1.64 (m, AcOH, 45H), 1.63-1.45 (m, 19H), 1.41-1.14 (m, 18H), 0.87-0.77 (m, 12H), 0.72 (d, J=6.7 Hz, 6H).

SEQ ID NO: 92: Arg-Lys-Asp-Val-Tyr-Lys-Glu-Pro-Val-Pro-Gln-Ala-Lys (Acetate Salt)

High resolution mass spectrometry (Orbitrap-HRMS), molecular formula: $C_{70}H_{116}N_{20}O_{20}$; m/z: 390.2233 ($[M+4H]^{4+}$), 519.9619 ($[M+3H]^{3+}$), 779.4393 ($[M+2H]^{2+}$).

$^1$H NMR (600 MHz, $D_2O$) δ 6.96 (d, J=8.6 Hz, 2H), 6.67 (d, J=8.5 Hz, 2H), 4.49 (dd, J=8.4, 5.3 Hz, 1H), 4.38 (t, J=8.0 Hz, 1H), 4.31-4.23 (m, 5H), 4.19-4.10 (m, 3H), 4.01 (dd, J=8.2, 5.1 Hz, 1H), 3.93-3.89 (m, 2H), 3.77-3.67 (m, 2H), 3.61-3.50 (m, 2H), 3.10-3.05 (m, 2H), 2.86-2.79 (m, 8H), 2.51 (dd, J=16.0, 5.3 Hz, 1H), 2.42 (dd, J=15.9, 8.5 Hz, 1H), 2.28-2.20 (m, 4H), 2.18-2.10 (m, 2H), 1.97-1.65 (m, AcOH, 29H), 1.61-1.45 (m, 13H), 1.26 (dd, J=11.1, 7.4 Hz, 10H), 0.83 (dd, J=19.0, 6.7 Hz, 6H), 0.72 (d, J=5.6 Hz, 6H).

SEQ ID NO: 93: Arg-Lys-Asp-Val-Tyr-Glu-Pro-Val-Pro-Gln-Ala-Lys (Acetate Salt)

High resolution mass spectrometry (Orbitrap-HRMS), molecular formula: $C_{64}H_{104}N_{18}O_{19}$; m/z: 715.3917 ($[M+2H]^{2+}$).

$^1$H NMR (600 MHz, $D_2O$) δ 6.96 (d, J=8.6 Hz, 2H), 6.66 (d, J=8.5 Hz, 2H), 4.48-4.42 (m, 3H), 4.26-4.12 (m, 6H), 4.02 (dd, J=8.2, 5.0 Hz, 1H), 3.95-3.89 (m, 2H), 3.77-3.68 (m, 1H), 3.56-3.47 (m, 2H), 3.43-3.36 (m, 1H), 3.10-3.04 (m, 2H), 2.87-2.80 (m, 6H), 2.54 (dd, J=16.0, 5.1 Hz, 1H), 2.45 (dd, J=16.0, 8.4 Hz, 1H), 2.27 (t, J=7.6 Hz, 2H), 2.17-2.08 (m, 4H), 1.98-1.66 (m, AcOH, 27H), 1.65-1.45 (m, 9H), 1.26 (dd, J=11.3, 7.4 Hz, 7H), 0.84 (dd, J=13.0, 6.7 Hz, 6H), 0.70 (dd, J=6.8, 2.8 Hz, 6H).

SEQ ID NO: 94: Arg-Lys-Asp-Val-Tyr-Pro-Val-Pro-Gln (Acetate Salt)

High resolution mass spectrometry (Orbitrap-HRMS), molecular formula: $C_{50}H_{80}N_{14}O_{14}$; m/z: 367.8727 ($[M+3H]^{3+}$), 551.3051 ($[M+2H]^{2+}$), 1101.6030 ($[M+H]^{+}$).

$^1$H NMR (600 MHz, $D_2O$) δ 4.45 (dd, J=8.9, 4.8 Hz, 1H), 4.36-4.22 (m, 4H), 4.04-3.98 (m, 1H), 3.90 (dd, J=7.0, 5.8 Hz, 2H), 3.76 (dd, J=10.1, 6.4 Hz, 1H), 3.69-3.63 (m, 1H), 3.60-3.43 (m, 2H), 3.09-3.05 (m, 2H), 2.95 (dd, J=14.3, 5.2 Hz, 1H), 2.86-2.82 (m, 2H), 2.74-2.67 (m, 1H), 2.52-2.31 (m, 2H), 2.22-2.08 (m, 4H), 1.99-1.46 (m, AcOH, 29H), 1.32-1.23 (m, 2H), 0.90-0.81 (m, 6H), 0.75 (dd, J=10.3, 6.8 Hz, 2H), 0.67 (dd, J=17.1, 6.7 Hz, 4H).

SEQ ID NO: 95: Gly-Pro-Glu-Thr-Ala-Phe-Leu-Arg-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{113}H_{188}N_{34}O_{31}$; m/z: 504.6906 ($[M+5H]^{5+}$), 630.6115 ($[M+4H]^{4+}$), 840.4796 ($[M+3H]^{3+}$).

$^1$H NMR (600 MHz, $D_2O$) δ 7.22 (t, J=7.4 Hz, 2H), 7.16 (t, J=7.3 Hz, 1H), 7.12-7.07 (m, 2H), 4.47-4.41 (m, 3H), 4.35-4.03 (m, 19H), 4.02 (dd, J=8.4, 4.8 Hz, 1H), 3.95 (d, J=3.6 Hz, 1H), 3.86 (s, 1H), 3.75 (s, 1H), 3.68 (t, J=8.5 Hz, 2H), 3.58-3.42 (m, 5H), 3.06 (t, J=6.9 Hz, 4H), 2.91-2.81 (m, 7H), 2.29-2.11 (m, 12H), 2.00-1.19 (m, AcOH, 80H), 1.14 (d, J=7.1 Hz, 3H), 1.06 (d, J=6.3 Hz, 3H), 0.84 (dd, J=13.7, 6.7 Hz, 6H), 0.81-0.76 (m, 9H), 0.72 (d, J=5.6 Hz, 3H).

SEQ ID NO: 96: Gly-Pro-Glu-Thr-Ala-Phe-Leu-Arg-Glu-Pro-Val-Pro-Gln-Ala-Lys (Acetate Salt)

High resolution mass spectrometry (Orbitrap-HRMS), molecular formula: $C_{74}H_{118}N_{20}O_{22}$; m/z: 547.2972 ($[M+3H]^{3+}$), 820.4424 ($[M+2H]^{2+}$).

$^1$H NMR (600 MHz, $D_2O$) δ 7.21 (dd, J=8.2, 6.6 Hz, 2H), 7.16 (t, J=7.3 Hz, 1H), 7.12-7.07 (m, 2H), 4.50-4.42 (m, 2H), 4.36-4.22 (m, 4H), 4.21-4.09 (m, 7H), 4.07-4.00 (m, 2H), 3.93 (d, J=16.5 Hz, 1H), 3.84 (d, J=16.5 Hz, 1H), 3.78-3.70 (m, 1H), 3.68-3.60 (m, 1H), 3.56-3.42 (m, 4H), 3.10-2.97 (m, 3H), 2.90-2.82 (m, 3H), 2.29-2.09 (m, 9H), 2.00-1.81 (m, AcOH, 19H), 1.77-1.66 (m, 5H), 1.61-1.37 (m, 9H), 1.26 (dd, J=11.9, 7.4 Hz, 5H), 1.14 (d, J=7.2 Hz, 3H), 1.05 (d, J=6.4 Hz, 3H), 0.84 (dd, J=15.5, 6.7 Hz, 6H), 0.77 (d, J=5.9 Hz, 3H), 0.72 (d, J=5.7 Hz, 3H).

SEQ ID NO: 97: Ser-Ser-Glu-Asp-Ile-Lys-Glu-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{105}H_{179}N_{31}O_{35}$; m/z: 488.0708 ($[M+5H]^{5+}$), 609.8367 ($[M+4H]^{4+}$), 812.7799 ($[M+3H]^{3+}$).

$^1$H NMR (600 MHz, $D_2O$) δ 4.48-4.41 (m, 3H), 4.34 (t, J=5.4 Hz, 1H), 4.31 (dd, J=8.4, 5.8 Hz, 1H), 4.28-4.22 (m, 3H), 4.22-4.09 (m, 11H), 4.04-3.88 (m, 5H), 3.81-3.72 (m, 3H), 3.71-3.62 (m, 2H), 3.59-3.43 (m, 3H), 3.07 (t, J=6.9 Hz, 2H), 2.90-2.80 (m, 8H), 2.58 (dd, J=16.0, 6.3 Hz, 1H), 2.48 (dd, J=16.0, 7.9 Hz, 1H), 2.29-2.09 (m, 13H), 2.00-1.47 (m, AcOH, 51H), 1.40-1.20 (m, 18H), 1.12-1.05 (m, 1H), 0.89-0.70 (m, 18H).

SEQ ID NO: 98: Ser-Ser-Glu-Asp-Ile-Lys-Glu-Glu-Pro-Val-Pro-Gln-Ala-Lys (Acetate Salt)

High resolution mass spectrometry (Orbitrap-HRMS), molecular formula: $C_{66}H_{109}N_{17}O_{26}$; m/z: 519.5973 ($[M+3H]^{3+}$), 778.8925 ($[M+2H]^{2+}$).

$^1$H NMR (600 MHz, $D_2O$) δ 4.54-4.47 (m, 2H), 4.37-4.30 (m, 2H), 4.27-4.10 (m, 8H), 4.05-3.99 (m, 2H), 3.94-3.88 (m, 2H), 3.79-3.73 (m, 3H), 3.70-3.62 (m, 1H), 3.61-3.50 (m, 2H), 2.85 (t, J=7.6 Hz, 4H), 2.63 (dd, J=16.2, 6.2 Hz, 1H), 2.51 (dd, J=16.2, 7.9 Hz, 1H), 2.37-2.06 (m, 11H), 1.99-1.49 (m, AcOH, 30H), 1.34-1.24 (m, 8H), 1.10-1.01 (m, 1H), 0.84 (dd, J=13.8, 6.7 Hz, 6H), 0.77-0.71 (m, 6H).

SEQ ID NO: 99: Ser-Ser-Glu-Asp-Ile-Lys-Glu-Pro-Val-Pro-Gln (Acetate Salt)

High resolution mass spectrometry (Orbitrap-HRMS), molecular formula: $C_{52}H_{55}N_{13}O_{21}$; m/z: 614.806 ($[M+2H]^{2+}$), 1228.605 ($[M+H]^{+}$).

$^{1}$H NMR (600 MHz, $D_2O$) δ 4.54-4.48 (m, 2H), 4.36 (t, J=5.5 Hz, 1H), 4.34-4.24 (m, 3H), 4.23-4.18 (m, 2H), 4.12-4.05 (m, 2H), 4.01 (d, J=7.9 Hz, 1H), 3.94-3.88 (m, 2H), 3.79-3.72 (m, 3H), 3.70-3.62 (m, 1H), 3.60-3.50 (m, 2H), 2.85 (t, J=7.6 Hz, 2H), 2.65 (dd, J=16.3, 6.0 Hz, 1H), 2.53 (dd, J=16.4, 8.0 Hz, 1H), 2.40-2.03 (m, 9H), 2.01-1.51 (m, AcOH, 21H), 1.34-1.22 (m, 3H), 1.08-1.01 (m, 1H), 0.89-0.80 (m, 6H), 0.76-0.70 (m, 6H).

SEQ ID NO: 100: Val-Pro-Pro-Lys-Glu-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{88}H_{150}N_{26}O_{23}$; m/z: 389.0348 ($[M+5H]^{5+}$), 480.0415 ($[M+4H]^{4+}$), 647.7197 ($[M+3H]^{3+}$).

$^{1}$H NMR (600 MHz, $D_2O$) δ 4.49-4.42 (m, 2H), 4.34-4.06 (m, 13H), 4.05-4.00 (m, 2H), 3.96 (d, J=7.6 Hz, 1H), 3.80-3.73 (m, 1H), 3.69 (d, J=9.8 Hz, 4H), 3.58-3.45 (m, 5H), 3.07 (t, J=6.9 Hz, 2H), 2.88-2.83 (m, 6H), 2.27 (t, J=7.7 Hz, 3H), 2.20-2.11 (m, 9H), 2.01-1.45 (m, AcOH, 55H), 1.24 (dd, J=21.5, 7.2 Hz, 16H), 0.97 (d, J=6.9 Hz, 3H), 0.88-0.78 (m, 15H).

SEQ ID NO: 101: Glu-Pro-Val-Pro-Gln-Ala-Lys-Ser-Ser-Glu-Asp-Ile-Lys-Glu (Acetate Salt)

High resolution mass spectrometry (Orbitrap-HRMS), molecular formula: $C_{66}H_{109}N_{17}O_{26}$; m/z: 519.5978 ($[M+3H]^{3+}$), 778.8933 ($[M+2H]^{2+}$).

$^{1}$H NMR (600 MHz, $D_2O$) δ 4.50 (dd, J=8.0, 6.0 Hz, 1H), 4.40 (dd, J=8.4, 6.4 Hz, 1H), 4.36-4.30 (m, 2H), 4.27-4.19 (m, 6H), 4.18-4.11 (m, 2H), 4.08 (dd, J=8.8, 4.9 Hz, 1H), 4.01 (d, J=8.1 Hz, 1H), 3.82-3.71 (m, 5H), 3.62-3.47 (m, 3H), 2.86 (t, J=7.5 Hz, 4H), 2.65 (dd, J=16.4, 6.0 Hz, 1H), 2.51 (dd, J=16.3, 8.1 Hz, 1H), 2.34 (t, J=7.2 Hz, 2H), 2.31-2.10 (m, 9H), 2.06-1.52 (m, AcOH, 28H), 1.35-1.23 (m, 8H), 1.08-1.00 (m, 1H), 0.86 (dd, J=11.5, 6.7 Hz, 6H), 0.76-0.70 (m, 6H).

SEQ ID NO: 102: Glu-Pro-Val-Pro-Gln-Ala-Lys-Val-Pro-Tyr (Acetate Salt)

High resolution mass spectrometry (Orbitrap-HRMS), molecular formula: $C_{53}H_{82}N_{12}O_{15}$; m/z: 564.3073 ($[M+2H]^{2+}$).

$^{1}$H NMR (600 MHz, $D_2O$) δ 7.01-6.95 (m, 2H), 6.69 (d, J=8.5 Hz, 2H), 4.40 (dd, J=8.3, 6.4 Hz, 1H), 4.29-4.10 (m, 9H), 3.79-3.71 (m, 1H), 3.68-3.45 (m, 5H), 2.92-2.81 (m, 4H), 2.33 (t, J=7.3 Hz, 2H), 2.26 (t, J=7.7 Hz, 2H), 2.20-2.13 (m, 2H), 2.06-1.52 (m, AcOH, 25H), 1.33-1.21 (m, 5H), 0.86 (dd, J=11.3, 6.7 Hz, 6H), 0.77 (dd, J=17.6, 6.7 Hz, 6H).

SEQ ID NO: 103: Lys-Glu-Pro-Val-Pro-Gln-Ala-Lys-Pro-Arg-Lys-Val-Ala-Ala-Glu (Acetate Salt)

High resolution mass spectrometry (Orbitrap-HRMS), molecular formula: $C_{73}H_{126}N_{22}O_{21}$; m/z: 824.4799 ($[M+2H]^{2+}$).

$^{1}$H NMR (600 MHz, $D_2O$) δ 4.49 (dd, J=9.6, 4.4 Hz, 1H), 4.45 (dd, J=9.4, 4.9 Hz, 1H), 4.36-4.05 (m, 11H), 4.01-3.96 (m, 2H), 3.92-3.87 (m, 1H), 3.82-3.64 (m, 3H), 3.60-3.46 (m, 3H), 3.07 (t, J=7.0 Hz, 2H), 2.88-2.83 (m, 6H), 2.29-2.09 (m, 9H), 1.99-1.46 (m, AcOH, 47H), 1.39-1.20 (m, 16H), 0.85 (dd, J=14.2, 6.7 Hz, 6H), 0.80 (dd, J=6.7, 3.7 Hz, 6H).

SEQ ID NO: 104: Lys-Glu-Pro-Val-Pro-Gln-Ala-Lys-Pro-Arg-Lys-Val-Ala-Ala-Asn (Acetate Salt)

High resolution mass spectrometry (Orbitrap-HRMS), molecular formula: $C_{72}H_{125}N_{23}O_{20}$; m/z: 408.9938 ($[M+4H]^{4+}$), 544.9891 ($[M+3H]^{3+}$), 816.9801 ($[M+2H]^{2+}$).

$^{1}$H NMR (600 MHz, $D_2O$) δ 4.49 (dd, J=9.7, 4.4 Hz, 1H), 4.45 (dd, J=9.4, 4.8 Hz, 1H), 4.34-4.10 (m, 11H), 3.96 (d, J=7.6 Hz, 1H), 3.92-3.84 (m, 1H), 3.78-3.66 (m, 3H), 3.62-3.43 (m, 3H), 3.07 (t, J=6.9 Hz, 2H), 2.90-2.82 (m, 6H), 2.63 (dd, J=15.1, 4.9 Hz, 1H), 2.53 (dd, J=15.1, 8.1 Hz, 1H), 2.30-2.11 (m, 7H), 2.03-1.42 (m, AcOH, 44H), 1.39-1.19 (m, 15H), 0.85 (dd, J=14.0, 6.7 Hz, 6H), 0.80 (dd, J=6.8, 3.0 Hz, 6H).

SEQ ID NO: 105: Lys-Gln-Pro-Val-Pro-Gln-Ala-Lys-Pro-Arg-Lys-Val-Ala-Ala-Gln (Acetate Salt)

High resolution mass spectrometry (Orbitrap-HRMS), molecular formula: $C_{73}H_{128}N_{24}O_{19}$; m/z: 412.2515 ($[M+4H]^{4+}$), 549.3327 ($[M+3H]^{3+}$), 823.4955 ($[M+2H]^{2+}$).

$^{1}$H NMR (600 MHz, $D_2O$) δ 4.53 (dd, J=9.0, 5.0 Hz, 1H), 4.44 (dd, J=9.4, 4.8 Hz, 1H), 4.34 (dd, J=8.4, 6.0 Hz, 1H), 4.30-4.23 (m, 3H), 4.22-4.11 (m, 6H), 4.02 (dd, J=8.4, 4.8 Hz, 1H), 3.96 (d, J=7.6 Hz, 1H), 3.90 (t, J=6.7 Hz, 1H), 3.80-3.63 (m, 3H), 3.60-3.42 (m, 3H), 3.07 (t, J=6.9 Hz, 2H), 2.89-2.82 (m, 6H), 2.34-2.24 (m, 4H), 2.22-2.07 (m, 5H), 2.01-1.45 (m, AcOH, 50H), 1.39-1.20 (m, 15H), 0.85 (dd, J=15.5, 6.7 Hz, 6H), 0.80 (dd, J=6.8, 4.3 Hz, 6H).

SEQ ID NO: 106: Lys-Glu-Pro-Ile-Pro-Gln-Ala-Lys-Pro-Arg-Lys-Val-Ala-Ala-Gln (Acetate Salt)

High resolution mass spectrometry (Orbitrap-HRMS), molecular formula: $C_{74}H_{129}N_{23}O_{20}$; m/z: 416.0015 ($[M+4H]^{4+}$), 554.3328 ($[M+3H]^{3+}$), 830.9956 ($[M+2H]^{2+}$).

$^{1}$H NMR (600 MHz, $D_2O$) δ 4.50 (dd, J=9.6, 4.4 Hz, 1H), 4.45 (dd, J=9.3, 4.9 Hz, 1H), 4.36-4.22 (m, 4H), 4.22-4.10 (m, 6H), 4.02 (dd, J=8.4, 4.9 Hz, 1H), 3.96 (d, J=7.6 Hz, 1H), 3.92-3.84 (m, 1H), 3.82-3.74 (m, 1H), 3.73-3.63 (m, 2H), 3.61-3.41 (m, 3H), 3.07 (t, J=6.9 Hz, 2H), 2.90-2.82 (m, 6H), 2.32-2.12 (m, 9H), 2.00-1.46 (m, AcOH, 46H), 1.43-1.05 (m, 17H), 0.84 (d, J=6.8 Hz, 3H), 0.80 (dd, J=6.8, 4.3 Hz, 6H), 0.75 (t, J=7.4 Hz, 3H).

SEQ ID NO: 107: Val-Pro-Gln-Ala (Acetate Salt)

High resolution mass spectrometry (Orbitrap-HRMS), molecular formula: $C_{18}H_{31}N_5O_6$; m/z: 414.2341 ($[M+1H]^{+}$).

$^{1}$H NMR (600 MHz, $D_2O$) δ 4.29 (t, J=7.6 Hz, 1H), 4.07 (dd, J=8.5, 6.1 Hz, 1H), 4.01-3.91 (m, 2H), 3.61-3.53 (m, 1H), 3.46-3.41 (m, 1H), 2.24-2.10 (m, 4H), 1.95-1.69 (m, AcOH, 6H), 1.14 (d, J=7.3 Hz, 3H), 0.91 (d, J=7.0 Hz, 3H), 0.80 (d, J=6.8 Hz, 3H).

SEQ ID NO: 108: Val-Pro-Gln-Ala-Lys (Acetate Salt)

High resolution mass spectrometry (Orbitrap-HRMS), molecular formula: $C_{24}H_{43}N_7O_7$; m/z: 271.6681 ([M+2H] 2+), 542.3289 ($[M+1H]^{+}$).

$^{1}$H NMR (600 MHz, $D_2O$) δ 4.28 (t, J=7.6 Hz, 1H), 4.13-4.06 (m, 2H), 3.99 (d, J=5.5 Hz, 1H), 3.94 (dd, J=8.2, 5.1 Hz, 1H), 3.60-3.54 (m, 1H), 3.46-3.41 (m, 1H), 2.78 (t, J=7.5 Hz, 2H), 2.21 (t, J=7.6 Hz, 2H), 2.17-2.09 (m, 2H), 1.93-1.58 (m, AcOH, 11H), 1.53-1.44 (m, 3H), 1.20 (dd, J=9.7, 7.5 Hz, 5H), 0.91 (d, J=6.9 Hz, 3H), 0.80 (d, J=6.9 Hz, 3H).

Example 2: Experiment on the Efficacy of Polypeptide Compounds in Relieving Colitis Experimental Animals:

Wild-type AB strain zebrafishes, bred by natural pair mating.

Zebrafishes aged 3 days post fertilization (3 dpf). Zebrafishes were kept in fish farming water at 28° C. (water quality: 200 mg of instant sea salt in each 1 L of reverse osmosis water, with the conductivity of 450-550 μS/cm; pH of 6.5-8.5; and hardness of 50-100 mg/L $CaCO_3$), the experimental animal use license number is: SYXK (Zhe) 2012-0171, and the breeding management met the requirements of the international AAALAC certification (certification number: 001458).

Experimental Method:

(1) Grouping: Polypeptide group: prepared into a stock solution of 20.0 mg/mL with ultrapure water and stored at −20° C.

Positive control group: prednisone, as white powder, with batch number C10016501, Shanghai Macklin Biochemical Technology Co., Ltd., stored at 4° C.; prepared into a 15.0 mg/mL stock solution with DMSO, and stored in aliquots at −20° C.

Normal control group and model control group.

(2) Experimental method: 3 dpf wild-type AB strain zebrafishes were randomly selected and placed in a 6-well plate, with 30 zebrafishes in each well (experimental group). Except for the normal control group, all other experimental groups were given TNBS in water to establish the zebrafish model of intestinal mucosal injury. After 2 days of treatment at 28° C., TNBS was removed, and polypeptide compound in water (at concentrations shown in Table 4) was given respectively, and for the positive control, prednisone was 15.0 μg/mL. A normal control group (healthy group) and a model control group (intestinal mucosal injury group) were set up at the same time. The capacity of each well (experimental group) was 3 mL. After 2 days of treatment at 28° C., 10 zebrafishes were randomly selected from each experimental group and photographed under a dissecting microscope. NIS-Elements D 3.20 advanced image processing software was used to analyze and collect data, and the intestinal lumen area of the zebrafish was analyzed. The statistical analysis results of this indicator were used to evaluate the efficacy of the samples in relieving colitis. The statistics results were expressed as mean±SE. SPSS26.0 software was used for statistical analysis, and p<0.05 indicates statistically significant difference.

Experimental Results:

The results of the efficacy of the polypeptide compound in relieving colitis are shown in Table 4:

TABLE 4

Results of the experimental evaluation of the efficacy of polypeptide compounds in relieving colitis (n = 10)

| Group | Concentration (μg/mL) | Intestinal lumen area (pixels, mean ± SE) |
|---|---|---|
| Normal control group | — | 32743 ± 1560*** |
| Model control group | — | 41868 ± 1671 |
| Prednisone group | 15.0 | 34929 ± 1913* |
| SEQ ID NO: 1 | 250 | 39333 ± 2095 |
| | 500 | 26497 ± 1245*** |
| | 1000 | 26174 ± 1898*** |
| SEQ ID NO: 4 | 250 | 48915 ± 2720 |
| | 500 | 40432 ± 3736 |
| | 1000 | 33664 ± 3758* |
| SEQ ID NO: 5 | 250 | 42960 ± 2661 |
| | 500 | 45713 ± 4481 |
| | 1000 | 33977 ± 3524* |
| SEQ ID NO: 6 | 250 | 53093 ± 3839 |
| | 500 | 45831 ± 3894 |
| | 1000 | 28429 ± 3711** |
| SEQ ID NO: 12 | 250 | 48857 ± 5649 |
| | 500 | 43802 ± 3228 |
| | 1000 | 26727 ± 2106** |

TABLE 4-continued

Results of the experimental evaluation of the efficacy of polypeptide compounds in relieving colitis (n = 10)

| Group | Concentration (μg/mL) | Intestinal lumen area (pixels, mean ± SE) |
|---|---|---|
| SEQ ID NO: 15 | 250 | 40719 ± 4647 |
| | 500 | 31319 ± 5274* |
| | 1000 | 30268 ± 2437* |

Compared with the model control group, *p < 0.05, p < 0.01, *p < 0.001

According to the data in Table 4, it can be known that the polypeptide compound groups including SEQ ID NO: 1, 4, 5, 6, 12 and 15 showed significant statistical differences compared with the model control group (p<0.05; p<0.01; p<0.001), and the effect was better than that of the prednisone group. The experimental results show that the polypeptide compound provided in the present application has the effect of alleviating colitis, which is specifically manifested in significantly alleviating intestinal lumen dilatation.

The concentration gradient of the test substances set in this experimental system was 250 μg/mL, 500 μg/mL, and 1000 μg/mL. By counting the intestinal lumen area of the zebrafish after intervention in each group, it can be seen that most of the test substances with the effect of relieving colitis had a more obvious effect at a concentration of 1000 μg/mL (p<0.05; p<0.01; p<0.001). When the concentration of the test substance was further increased for intervention, the death phenomenon of zebrafishes was found in the group; therefore, in the subsequent rounds of activity evaluation, each test polypeptide compound was uniformly administered at 1000 μg/mL for intervention. The results are summarized in Table 5.

TABLE 5

Summary of the activity of polypeptide compounds in alleviating intestinal lumen dilatation of colitis in zebrafishes

| SEQ ID NO: | Activity in relieving intestinal lumen dilatation |
|---|---|
| 1 | *** |
| 2 | ND |
| 3 | ND |
| 4 | * |
| 5 | * |
| 6 | ** |
| 7 | + |
| 8 | + |
| 9 | * |
| 10 | * |
| 11 | + |
| 12 | ** |
| 13 | − |
| 14 | + |
| 15 | * |
| 16 | + |
| 17 | + |
| 18 | − |
| 19 | + |
| 20 | & |
| 21 | + |
| 22 | + |
| 23 | + |
| 24 | + |
| 25 | * |
| 26 | * |
| 27 | + |
| 28 | + |
| 29 | * |

TABLE 5-continued

Summary of the activity of polypeptide compounds in alleviating intestinal lumen dilatation of colitis in zebrafishes

| SEQ ID NO: | Activity in relieving intestinal lumen dilatation |
|---|---|
| 30 | + |
| 31 | * |
| 32 | + |
| 33 | + |
| 34 | * |
| 35 | – |
| 36 | + |
| 37 | + |
| 38 | * |
| 39 | + |
| 40 | + |
| 41 | + |
| 42 | + |
| 43 | ND |
| 44 | – |
| 45 | # |
| 46 | + |
| 47 | + |
| 48 | * |
| 49 | * |
| 50 | * |
| 51 | * |
| 52 | + |
| 53 | * |
| 54 | ** |
| 55 | * |
| 56 | ND |
| 57 | ** |
| 58 | + |
| 59 | + |
| 60 | – |
| 61 | ND |
| 62 | * |
| 63 | *** |
| 64 | + |
| 65 | * |
| 66 | * |
| 67 | * |
| 68 | ** |
| 69 | + |
| 70 | * |
| 71 | + |
| 72 | ** |
| 73 | ND |
| 74 | + |
| 75 | * |
| 76 | + |
| 77 | – |
| 78 | + |
| 79 | + |
| 80 | + |
| 81 | + |
| 82 | + |
| 83 | * |
| 84 | + |
| 85 | * |
| 86 | * |
| 87 | + |
| 88 | * |
| 89 | ** |
| 90 | * |
| 91 | + |
| 92 | ** |
| 93 | * |
| 94 | ** |
| 95 | ** |
| 96 | *** |
| 97 | ** |
| 98 | ** |
| 99 | * |
| 100 | *** |
| 101 | ND |
| 102 | + |
| 103 | * |
| 104 | *** |
| 105 | ** |
| 106 | ** |
| 107 | ND |
| 108 | ND |

Note:
The activity of each compound to relieve intestinal lumen dilatation of colitis in zebrafishes was completed in several batches of trials, and for comparison purposes, its activity against intestinal lumen dilatation was compared with that of the control group of an equivalent number of batches of the experimental model: *$p < 0.05$, $p < 0.01$, *$p < 0.001$; ND indicates not detected, "–" indicates absence of activity, "+" indicates some relief of intestinal lumen dilatation, "#" indicates that all the zebrafishes died in the experiment, and "&" indicates that 13 zebrafishes died in the experiment.

According to the data in Table 4 and Table 5, there was a significant statistical difference between the polypeptide groups and the model control group ($p<0.05$, $p<0.01$ or $p<0.001$), and the effect was better than that of the prednisone group. Under the experimental conditions, SEQ ID NO: 1, 4-6, 9, 10, 12, 15, 25, 26, 29, 31, 34, 38, 48-51, 53-55, 57, 62, 63, 65-68, 70, 72, 75, 83, 85, 86, 88-90, 92-100, and 103-106 all had a significant effect of alleviating colitis, as manifested by relieving intestinal lumen dilatation ($p<0.05$); and SEQ ID NO: 7, 8, 11, 14, 16, 17, 19, 21-24, 27, 28, 30, 32, 33, 36, 37, 39-42, 46, 47, 52, 58, 59, 64, 69, 71, 74, 76, 78-82, 84, 87, 91 and 102 had a certain effect of alleviating intestinal lumen dilatation.

Example 3: Evaluation of the Therapeutic Effects of Polypeptide Compounds on TNBS-Induced Model of Acute Inflammatory Bowel Disease (UC) in SD Rat Objective:

To evaluation the therapeutic effects of polypeptide compounds on TNBS-induced model of acute inflammatory bowel disease in SD rat Materials and Methods:

In this experiment, a rat model of ulcerative colitis was established by administering trinitrobenzene sulfonic acid (TNBS) to laboratory animal male SD rats for a single enema intervention. Acute colitis in rats induced by trinitrobenzene sulfonic acid (TNBS) is an immune response induced by cytokines secreted by Thl type cells. The colon of animals in the model control group shows the reactivity of obvious atrophy and intestinal wall thickening, and the ratio of colon weight to length increases significantly. Fissure-like ulcer foci are observed on the surface of the intestinal mucosa, and typical granulomas are observed in the submucosal layer and muscular layer, internally accompanied by infiltration of inflammatory cells mainly composed of lymphocytes and plasma cells. At the same time, there is obvious hyperplasia of small blood vessels and connective tissue (fibroblasts), and crypt structure destruction and bleeding are observed around the ulcer foci. This model is simple to establish and has good reproducibility. It is an experimental animal model widely used in evaluating drugs for the treatment of inflammatory bowel disease. The experimental animals (male SD rats) were randomly divided into 6 groups according to body weight parameters on the first day of the experiment, namely normal control group, model control group, positive drug mesalazine treatment group, SEQ ID NO: 1 low-dose treatment group, SEQ ID NO: 1 high-dose treatment group, SEQ ID NO: 6 low-dose treatment group, SEQ ID NO: 6 high-dose treatment group and SEQ ID NO: 12 treatment group, with 10 rats in each group. On the day of grouping (DO), except for the normal control group which was given the vehicle, the animals in the remaining experimental groups were given TNBS in ethanol by enema to induce the model; the test article and positive control drug treatments were started on the second day of model induction, with the treatment dose being respectively 3.0 mg/kg and 6.0 mg/kg for SEQ ID NO: 1, respectively 1.4 mg/kg and 2.8 mg/kg for SEQ ID NO: 6, 0.8 mg/kg for SEQ ID NO: 12, and 30.0 mg/kg for positive control drug mesalazine, all of which were administered by enema at a frequency of once a day for 14 consecutive days. During the experimental treatment period (D1-D14), the body weight and general clinical observation indicators (including but not limited to food intake, water intake, activity level and defecation, etc.) of the animals in each experimental group were dynamically collected. At the same time, based on the relevant scoring standards for the disease activity index of ulcerative colitis, the reactivity such as the weight loss degree, stool morphology and trait, and bloody stool of the animals in each experimental group after TNBS induction were scored, and the disease activity index (DAI) of ulcerative colitis was calculated, once a day for 14 consecutive days. At the end point of the experiment, colon tissues of animals in each experimental group were collected, and the length and weight of the colon were measured and then the non-autopsy images were collected. Then the colon was cut open along the intestinal wall longitudinally and autopsy images were collected. Based on the "Criteria for Scoring Gross Morphological Manifestations of the Colon", the gross damage with respect to colon adhesions, colon ulcers and inflammation of animals in each experimental group was observed and scored. Ulcer images were collected under a stereomicroscope and the area of colon ulcer foci was calculated, followed by routine fixation. According to the statistical analysis results of various pharmacodynamic test indicators, the therapeutic effect of the test polypeptide compound on the ulcerative colitis disease model under the set treatment regimen was evaluated.

Results and Conclusions:

In this experimental research system, the animals in the model control group showed obvious disease characteristics of ulcerative colitis, including weight gain inhibition, soft and loose stools, significantly increased ulcerative colitis disease activity index (DAI) score, and macroscopically observed colon atrophy and typical ulcer foci and colon fusion ulcer foci. The test SEQ ID NO: 1 had a significant effect of improving the weight gain inhibition of the model animals under the set treatment regimen, and the degree of improvement was statistically significant compared with the weight change degree of the animals in the model control group in the same period (P<0.05), while the test SEQ ID NO: 6 and 12 had no obvious improved therapeutic effect on the weight gain inhibition of the model animals.

TABLE 6

Effects of the test polypeptide compounds on changes in the body weight of model animals

| Group | Grouping day (D0, g) | Experimental day 5 (D5, g) | Experimental endpoint (D14, g) | Weight change range (D0-D14, %) |
|---|---|---|---|---|
| Normal control group | 273.86 ± 7.48 | 281.46 ± 12.97 | 310.67 ± 22.39 | 13.38 ± 6.25 |
| Model control group | 278.66 ± 9.87 | 236.52 ± 14.56*** | 267.73 ± 28.89** | −3.83 ± 10.82*** |
| Mesalazine treatment group | 276.64 ± 7.47 | 234.86 ± 8.07 | 264.43 ± 17.65 | −4.29 ± 7.79 |
| SEQ ID NO: 1 low dose group | 274.40 ± 9.10 | 251.65 ± 18.30$^{\#}$ | 296.07 ± 19.58$^{\#}$ | 7.96 ± 7.32$^{\#}$ |
| SEQ ID NO: 1 high dose group | 279.99 ± 10.57 | 263.90 ± 15.38$^{\#\#}$ | 299.37 ± 14.64$^{\#\#}$ | 6.97 ± 4.73$^{\#\#}$ |
| SEQ ID NO: 6 low dose group | 276.61 ± 9.81 | 243.72 ± 22.18 | 277.96 ± 29.18 | 0.48 ± 9.87 |
| SEQ ID NO: 6 high dose group | 275.55 ± 7.92 | 246.74 ± 22.76 | 279.67 ± 30.93 | 1.50 ± 10.78 |
| SEQ ID NO: 12 treatment group | 276.36 ± 7.47 | 244.90 ± 21.75 | 272.00 ± 33.21 | −1.52 ± 12.20 |

Note:

All data were statistically analyzed using mean ± standard deviation (SD). *P < 0.05, P < 0.01, *P < 0.001, ****P < 0.0001 represent the statistical analysis results of the model control group and the normal control group. $^{\#}$P < 0.05, $^{\#\#}$P < 0.01, represent the statistical analysis results of the test polypeptide compound treatment group and the model control group.

The DAI score results of the experimental period show that the test SEQ ID NO: 1, 6 and 12 had a significant improvement effect on the disease progression of ulcerative colitis in the model animals under the set treatment regimen. The fecal trait pathological characteristics and weight loss reactivity of the animals in the corresponding treatment groups were significantly alleviated, and the mean DAI scores showed a decrease, which was significantly statistically different from the model control group in the same period (P<0.05). The improvement in treatment effect of SEQ ID NO: 1 was the most significant, and the treatment effects of the SEQ ID NO: 1 and 6 were significantly dose-dependent.

TABLE 7

Effects of the test polypeptide compounds on the DAI scores of model animals

| Group | Experimental day 1 (D1, point) | Experimental day 3 (D3, point) | Experimental endpoint (D14, point) | $AUC_{(0\text{-}14\ d)}$ (D0-D14) |
|---|---|---|---|---|
| Normal control group | 0.3 ± 0.5 | 0.2 ± 0.4 | 0 | 1.10 ± 0.65 |
| Model control group | 3.8 ± 1.0 | 6.1 ± 1.0 | 2.2 ± 1.3 | 57.00 ± 2.97**** |
| Mesalazine treatment group | 4.2 ± 0.4 | 6.2 ± 0.6 | 2.1 ± 1.6 | 58.75 ± 2.93 |
| SEQ ID NO: 1 low dose group | 3.5 ± 1.3 | 4.9 ± 1.6 | 0.5 ± 0.7 | 37.65 ± 3.60$^{\#\#\#\#}$ |
| SEQ ID NO: 1 high dose group | 3.9 ± 0.6 | 4.3 ± 1.8 | 0.1 ± 0.3 | 30.65 ± 2.93$^{\#\#\#\#+++}$ |
| SEQ ID NO: 6 low dose group | 3.9 ± 0.9 | 5.0 ± 1.7 | 1.3 ± 1.2 | 49.65 ± 3.95$^{\#\#\#\#}$ |
| 6 high dose group | 4.2 ± 0.8 | 4.8 ± 1.0 | 0.7 ± 1.2 | 39.55 ± 3.99$^{\#\#\#\#++++}$ |
| SEQ ID NO: 12 treatment group | 4.1 ± 0.6 | 4.9 ± 1.0 | 1.4 ± 1.8 | 46.40 ± 3.68$^{\#\#\#\#}$ |

Note:

All data were statistically analyzed using mean ± standard deviation (SD). *P < 0.05, P < 0.01, *P < 0.001, and **P < 0.0001 represent the statistical analysis results of the model control group and the normal control group. $^{\#}$P < 0.05, $^{\#\#}$P < 0.01, $^{\#\#\#}$P < 0.001, and **P < 0.0001 represent the statistical analysis results of the animals in the test polypeptide compound treatment group and the model control group. $^{+}$P < 0.05, $^{++}$P < 0.01, $^{+++}$P < 0.001, and $^{++++}$P < 0.0001 represent the statistical analysis results between the SEQ ID NO: 1 or 6 dose groups.

The results of gross anatomy and colon tissue injury scores at the experimental endpoint show that the test SEQ ID NO: 1, 6 and 12 had obvious therapeutic effects on TNBS-induced gross colon injury status (colonic adhesion, ulcer and inflammation), colon ulcer focus area and abnormal increase in colon weight/length ratio. The degree of improvement was statistically significant compared with the model control group in the same period (P<0.05). The therapeutic effect of the SEQ ID NO: 1 was the most significant, and its therapeutic effect was significantly dose-dependent.

TABLE 8

Effects of the test polypeptide compounds on the gross damage and ulcer area of the colon in model animals

| Group | Colonic adhesion score (point) | Colon ulcer and inflammation score (point) | Colon ulcer area ($cm^2$) |
|---|---|---|---|
| Normal control group | 0 | 0 | 0 |
| Model control group | 2.80 ± 0.42**** | 4.40 ± 0.70**** | 7.72 ± 4.02**** |
| Mesalazine treatment group | 2.60 ± 0.52 | 4.30 ± 0.95 | 7.50 ± 3.51 |
| SEQ ID NO: 1 low dose group | 1.10 ± 0.57$^{\#\#\#\#}$ | 2.50 ± 0.85$^{\#\#\#\#}$ | 3.77 ± 1.91$^{\#}$ |
| SEQ ID NO: 1 high dose group | 0.60 ± 0.52$^{\#\#\#\#}$ | 1.40 ± 0.84$^{\#\#\#\#++}$ | 2.15 ± 0.74$^{\#\#\#+}$ |
| SEQ ID NO: 6 low dose group | 1.70 ± 0.67$^{\#\#\#}$ | 3.00 ± 0.94$^{\#\#}$ | 3.46 ± 2.06$^{\#\#}$ |
| SEQ ID NO: 6 high dose group | 1.30 ± 0.82$^{\#\#\#\#}$ | 2.50 ± 1.43$^{\#\#}$ | 3.66 ± 2.36$^{\#}$ |
| SEQ ID NO: 12 treatment group | 1.20 ± 0.63$^{\#\#\#\#}$ | 2.30 ± 0.82$^{\#\#\#\#}$ | 3.79 ± 1.63$^{\#}$ |

Note:

All data were statistically analyzed using mean ± standard deviation (SD). *P < 0.05, P < 0.01, *P < 0.001, and ****P < 0.0001 represent the statistical analysis results of the model control group and the normal control group. $^{\#}$P < 0.05, $^{\#\#}$P < 0.01, $^{\#\#\#}$P < 0.001, and $^{\#\#\#\#}$P < 0.0001 represent the statistical analysis results of the animals in the test polypeptide compound treatment group and the model control group. $^{+}$P < 0.05, $^{++}$P < 0.01, $^{+++}$P < 0.001, and $^{++++}$P < 0.0001 represent the statistical analysis results between the SEQ ID NO: 1 or 6 dose groups.

TABLE 9

Effects of the test polypeptide compounds on the colon weight/length ratio of model animals

| Group | Colon weight (g) | Colon length (cm) | Colon weight/length ratio (100* g/cm) |
|---|---|---|---|
| Normal control group | 1.90 ± 0.16 | 18.14 ± 1.23 | 10.53 ± 1.01 |
| Model control group | 3.26 ± 0.97*** | 12.76 ± 0.92**** | 25.37 ± 6.35**** |
| Mesalazine treatment group | 3.42 ± 1.15 | 14.76 ± 2.06 | 22.99 ± 5.49 |
| SEQ ID NO: 1 low dose group | 2.48 ± 0.46$^{\#}$ | 15.34 ± 1.99$^{\#\#}$ | 16.40 ± 3.29$^{\#\#\#}$ |
| SEQ ID NO: 1 high dose group | 2.20 ± 0.28$^{\#\#}$ | 16.55 ± 1.67$^{\#\#\#\#}$ | 13.37 ± 1.93$^{\#\#\#\#+}$ |
| SEQ ID NO: 6 low dose group | 2.23 ± 0.39$^{\#\#}$ | 13.37 ± 1.40 | 16.93 ± 3.87$^{\#\#}$ |
| SEQ ID NO: 6 high dose group | 2.41 ± 0.63$^{\#}$ | 13.89 ± 1.60 | 17.70 ± 5.71$^{\#}$ |
| SEQ ID NO: 12 treatment group | 2.10 ± 0.19$^{\#\#}$ | 13.74 ± 1.97 | 15.68 ± 3.14$^{\#\#\#}$ |

Note:

All data were statistically analyzed using mean ± standard deviation (SD). *P < 0.05, P < 0.01, *P < 0.001, and ****P < 0.0001 represent the statistical analysis results of the model control group and the normal control group. $^{\#}$P < 0.05, $^{\#\#}$P < 0.01, $^{\#\#\#}$P < 0.001, and $^{\#\#\#\#}$P < 0.0001 represent the statistical analysis results of the animals in the test polypeptide compound treatment group and the model control group. $^{+}$P < 0.05, $^{++}$P < 0.01, $^{+++}$P < 0.001, and $^{++++}$P < 0.0001 represent the statistical analysis results between the SEQ ID NO: 1 or 6 dose groups.

In this trial, TNBS was used for intervention by enema in male SD rats to induce colonic lesions and establish a rat ulcerative colitis model that conforms to the clinical characteristics of the disease. The next day after model induction, the treatment with test SEQ ID NO: 1, 6 and 12 and positive control drug mesalazine was started. During the treatment period (D1-D14), the changes in the weight, the disease activity index (DAI) score of ulcerative colitis, the score of gross colon damage manifestation (colonic adhesion, ulcer and inflammatory response), the ulcer area of the colon tissue and the ratio of colon weight to length of the experimental animals were monitored to evaluate the therapeutic effect of the test articles on the model of TNBS-induced ulcerative colitis in SD rat. The results showed that:

1) After TNBS induction, the experimental animals showed significant manifestations of ulcerative colitis disease, including significant weight loss, significant increase in ulcerative colitis disease activity index score (DAI score), significant increase in colon adhesion and ulcer score, increase in colon tissue ulcer area and significant increase in colon weight/length ratio, indicating that the rat ulcerative colitis model suitable for the pharmacodynamic study of this experiment was successfully established.

2) The test SEQ ID NO: 1 had a significant improvement effect on the weight loss response of the model animals under the set treatment regimen, and the degree of improvement was statistically significant compared with the model control group during the same period ($P<0.05$), while the test SEQ ID NO: 6, 12 and the positive control drug mesalazine did not show a significant weight improvement effect.

3) The test SEQ ID NO: 1, 6 and 12 had a significant improvement effect on the disease progression of ulcerative colitis in model animals under the set treatment regimen, and their DAI scores showed a significant decrease compared with the model control group during the same period. The therapeutic effect of the test SEQ ID NO: 1 was the most significant. At the same time, the treatment improvement effect of the test SEQ ID NO: 1 and 6 was significantly dose-dependent, while the positive control drug mesalazine had no significant effect on the disease symptoms of ulcerative colitis in model animals.

4) The test SEQ ID NO: 1, 6 and 12 had significant therapeutic effects on the gross damage manifestation of the colon in model animals under the set treatment regimen. Compared with the model control group in the same period, their colon adhesion score, colon ulcer and inflammation score and colon tissue ulcer area all showed a significant decrease, and the degree of improvement was statistically significant ($P<0.05$). The therapeutic effect of the test SEQ ID NO: 1 was the most significant, and its improved therapeutic effect was significantly dose-dependent.

5) The test SEQ ID NO: 1, 6 and 12 had a significant improvement effect on the colon atrophy process of model animals under the set treatment regimen. Compared with the model control group in the same period, their colon weight/length ratio was significantly decreased ($P<0.05$).

It can be seen that this experiment established a rat model of ulcerative colitis that conforms to the clinical characteristics of the pathogenesis, and the results of the efficacy evaluation in this model show that the test SEQ ID NO: 1, 6 and 12 all had significant therapeutic effects.

Example 4: Study on the Effect of Polypeptide Compounds on the Proliferation of CaCo-2 Cells In Vitro The following cell lines were used to study in vitro proliferation of the polypeptide compounds:

TABLE 10

| Cell line information | | | | |
|---|---|---|---|---|
| SEQ ID NO: | Cell line | Cancer type | Growth characteristics | Culture medium |
| 1 | CaCo-2 | Colorectal cancer | Adherence | (MEM + 0.01 mM NEAA) + 20% FBS |

Experimental Method:

Cells will be thrawed and maintained according to the culture conditions shown in Table 10.

Day 1 (cell plating): Cells in the logarithmic growth phase were collected, resuspended, counted using a cell counter and detected for activity. The cell suspension was diluted according to the required plating density and 90 μL of the cell suspension was added into each well of a 96-well plate (the plating density of cell would be adjusted based on historical data or density optimization experiments). While plating, three replicate wells were plated for each cell as T0 plates. All 96-well plates were placed in a 37° C., 5% CO2 thermostatic incubator overnight.

Day 2 (medium change): The medium with the corresponding serum concentration was replaced according to the platemap, 90 μL per well. Day 2: The TO plate was read and treated with the test compound. 10 μL of culture medium was added into each well of the TO plate to make up the total volume to 100 μL. 50 μL of CellTiter-Glo® Reagent was added to each well. The system was mixed and shaken for 5 min to fully lyse the cells. The system was incubated at room temperature for 10 min to stabilize the luminescent signal (note: temperature, cell density, and edge effects can all lead to uneven luminescent signals). Fluorescent signals were detected using EnVision Multi Label Reader. The test compound was configured according to the corresponding molecular weight, C1=91.08 μM, diluted C2=9.108 μM, and C3=0.9108 μM. Cisplatin was diluted as shown in Table 11 to prepare a 10× compound working solution. 10 μL of working solution (10×) was added to each well, so that the final volume per well of all plates was 100 μL. The cells were cultured in a 37° C., 5% CO2 incubator.

On the 5th day, treatment with the test compound was performed for 72 h (plate reading): whether the status of the drug-treated group and the control group is normal was observed under a microscope. 50 μL of CTG reagent was added to each well. The system was mixed on a shaker for 5 min to allow cells to fully lyse. The system was incubated at room temperature for 10 min to stabilize the luminescent signal. Fluorescent signals were read using EnVision Multi Label Reader.

TABLE 11

| Cisplatin concentration after dilution | | | | | | | | | | |
|---|---|---|---|---|---|---|---|---|---|---|
| | C1-1 | C2-1 | C3-1 | C4-1 | C5-1 | C6-1 | C7-1 | C8-1 | C9-1 | C10-1 |
| Concentration (μM) | 1000 | 333.33 | 111.11 | 37.04 | 12.35 | 4.12 | 1.37 | 0.46 | 0.15 | 0 |
| Solution volume (μL) | 90 | 90 | 90 | 90 | 90 | 90 | 90 | 90 | 90 | 90 |
| Broth volume (μL) | 209.7 | 209.7 | 209.7 | 209.7 | 209.7 | 209.7 | 209.7 | 209.7 | 209.7 | 209.7 |

$$\text{Cell viability (\%)} = Lum_{test\ compound}/Lum_{solvent\ control} \times 100\%.$$

Experimental results: The statistical results of the proliferation-promoting activity of the selected polypeptide compounds are shown in Table 12:

| SEQ ID NO:. | Proliferation-promoting activity |
|---|---|
| 1 | Cell viability > 110% |
| 20 | / |
| 44 | / |
| 45 | / |

The concentration gradient of the administered test substance set in this experimental system was set as C1=91.08 μM, diluted C2=9.108 μM, and C3=0.9108 μM, with 0.88% FBS as the reference. The experimental results show that the polypeptide SEQ ID NO: 1 of the present application has the activity of promoting the proliferation of Caco-2 cells, which is specifically manifested as an increase in cell viability after intervention.

In summary, the above-mentioned polypeptide compound of the present invention has a short peptide chain and is absorbed faster and better. The experimental results show that the polypeptide compound provided in the present application has the activity of alleviating the intestinal lumen dilatation of colitis in zebrafishes; and has a significant therapeutic effect in the trial for rat model of acute inflammatory bowel disease model. The polypeptide compound of the present invention has a significant effect of alleviating colitis and can be used to prepare drugs for treating enteritis, especially drugs for ulcerative colitis.

Although the present invention discloses the above Examples, the embodiments of the present invention are not limited to the above Examples, and any other changes, modifications, replacements, combinations, and simplifications that do not deviate from the present invention should be considered as equivalents and are included in the scope of protection of the present invention.

SEQUENCE LISTING

```
Sequence total quantity: 108
SEQ ID NO: 1             moltype = AA  length = 15
FEATURE                  Location/Qualifiers
source                   1..15
                         mol_type = protein
                         organism = synthetic construct
SEQUENCE: 1
KEPVPQAKPR KVAAQ                                                    15

SEQ ID NO: 2             moltype = AA  length = 11
FEATURE                  Location/Qualifiers
source                   1..11
                         mol_type = protein
                         organism = synthetic construct
SEQUENCE: 2
KEPVPQAKPR K                                                        11

SEQ ID NO: 3             moltype = AA  length = 10
FEATURE                  Location/Qualifiers
source                   1..10
                         mol_type = protein
                         organism = synthetic construct
SEQUENCE: 3
KEPVPQAKPR                                                          10

SEQ ID NO: 4             moltype = AA  length = 8
FEATURE                  Location/Qualifiers
source                   1..8
                         mol_type = protein
                         organism = synthetic construct
SEQUENCE: 4
KEPVPQAK                                                            8

SEQ ID NO: 5             moltype = AA  length = 7
FEATURE                  Location/Qualifiers
source                   1..7
                         mol_type = protein
                         organism = synthetic construct
SEQUENCE: 5
PRKVAAQ                                                             7

SEQ ID NO: 6             moltype = AA  length = 7
FEATURE                  Location/Qualifiers
source                   1..7
                         mol_type = protein
                         organism = synthetic construct
SEQUENCE: 6
EPVPQAK                                                             7

SEQ ID NO: 7             moltype = AA  length = 4
FEATURE                  Location/Qualifiers
```

```
source                 1..4
                       mol_type = protein
                       organism = synthetic construct
SEQUENCE: 7
KEPV                                                                        4

SEQ ID NO: 8           moltype = AA  length = 4
FEATURE                Location/Qualifiers
source                 1..4
                       mol_type = protein
                       organism = synthetic construct
SEQUENCE: 8
VAAQ                                                                        4

SEQ ID NO: 9           moltype = AA  length = 4
FEATURE                Location/Qualifiers
source                 1..4
                       mol_type = protein
                       organism = synthetic construct
SEQUENCE: 9
EPVP                                                                        4

SEQ ID NO: 10          moltype = AA  length = 4
FEATURE                Location/Qualifiers
source                 1..4
                       mol_type = protein
                       organism = synthetic construct
SEQUENCE: 10
KPRK                                                                        4

SEQ ID NO: 11          moltype = AA  length = 4
FEATURE                Location/Qualifiers
source                 1..4
                       mol_type = protein
                       organism = synthetic construct
SEQUENCE: 11
AKPR                                                                        4

SEQ ID NO: 12          moltype = AA  length = 4
FEATURE                Location/Qualifiers
source                 1..4
                       mol_type = protein
                       organism = synthetic construct
SEQUENCE: 12
PVPQ                                                                        4

SEQ ID NO: 13          moltype = AA  length = 4
FEATURE                Location/Qualifiers
source                 1..4
                       mol_type = protein
                       organism = synthetic construct
SEQUENCE: 13
VPQA                                                                        4

SEQ ID NO: 14          moltype = AA  length = 4
FEATURE                Location/Qualifiers
source                 1..4
                       mol_type = protein
                       organism = synthetic construct
SEQUENCE: 14
PQAK                                                                        4

SEQ ID NO: 15          moltype = AA  length = 4
FEATURE                Location/Qualifiers
source                 1..4
                       mol_type = protein
                       organism = synthetic construct
SEQUENCE: 15
RKVA                                                                        4

SEQ ID NO: 16          moltype = AA  length = 4
FEATURE                Location/Qualifiers
source                 1..4
                       mol_type = protein
                       organism = synthetic construct
SEQUENCE: 16
KVAA                                                                        4

SEQ ID NO: 17          moltype = AA  length = 4
```

-continued

```
FEATURE                Location/Qualifiers
source                 1..4
                       mol_type = protein
                       organism = synthetic construct
SEQUENCE: 17
QAKP                                                                      4

SEQ ID NO: 18          moltype = AA  length = 4
FEATURE                Location/Qualifiers
source                 1..4
                       mol_type = protein
                       organism = synthetic construct
SEQUENCE: 18
PRKV                                                                      4

SEQ ID NO: 19          moltype = AA  length = 15
FEATURE                Location/Qualifiers
source                 1..15
                       mol_type = protein
                       organism = synthetic construct
SEQUENCE: 19
AEPVPQAKPR KVAAQ                                                          15

SEQ ID NO: 20          moltype = AA  length = 15
FEATURE                Location/Qualifiers
source                 1..15
                       mol_type = protein
                       organism = synthetic construct
SEQUENCE: 20
KAPVPQAKPR KVAAQ                                                          15

SEQ ID NO: 21          moltype = AA  length = 15
FEATURE                Location/Qualifiers
source                 1..15
                       mol_type = protein
                       organism = synthetic construct
SEQUENCE: 21
KEAVPQAKPR KVAAQ                                                          15

SEQ ID NO: 22          moltype = AA  length = 15
FEATURE                Location/Qualifiers
source                 1..15
                       mol_type = protein
                       organism = synthetic construct
SEQUENCE: 22
KEPVAQAKPR KVAAQ                                                          15

SEQ ID NO: 23          moltype = AA  length = 15
FEATURE                Location/Qualifiers
source                 1..15
                       mol_type = protein
                       organism = synthetic construct
SEQUENCE: 23
KEPVPAAKPR KVAAQ                                                          15

SEQ ID NO: 24          moltype = AA  length = 15
FEATURE                Location/Qualifiers
source                 1..15
                       mol_type = protein
                       organism = synthetic construct
SEQUENCE: 24
KEPVPQAAPR KVAAQ                                                          15

SEQ ID NO: 25          moltype = AA  length = 15
FEATURE                Location/Qualifiers
source                 1..15
                       mol_type = protein
                       organism = synthetic construct
SEQUENCE: 25
KEPAPQAKPR KVAAQ                                                          15

SEQ ID NO: 26          moltype = AA  length = 15
FEATURE                Location/Qualifiers
source                 1..15
                       mol_type = protein
                       organism = synthetic construct
SEQUENCE: 26
KEPVPQAKAR KVAAQ                                                          15
```

```
SEQ ID NO: 27          moltype = AA  length = 15
FEATURE                Location/Qualifiers
source                 1..15
                       mol_type = protein
                       organism = synthetic construct
SEQUENCE: 27
KEPVPQAKPA KVAAQ                                                   15

SEQ ID NO: 28          moltype = AA  length = 15
FEATURE                Location/Qualifiers
source                 1..15
                       mol_type = protein
                       organism = synthetic construct
SEQUENCE: 28
KEPVPQAKPR AVAAQ                                                   15

SEQ ID NO: 29          moltype = AA  length = 15
FEATURE                Location/Qualifiers
source                 1..15
                       mol_type = protein
                       organism = synthetic construct
SEQUENCE: 29
KEPVPQAKPR KAAAQ                                                   15

SEQ ID NO: 30          moltype = AA  length = 15
FEATURE                Location/Qualifiers
source                 1..15
                       mol_type = protein
                       organism = synthetic construct
SEQUENCE: 30
KEPVPQAKPR KVAAA                                                   15

SEQ ID NO: 31          moltype = AA  length = 15
FEATURE                Location/Qualifiers
source                 1..15
                       mol_type = protein
                       organism = synthetic construct
SEQUENCE: 31
KEGVPQAKPR KVAAQ                                                   15

SEQ ID NO: 32          moltype = AA  length = 15
FEATURE                Location/Qualifiers
source                 1..15
                       mol_type = protein
                       organism = synthetic construct
SEQUENCE: 32
KEPVGQAKPR KVAAQ                                                   15

SEQ ID NO: 33          moltype = AA  length = 15
FEATURE                Location/Qualifiers
source                 1..15
                       mol_type = protein
                       organism = synthetic construct
SEQUENCE: 33
KEPVPQAKGR KVAAQ                                                   15

SEQ ID NO: 34          moltype = AA  length = 15
FEATURE                Location/Qualifiers
source                 1..15
                       mol_type = protein
                       organism = synthetic construct
SEQUENCE: 34
KEPVGQAKGR KVAAQ                                                   15

SEQ ID NO: 35          moltype = AA  length = 15
FEATURE                Location/Qualifiers
source                 1..15
                       mol_type = protein
                       organism = synthetic construct
SEQUENCE: 35
KEGVGQAKGR KVAAQ                                                   15

SEQ ID NO: 36          moltype = AA  length = 15
FEATURE                Location/Qualifiers
source                 1..15
                       mol_type = protein
                       organism = synthetic construct
SEQUENCE: 36
KEGVPQAKGR KVAAQ                                                   15
```

```
SEQ ID NO: 37           moltype = AA  length = 15
FEATURE                 Location/Qualifiers
source                  1..15
                        mol_type = protein
                        organism = synthetic construct
SEQUENCE: 37
KEGVGQAKPR KVAAQ                                                    15

SEQ ID NO: 38           moltype = AA  length = 10
FEATURE                 Location/Qualifiers
source                  1..10
                        mol_type = protein
                        organism = synthetic construct
SEQUENCE: 38
EPVPQAKPRK                                                          10

SEQ ID NO: 39           moltype = AA  length = 5
FEATURE                 Location/Qualifiers
source                  1..5
                        mol_type = protein
                        organism = synthetic construct
SEQUENCE: 39
PVPQA                                                               5

SEQ ID NO: 40           moltype = AA  length = 5
FEATURE                 Location/Qualifiers
source                  1..5
                        mol_type = protein
                        organism = synthetic construct
SEQUENCE: 40
PVPEA                                                               5

SEQ ID NO: 41           moltype = AA  length = 5
FEATURE                 Location/Qualifiers
source                  1..5
                        mol_type = protein
                        organism = synthetic construct
SEQUENCE: 41
PVPIA                                                               5

SEQ ID NO: 42           moltype = AA  length = 4
FEATURE                 Location/Qualifiers
source                  1..4
                        mol_type = protein
                        organism = synthetic construct
SEQUENCE: 42
PVPA                                                                4

SEQ ID NO: 43           moltype = AA  length = 6
FEATURE                 Location/Qualifiers
source                  1..6
                        mol_type = protein
                        organism = synthetic construct
SEQUENCE: 43
EPVPQA                                                              6

SEQ ID NO: 44           moltype = AA  length = 6
FEATURE                 Location/Qualifiers
source                  1..6
                        mol_type = protein
                        organism = synthetic construct
SEQUENCE: 44
PVPQAK                                                              6

SEQ ID NO: 45           moltype = AA  length = 7
FEATURE                 Location/Qualifiers
source                  1..7
                        mol_type = protein
                        organism = synthetic construct
SEQUENCE: 45
EPVPQAR                                                             7

SEQ ID NO: 46           moltype = AA  length = 7
FEATURE                 Location/Qualifiers
source                  1..7
                        mol_type = protein
                        organism = synthetic construct
SEQUENCE: 46
```

```
APVPQAK                                                         7

SEQ ID NO: 47          moltype = AA  length = 7
FEATURE                Location/Qualifiers
source                 1..7
                       mol_type = protein
                       organism = synthetic construct
SEQUENCE: 47
EPVPAAK                                                         7

SEQ ID NO: 48          moltype = AA  length = 7
FEATURE                Location/Qualifiers
source                 1..7
                       mol_type = protein
                       organism = synthetic construct
SEQUENCE: 48
EPVPQAA                                                         7

SEQ ID NO: 49          moltype = AA  length = 7
FEATURE                Location/Qualifiers
source                 1..7
                       mol_type = protein
                       organism = synthetic construct
SEQUENCE: 49
DPVPQAK                                                         7

SEQ ID NO: 50          moltype = AA  length = 7
FEATURE                Location/Qualifiers
source                 1..7
                       mol_type = protein
                       organism = synthetic construct
SEQUENCE: 50
NPVPQAK                                                         7

SEQ ID NO: 51          moltype = AA  length = 12
FEATURE                Location/Qualifiers
source                 1..12
                       mol_type = protein
                       organism = synthetic construct
SEQUENCE: 51
EPVPQAKPRK VA                                                   12

SEQ ID NO: 52          moltype = AA  length = 7
FEATURE                Location/Qualifiers
source                 1..7
                       mol_type = protein
                       organism = synthetic construct
SEQUENCE: 52
EPAPQAK                                                         7

SEQ ID NO: 53          moltype = AA  length = 7
FEATURE                Location/Qualifiers
source                 1..7
                       mol_type = protein
                       organism = synthetic construct
SEQUENCE: 53
EAVPQAK                                                         7

SEQ ID NO: 54          moltype = AA  length = 7
FEATURE                Location/Qualifiers
source                 1..7
                       mol_type = protein
                       organism = synthetic construct
SEQUENCE: 54
EPVAQAK                                                         7

SEQ ID NO: 55          moltype = AA  length = 7
FEATURE                Location/Qualifiers
source                 1..7
                       mol_type = protein
                       organism = synthetic construct
SEQUENCE: 55
EPVPEAK                                                         7

SEQ ID NO: 56          moltype = AA  length = 11
FEATURE                Location/Qualifiers
source                 1..11
                       mol_type = protein
                       organism = synthetic construct
```

```
SEQUENCE: 56
EPVPQAKPRK V                                                       11

SEQ ID NO: 57          moltype = AA  length = 9
FEATURE                Location/Qualifiers
source                 1..9
                       mol_type = protein
                       organism = synthetic construct
SEQUENCE: 57
EPVPQAKPR                                                          9

SEQ ID NO: 58          moltype = AA  length = 8
FEATURE                Location/Qualifiers
source                 1..8
                       mol_type = protein
                       organism = synthetic construct
SEQUENCE: 58
EPVPQAKP                                                           8

SEQ ID NO: 59          moltype = AA  length = 8
FEATURE                Location/Qualifiers
source                 1..8
                       mol_type = protein
                       organism = synthetic construct
SEQUENCE: 59
PVPQAKPR                                                           8

SEQ ID NO: 60          moltype = AA  length = 7
FEATURE                Location/Qualifiers
source                 1..7
                       mol_type = protein
                       organism = synthetic construct
SEQUENCE: 60
PVPQAKP                                                            7

SEQ ID NO: 61          moltype = AA  length = 15
FEATURE                Location/Qualifiers
source                 1..15
                       mol_type = protein
                       organism = synthetic construct
SITE                   1
                       note = D-Lysine
SEQUENCE: 61
KEPVPQAKPR KVAAQ                                                   15

SEQ ID NO: 62          moltype = AA  length = 15
FEATURE                Location/Qualifiers
source                 1..15
                       mol_type = protein
                       organism = synthetic construct
SITE                   2
                       note = D-Glutamic acid
SEQUENCE: 62
KEPVPQAKPR KVAAQ                                                   15

SEQ ID NO: 63          moltype = AA  length = 15
FEATURE                Location/Qualifiers
source                 1..15
                       mol_type = protein
                       organism = synthetic construct
SITE                   3
                       note = D-Proline
SEQUENCE: 63
KEPVPQAKPR KVAAQ                                                   15

SEQ ID NO: 64          moltype = AA  length = 15
FEATURE                Location/Qualifiers
source                 1..15
                       mol_type = protein
                       organism = synthetic construct
SITE                   4
                       note = D-Valine
SEQUENCE: 64
KEPVPQAKPR KVAAQ                                                   15

SEQ ID NO: 65          moltype = AA  length = 15
FEATURE                Location/Qualifiers
source                 1..15
                       mol_type = protein
```

```
                        organism = synthetic construct
SITE                    5
                        note = D-Proline
SEQUENCE: 65
KEPVPQAKPR KVAAQ                                                        15

SEQ ID NO: 66           moltype = AA  length = 15
FEATURE                 Location/Qualifiers
source                  1..15
                        mol_type = protein
                        organism = synthetic construct
SITE                    6
                        note = D-Glutamine
SEQUENCE: 66
KEPVPQAKPR KVAAQ                                                        15

SEQ ID NO: 67           moltype = AA  length = 15
FEATURE                 Location/Qualifiers
source                  1..15
                        mol_type = protein
                        organism = synthetic construct
SITE                    7
                        note = D-Alanine
SEQUENCE: 67
KEPVPQAKPR KVAAQ                                                        15

SEQ ID NO: 68           moltype = AA  length = 15
FEATURE                 Location/Qualifiers
source                  1..15
                        mol_type = protein
                        organism = synthetic construct
SITE                    8
                        note = D-Lysine
SEQUENCE: 68
KEPVPQAKPR KVAAQ                                                        15

SEQ ID NO: 69           moltype = AA  length = 15
FEATURE                 Location/Qualifiers
source                  1..15
                        mol_type = protein
                        organism = synthetic construct
SITE                    9
                        note = D-Proline
SEQUENCE: 69
KEPVPQAKPR KVAAQ                                                        15

SEQ ID NO: 70           moltype = AA  length = 15
FEATURE                 Location/Qualifiers
source                  1..15
                        mol_type = protein
                        organism = synthetic construct
SITE                    10
                        note = D-Arginine
SEQUENCE: 70
KEPVPQAKPR KVAAQ                                                        15

SEQ ID NO: 71           moltype = AA  length = 15
FEATURE                 Location/Qualifiers
source                  1..15
                        mol_type = protein
                        organism = synthetic construct
SITE                    11
                        note = D-Lysine
SEQUENCE: 71
KEPVPQAKPR KVAAQ                                                        15

SEQ ID NO: 72           moltype = AA  length = 15
FEATURE                 Location/Qualifiers
source                  1..15
                        mol_type = protein
                        organism = synthetic construct
SITE                    12
                        note = D-Valine
SEQUENCE: 72
KEPVPQAKPR KVAAQ                                                        15

SEQ ID NO: 73           moltype = AA  length = 15
FEATURE                 Location/Qualifiers
source                  1..15
```

```
                        mol_type = protein
                        organism = synthetic construct
SITE                    13
                        note = D-Alanine
SITE                    3
                        note = D-Val
SEQUENCE: 73
KEPVPQAKPR KVAAQ                                                    15

SEQ ID NO: 74           moltype = AA  length = 15
FEATURE                 Location/Qualifiers
source                  1..15
                        mol_type = protein
                        organism = synthetic construct
SITE                    14
                        note = D-Alanine
SEQUENCE: 74
KEPVPQAKPR KVAAQ                                                    15

SEQ ID NO: 75           moltype = AA  length = 15
FEATURE                 Location/Qualifiers
source                  1..15
                        mol_type = protein
                        organism = synthetic construct
SITE                    15
                        note = D-Glutamine
SEQUENCE: 75
KEPVPQAKPR KVAAQ                                                    15

SEQ ID NO: 76           moltype = AA  length = 7
FEATURE                 Location/Qualifiers
source                  1..7
                        mol_type = protein
                        organism = synthetic construct
SEQUENCE: 76
EGVPQAK                                                             7

SEQ ID NO: 77           moltype = AA  length = 7
FEATURE                 Location/Qualifiers
source                  1..7
                        mol_type = protein
                        organism = synthetic construct
SEQUENCE: 77
EPVGQAK                                                             7

SEQ ID NO: 78           moltype = AA  length = 7
FEATURE                 Location/Qualifiers
source                  1..7
                        mol_type = protein
                        organism = synthetic construct
SITE                    1
                        note = D-Glutamic acid
SEQUENCE: 78
EPVPQAK                                                             7

SEQ ID NO: 79           moltype = AA  length = 7
FEATURE                 Location/Qualifiers
source                  1..7
                        mol_type = protein
                        organism = synthetic construct
SITE                    2
                        note = D-Proline
SEQUENCE: 79
EPVPQAK                                                             7

SEQ ID NO: 80           moltype = AA  length = 7
FEATURE                 Location/Qualifiers
source                  1..7
                        mol_type = protein
                        organism = synthetic construct
SITE                    3
                        note = D-Valine
SEQUENCE: 80
EPVPQAK                                                             7

SEQ ID NO: 81           moltype = AA  length = 7
FEATURE                 Location/Qualifiers
source                  1..7
                        mol_type = protein
```

```
                        organism = synthetic construct
SITE                    4
                        note = D-Proline
SEQUENCE: 81
EPVPQAK                                                                     7

SEQ ID NO: 82           moltype = AA  length = 7
FEATURE                 Location/Qualifiers
source                  1..7
                        mol_type = protein
                        organism = synthetic construct
SITE                    5
                        note = D-Glutamine
SEQUENCE: 82
EPVPQAK                                                                     7

SEQ ID NO: 83           moltype = AA  length = 7
FEATURE                 Location/Qualifiers
source                  1..7
                        mol_type = protein
                        organism = synthetic construct
SITE                    6
                        note = D-Alanine
SEQUENCE: 83
EPVPQAK                                                                     7

SEQ ID NO: 84           moltype = AA  length = 7
FEATURE                 Location/Qualifiers
source                  1..7
                        mol_type = protein
                        organism = synthetic construct
SITE                    7
                        note = D-Lysine
SEQUENCE: 84
EPVPQAK                                                                     7

SEQ ID NO: 85           moltype = AA  length = 5
FEATURE                 Location/Qualifiers
source                  1..5
                        mol_type = protein
                        organism = synthetic construct
SEQUENCE: 85
KEPVP                                                                       5

SEQ ID NO: 86           moltype = AA  length = 5
FEATURE                 Location/Qualifiers
source                  1..5
                        mol_type = protein
                        organism = synthetic construct
SEQUENCE: 86
EPVPQ                                                                       5

SEQ ID NO: 87           moltype = AA  length = 6
FEATURE                 Location/Qualifiers
source                  1..6
                        mol_type = protein
                        organism = synthetic construct
SEQUENCE: 87
KEPVPQ                                                                      6

SEQ ID NO: 88           moltype = AA  length = 18
FEATURE                 Location/Qualifiers
source                  1..18
                        mol_type = protein
                        organism = synthetic construct
SEQUENCE: 88
VPYKEPVPQA KPRKVAAQ                                                         18

SEQ ID NO: 89           moltype = AA  length = 17
FEATURE                 Location/Qualifiers
source                  1..17
                        mol_type = protein
                        organism = synthetic construct
SITE                    1
                        note = Pyroglutamic acid
SEQUENCE: 89
ELKEPVPQAK PRKVAAQ                                                          17

SEQ ID NO: 90           moltype = AA  length = 18
```

```
FEATURE                 Location/Qualifiers
source                  1..18
                        mol_type = protein
                        organism = synthetic construct
SEQUENCE: 90
PAYKEPVPQA KPRKVAAQ                                            18

SEQ ID NO: 91           moltype = AA  length = 20
FEATURE                 Location/Qualifiers
source                  1..20
                        mol_type = protein
                        organism = synthetic construct
SEQUENCE: 91
RKDVYKEPVP QAKPRKVAAQ                                          20

SEQ ID NO: 92           moltype = AA  length = 13
FEATURE                 Location/Qualifiers
source                  1..13
                        mol_type = protein
                        organism = synthetic construct
SEQUENCE: 92
RKDVYKEPVP QAK                                                 13

SEQ ID NO: 93           moltype = AA  length = 12
FEATURE                 Location/Qualifiers
source                  1..12
                        mol_type = protein
                        organism = synthetic construct
SEQUENCE: 93
RKDVYEPVPQ AK                                                  12

SEQ ID NO: 94           moltype = AA  length = 9
FEATURE                 Location/Qualifiers
source                  1..9
                        mol_type = protein
                        organism = synthetic construct
SEQUENCE: 94
RKDVYPVPQ                                                      9

SEQ ID NO: 95           moltype = AA  length = 23
FEATURE                 Location/Qualifiers
source                  1..23
                        mol_type = protein
                        organism = synthetic construct
SEQUENCE: 95
GPETAFLRKE PVPQAKPRKV AAQ                                      23

SEQ ID NO: 96           moltype = AA  length = 15
FEATURE                 Location/Qualifiers
source                  1..15
                        mol_type = protein
                        organism = synthetic construct
SEQUENCE: 96
GPETAFLREP VPQAK                                               15

SEQ ID NO: 97           moltype = AA  length = 22
FEATURE                 Location/Qualifiers
source                  1..22
                        mol_type = protein
                        organism = synthetic construct
SEQUENCE: 97
SSEDIKEKEP VPQAKPRKVA AQ                                       22

SEQ ID NO: 98           moltype = AA  length = 14
FEATURE                 Location/Qualifiers
source                  1..14
                        mol_type = protein
                        organism = synthetic construct
SEQUENCE: 98
SSEDIKEEPV PQAK                                                14

SEQ ID NO: 99           moltype = AA  length = 11
FEATURE                 Location/Qualifiers
source                  1..11
                        mol_type = protein
                        organism = synthetic construct
SEQUENCE: 99
SSEDIKEPVP Q                                                   11
```

-continued

```
SEQ ID NO: 100          moltype = AA  length = 18
FEATURE                 Location/Qualifiers
source                  1..18
                        mol_type = protein
                        organism = synthetic construct
SEQUENCE: 100
VPPKEPVPQA KPRKVAAQ                                             18

SEQ ID NO: 101          moltype = AA  length = 14
FEATURE                 Location/Qualifiers
source                  1..14
                        mol_type = protein
                        organism = synthetic construct
SEQUENCE: 101
EPVPQAKSSE DIKE                                                 14

SEQ ID NO: 102          moltype = AA  length = 10
FEATURE                 Location/Qualifiers
source                  1..10
                        mol_type = protein
                        organism = synthetic construct
SEQUENCE: 102
EPVPQAKVPY                                                      10

SEQ ID NO: 103          moltype = AA  length = 15
FEATURE                 Location/Qualifiers
source                  1..15
                        mol_type = protein
                        organism = synthetic construct
SEQUENCE: 103
KEPVPQAKPR KVAAE                                                15

SEQ ID NO: 104          moltype = AA  length = 15
FEATURE                 Location/Qualifiers
source                  1..15
                        mol_type = protein
                        organism = synthetic construct
SEQUENCE: 104
KEPVPQAKPR KVAAN                                                15

SEQ ID NO: 105          moltype = AA  length = 15
FEATURE                 Location/Qualifiers
source                  1..15
                        mol_type = protein
                        organism = synthetic construct
SEQUENCE: 105
KQPVPQAKPR KVAAQ                                                15

SEQ ID NO: 106          moltype = AA  length = 15
FEATURE                 Location/Qualifiers
source                  1..15
                        mol_type = protein
                        organism = synthetic construct
SEQUENCE: 106
KEPIPQAKPR KVAAQ                                                15

SEQ ID NO: 107          moltype = AA  length = 4
FEATURE                 Location/Qualifiers
source                  1..4
                        mol_type = protein
                        organism = synthetic construct
SEQUENCE: 107
VPQA                                                            4

SEQ ID NO: 108          moltype = AA  length = 5
FEATURE                 Location/Qualifiers
source                  1..5
                        mol_type = protein
                        organism = synthetic construct
SEQUENCE: 108
VPQAK                                                           5
```

The invention claimed is:

1. Compound or a physiologically compatible salt thereof, wherein the compound is selected from:

Lys-Glu-Pro-Val-Pro-Gln-Ala-Lys-Pro-Arg-Lys-Val-Ala-Ala-Gln (SEQ ID NO: 1);

Lys-Glu-Pro-Val-Pro-Gln-Ala-Lys-Pro-Arg-Lys (SEQ ID NO: 2);

Lys-Glu-Pro-Val-Pro-Gln-Ala-Lys-Pro-Arg (SEQ ID NO: 3);

Lys-Glu-Pro-Val-Pro-Gln-Ala-Lys (SEQ ID NO: 4);

Glu-Pro-Val-Pro-Gln-Ala-Lys (SEQ ID NO: 6);

Ala-Glu-Pro-Val-Pro-Gln-Ala-Lys-Pro-Arg-Lys-Val-Ala-Ala-Gln (SEQ ID NO: 19);

Lys-Glu-Pro-Val-Pro-Gln-Ala-Lys-Ala-Arg-Lys-Val-Ala-Ala-Gln (SEQ ID NO: 26);

Lys-Glu-Pro-Val-Pro-Gln-Ala-Lys-Pro-Ala-Lys-Val-Ala-Ala-Gln (SEQ ID NO: 27);

Lys-Glu-Pro-Val-Pro-Gln-Ala-Lys-Pro-Arg-Ala-Val-Ala-Ala-Gln (SEQ ID NO: 28);

Lys-Glu-Pro-Val-Pro-Gln-Ala-Lys-Pro-Arg-Lys-Ala-Ala-Ala-Gln (SEQ ID NO: 29);

Lys-Glu-Pro-Val-Pro-Gln-Ala-Lys-Pro-Arg-Lys-Val-Ala-Ala-Ala (SEQ ID NO: 30);

Lys-Glu-Pro-Val-Pro-Gln-Ala-Lys-Gly-Arg-Lys-Val-Ala-Ala-Gln (SEQ ID NO: 33);

Glu-Pro-Val-Pro-Gln-Ala-Lys-Pro-Arg-Lys (SEQ ID NO: 38);

Glu-Pro-Val-Pro-Gln-Ala-Lys-Pro-Arg-Lys-Val-Ala (SEQ ID NO: 51);

Glu-Pro-Val-Pro-Gln-Ala-Lys-Pro-Arg-Lys-Val (SEQ ID NO: 56);

Glu-Pro-Val-Pro-Gln-Ala-Lys-Pro-Arg (SEQ ID NO: 57);

Glu-Pro-Val-Pro-Gln-Ala-Lys-Pro (SEQ ID NO: 58);

D-Lys-Glu-Pro-Val-Pro-Gln-Ala-Lys-Pro-Arg-Lys-Val-Ala-Ala-Gln (SEQ ID NO: 61);

Lys-D-Glu-Pro-Val-Pro-Gln-Ala-Lys-Pro-Arg-Lys-Val-Ala-Ala-Gln (SEQ ID NO: 62);

Lys-Glu-D-Pro-Val-Pro-Gln-Ala-Lys-Pro-Arg-Lys-Val-Ala-Ala-Gln (SEQ ID NO: 63);

Lys-Glu-Pro-D-Val-Pro-Gln-Ala-Lys-Pro-Arg-Lys-Val-Ala-Ala-Gln (SEQ ID NO: 64);

Lys-Glu-Pro-Val-D-Pro-Gln-Ala-Lys-Pro-Arg-Lys-Val-Ala-Ala-Gln (SEQ ID NO: 65);

Lys-Glu-Pro-Val-Pro-D-Gln-Ala-Lys-Pro-Arg-Lys-Val-Ala-Ala-Gln (SEQ ID NO: 66);

Lys-Glu-Pro-Val-Pro-Gln-D-Ala-Lys-Pro-Arg-Lys-Val-Ala-Ala-Gln (SEQ ID NO: 67);

Lys-Glu-Pro-Val-Pro-Gln-Ala-D-Lys-Pro-Arg-Lys-Val-Ala-Ala-Gln (SEQ ID NO: 68);

Lys-Glu-Pro-Val-Pro-Gln-Ala-Lys-D-Pro-Arg-Lys-Val-Ala-Ala-Gln (SEQ ID NO: 69);

Lys-Glu-Pro-Val-Pro-Gln-Ala-Lys-Pro-D-Arg-Lys-Val-Ala-Ala-Gln (SEQ ID NO: 70);

Lys-Glu-Pro-Val-Pro-Gln-Ala-Lys-Pro-Arg-D-Lys-Val-Ala-Ala-Gln (SEQ ID NO: 71);

Lys-Glu-Pro-Val-Pro-Gln-Ala-Lys-Pro-Arg-Lys-D-Val-Ala-Ala-Gln (SEQ ID NO: 72);

Lys-Glu-Pro-Val-Pro-Gln-Ala-Lys-Pro-Arg-Lys-Val-D-Ala-Ala-Gln (SEQ ID NO: 73);

Lys-Glu-Pro-Val-Pro-Gln-Ala-Lys-Pro-Arg-Lys-Val-Ala-D-Ala-Gln (SEQ ID NO: 74);

Lys-Glu-Pro-Val-Pro-Gln-Ala-Lys-Pro-Arg-Lys-Val-Ala-Ala-D-Gln (SEQ ID NO: 75);

D-Glu-Pro-Val-Pro-Gln-Ala-Lys (SEQ ID NO: 78);

Glu-D-Pro-Val-Pro-Gln-Ala-Lys (SEQ ID NO: 79);

Glu-Pro-D-Val-Pro-Gln-Ala-Lys (SEQ ID NO: 80);

Glu-Pro-Val-D-Pro-Gln-Ala-Lys (SEQ ID NO: 81);

Glu-Pro-Val-Pro-D-Gln-Ala-Lys (SEQ ID NO: 82);

Glu-Pro-Val-Pro-Gln-D-Ala-Lys (SEQ ID NO: 83);

Glu-Pro-Val-Pro-Gln-Ala-D-Lys (SEQ ID NO: 84);

Val-Pro-Tyr-Lys-Glu-Pro-Val-Pro-Gln-Ala-Lys-Pro-Arg-Lys-Val-Ala-Ala-Gln (SEQ ID NO: 88);

Pyro-Glu-Leu-Lys-Glu-Pro-Val-Pro-Gln-Ala-Lys-Pro-Arg-Lys-Val-Ala-Ala-Gln (Compound 89);

Pro-Ala-Tyr-Lys-Glu-Pro-Val-Pro-Gln-Ala-Lys-Pro-Arg-Lys-Val-Ala-Ala-Gln (SEQ ID NO 90);

Arg-Lys-Asp-Val-Tyr-Lys-Glu-Pro-Val-Pro-Gln-Ala-Lys-Pro-Arg-Lys-Val-Ala-Ala-Gln (SEQ ID NO: 91);

Arg-Lys-Asp-Val-Tyr-Lys-Glu-Pro-Val-Pro-Gln-Ala-Lys (SEQ ID NO: 92);

Arg-Lys-Asp-Val-Tyr-Glu-Pro-Val-Pro-Gln-Ala-Lys (SEQ ID NO: 93);

Gly-Pro-Glu-Thr-Ala-Phe-Leu-Arg-Lys-Glu-Pro-Val-Pro-Gln-Ala-Lys-Pro-Arg-Lys-Val-Ala-Ala-Gln (SEQ ID NO: 95);

Gly-Pro-Glu-Thr-Ala-Phe-Leu-Arg-Glu-Pro-Val-Pro-Gln-Ala-Lys (SEQ ID NO: 96);

Ser-Ser-Glu-Asp-Ile-Lys-Glu-Lys-Glu-Pro-Val-Pro-Gln-Ala-Lys-Pro-Arg-Lys-Val-Ala-Ala-Gln (SEQ ID NO: 97);

Ser-Ser-Glu-Asp-Ile-Lys-Glu-Glu-Pro-Val-Pro-Gln-Ala-Lys (SEQ ID NO: 98);

Val-Pro-Pro-Lys-Glu-Pro-Val-Pro-Gln-Ala-Lys-Pro-Arg-Lys-Val-Ala-Ala-Gln (SEQ ID NO 100);

Glu-Pro-Val-Pro-Gln-Ala-Lys-Ser-Ser-Glu-Asp-Ile-Lys-Glu (SEQ ID NO: 101);

Glu-Pro-Val-Pro-Gln-Ala-Lys-Val-Pro-Tyr (SEQ ID NO: 102);

Lys-Glu-Pro-Val-Pro-Gln-Ala-Lys-Pro-Arg-Lys-Val-Ala-Ala-Glu (SEQ ID NO: 103); or

Lys-Glu-Pro-Val-Pro-Gln-Ala-Lys-Pro-Arg-Lys-Val-Ala-Ala-Asn (SEQ ID NO: 104).

2. The compound according to claim 1 or a physiologically compatible salt thereof, wherein the compound is selected from:

Lys-Glu-Pro-Val-Pro-Gln-Ala-Lys-Pro-Arg-Lys-Val-Ala-Ala-Gln (SEQ ID NO: 1);

Lys-Glu-D-Pro-Val-Pro-Gln-Ala-Lys-Pro-Arg-Lys-Val-Ala-Ala-Gln (SEQ ID NO: 63);

Gly-Pro-Glu-Thr-Ala-Phe-Leu-Arg-Glu-Pro-Val-Pro-Gln-Ala-Lys (SEQ ID NO: 96);

Val-Pro-Pro-Lys-Glu-Pro-Val-Pro-Gln-Ala-Lys-Pro-Arg-Lys-Val-Ala-Ala-Gln (SEQ ID NO 100);

Lys-Glu-Pro-Val-Pro-Gln-Ala-Lys-Pro-Arg-Lys-Val-Ala-Ala-Asn (SEQ ID NO: 104);

Glu-Pro-Val-Pro-Gln-Ala-Lys (SEQ ID NO: 6);

Glu-Pro-Val-Pro-Gln-Ala-Lys-Pro-Arg (SEQ ID NO: 57);

Lys-Glu-Pro-Val-Pro-Gln-Ala-D-Lys-Pro-Arg-Lys-Val-Ala-Ala-Gln (SEQ ID NO: 68);

Lys-Glu-Pro-Val-Pro-Gln-Ala-Lys-Pro-Arg-Lys-D-Val-Ala-Ala-Gln (SEQ ID NO: 72);

Pyro-Glu-Leu-Lys-Glu-Pro-Val-Pro-Gln-Ala-Lys-Pro-Arg-Lys-Val-Ala-Ala-Gln (SEQ ID NO: 89);

Arg-Lys-Asp-Val-Tyr-Lys-Glu-Pro-Val-Pro-Gln-Ala-Lys (SEQ ID NO: 92);

Gly-Pro-Glu-Thr-Ala-Phe-Leu-Arg-Lys-Glu-Pro-Val-Pro-Gln-Ala-Lys-Pro-Arg-Lys-Val-Ala-Ala-Gln (SEQ ID NO: 95);

Ser-Ser-Glu-Asp-Ile-Lys-Glu-Lys-Glu-Pro-Val-Pro-Gln-Ala-Lys-Pro-Arg-Lys-Val-Ala-Ala-Gln (SEQ ID NO: 97);

Ser-Ser-Glu-Asp-Ile-Lys-Glu-Glu-Pro-Val-Pro-Gln-Ala-Lys (SEQ ID NO: 98);

Lys-Glu-Pro-Val-Pro-Gln-Ala-Lys (SEQ ID NO: 4);

Lys-Glu-Pro-Val-Pro-Gln-Ala-Lys-Ala-Arg-Lys-Val-Ala-Ala-Gln (SEQ ID NO: 26);

Lys-Glu-Pro-Val-Pro-Gln-Ala-Lys-Pro-Arg-Lys-Ala-Ala-Ala-Gln (SEQ ID NO: 29);

Glu-Pro-Val-Pro-Gln-Ala-Lys-Pro-Arg-Lys (SEQ ID NO: 38);

Glu-Pro-Val-Pro-Gln-Ala-Lys-Pro-Arg-Lys-Val-Ala (SEQ ID NO: 51);

Lys-D-Glu-Pro-Val-Pro-Gln-Ala-Lys-Pro-Arg-Lys-Val-Ala-Ala-Gln (SEQ ID NO: 62);

Lys-Glu-Pro-Val-D-Pro-Gln-Ala-Lys-Pro-Arg-Lys-Val-Ala-Ala-Gln (SEQ ID NO: 65);

Lys-Glu-Pro-Val-Pro-D-Gln-Ala-Lys-Pro-Arg-Lys-Val-Ala-Ala-Gln (SEQ ID NO: 66);

Lys-Glu-Pro-Val-Pro-Gln-D-Ala-Lys-Pro-Arg-Lys-Val-Ala-Ala-Gln (SEQ ID NO: 67);

Lys-Glu-Pro-Val-Pro-Gln-Ala-Lys-Pro-D-Arg-Lys-Val-Ala-Ala-Gln (SEQ ID NO: 70);

Lys-Glu-Pro-Val-Pro-Gln-Ala-Lys-Pro-Arg-Lys-Val-Ala-Ala-D-Gln (SEQ ID NO: 75);

Val-Pro-Tyr-Lys-Glu-Pro-Val-Pro-Gln-Ala-Lys-Pro-Arg-Lys-Val-Ala-Ala-Gln (SEQ ID NO: 88);

Pro-Ala-Tyr-Lys-Glu-Pro-Val-Pro-Gln-Ala-Lys-Pro-Arg-Lys-Val-Ala-Ala-Gln (SEQ ID NO 90);

Arg-Lys-Asp-Val-Tyr-Glu-Pro-Val-Pro-Gln-Ala-Lys (SEQ ID NO: 93); or

Lys-Glu-Pro-Val-Pro-Gln-Ala-Lys-Pro-Arg-Lys-Val-Ala-Ala-Glu (SEQ ID NO: 103).

3. A method for treating enteritis, comprising administering a therapeutically effective amount of a compound according to claim 1, or a physiologically compatible salt thereof, to a subject.

4. The method according to claim 3, wherein the enteritis includes specific enteritis and nonspecific enteritis.

5. The method according to claim 4, wherein the specific enteritis includes inflammatory bowel disease, necrotic enteropathy and dysbacteriosis enteritis.

6. The method according to claim 5, wherein the inflammatory bowel disease includes ulcerative colitis.

7. A pharmaceutical composition comprising the compound according to claim 1, or a physiologically compatible salt thereof, and a pharmaceutically acceptable excipient.

* * * * *